US012642671B2

(12) United States Patent
Alva et al.

(10) Patent No.: US 12,642,671 B2
(45) Date of Patent: Jun. 2, 2026

(54) SELF-POWERED PROSTHESIS

(71) Applicant: Orthosensor Inc., Dania, FL (US)

(72) Inventors: Carlos O. Alva, Boynton Beach, FL
(US); Matthias Verstraete, Chaam
(NL)

(73) Assignee: Howmedica Osteonics Corp., Mahwah,
NJ (US)

( * ) Notice: Subject to any disclaimer, the term of this
patent is extended or adjusted under 35
U.S.C. 154(b) by 687 days.

(21) Appl. No.: 18/127,986

(22) Filed: Mar. 29, 2023

(65) Prior Publication Data

US 2023/0255796 A1 Aug. 17, 2023

Related U.S. Application Data

(63) Continuation of application No. 18/108,954, filed on
Feb. 13, 2023.

(Continued)

(51) Int. Cl.
*A61F 2/46* (2006.01)
*A61B 5/00* (2006.01)
*A61B 5/06* (2006.01)

(52) U.S. Cl.
CPC ............ *A61F 2/4657* (2013.01); *A61B 5/062*
(2013.01); *A61B 5/4528* (2013.01); *A61B*
*5/6878* (2013.01); *A61F 2002/4666* (2013.01)

(58) Field of Classification Search
CPC .......... A61F 2/38; A61F 2/389; A61F 2/3859;
A61F 2/4657; A61B 5/062; A61B 5/4528;

(Continued)

(56) References Cited

U.S. PATENT DOCUMENTS 6,245,109 B1 6/2001 Mendes et al.
6,447,448 B1 9/2002 Ishikawa et al.
(Continued)

FOREIGN PATENT DOCUMENTS

DE 202015009423 U1 7/2017
IT JB2015006086 6/2017
(Continued)

OTHER PUBLICATIONS

Arami, A. et al., "Accurate Measurement of Concurrent Flexion-
Extension and Internal-External Rotations in Smart Knee Prosthe-
ses," IEEE Transactions on Biomedical Engineering, Sep. 2013, 8
pgs.

(Continued)

*Primary Examiner* — Brian A Dukert
(74) *Attorney, Agent, or Firm* — Lerner David LLP

(57) ABSTRACT

Disclosed herein are implants with sensors and methods for
powering implants with sensors. A joint implant according
to the present disclosure can include a first implant and a
second implant in contact with the first implant. The first
implant can be coupled to a first bone of a joint. The first
implant can include an energy generator coupled to a trans-
ducer. The second implant can include at least one sensor, a
battery coupled to the at least one sensor, and a receiver
coupled to the battery. The receiver can be disposed within
the second implant adjacent the transducer. Energy from the
energy generator can be transmitted from the transducer of
the first implant to the receiver of the second implant.

20 Claims, 57 Drawing Sheets

Related U.S. Application Data

(60) Provisional application No. 63/444,056, filed on Feb. 8, 2023, provisional application No. 63/444,045, filed on Feb. 8, 2023, provisional application No. 63/483,045, filed on Feb. 3, 2023, provisional application No. 63/443,146, filed on Feb. 3, 2023, provisional application No. 63/482,656, filed on Feb. 1, 2023, provisional application No. 63/482,659, filed on Feb. 1, 2023, provisional application No. 63/482,097, filed on Jan. 30, 2023, provisional application No. 63/482,109, filed on Jan. 30, 2023, provisional application No. 63/481,660, filed on Jan. 26, 2023, provisional application No. 63/481,053, filed on Jan. 23, 2023, provisional application No. 63/431,094, filed on Dec. 8, 2022, provisional application No. 63/423,932, filed on Nov. 9, 2022, provisional application No. 63/419,781, filed on Oct. 27, 2022, provisional application No. 63/419,522, filed on Oct. 26, 2022, provisional application No. 63/419,455, filed on Oct. 26, 2022, provisional application No. 63/359,384, filed on Jul. 8, 2022, provisional application No. 63/309,809, filed on Feb. 14, 2022.

(58) Field of Classification Search
CPC .... A61B 5/6878; A61B 5/4851; A61B 5/6812
See application file for complete search history.

(56) References Cited

U.S. PATENT DOCUMENTS

| | | | |
|---|---|---|---|
| 6,573,706 | B2 | 6/2003 | Mendes et al. |
| 6,583,630 | B2 | 6/2003 | Mendes et al. |
| 6,610,096 | B2 | 8/2003 | MacDonald |
| 6,821,299 | B2 | 11/2004 | Kirking et al. |
| 6,926,670 | B2 | 8/2005 | Rich et al. |
| 6,968,743 | B2 | 11/2005 | Rich et al. |
| 7,190,273 | B2 | 3/2007 | Liao et al. |
| 7,195,645 | B2 | 3/2007 | Disilvestro et al. |
| 7,218,232 | B2 | 5/2007 | DiSilvestro et al. |
| 7,328,131 | B2 | 2/2008 | Donofrio et al. |
| 7,347,874 | B2 | 3/2008 | Disilvestro |
| 7,384,403 | B2 | 6/2008 | Sherman |
| 7,470,288 | B2 | 12/2008 | Dietz et al. |
| 7,704,282 | B2 | 4/2010 | Disilvestro et al. |
| 7,766,862 | B2 | 8/2010 | Gerber et al. |
| 7,776,686 | B2 | 8/2010 | Makabe et al. |
| 7,900,518 | B2 | 3/2011 | Tai et al. |
| 7,976,534 | B2 | 7/2011 | Gerber et al. |
| 8,083,741 | B2 | 12/2011 | Morgan et al. |
| 8,121,678 | B2 | 2/2012 | Linder et al. |
| 8,241,296 | B2 | 8/2012 | Wasielewski |
| 8,388,553 | B2 | 3/2013 | James et al. |
| 8,419,801 | B2 | 4/2013 | DiSilvestro et al. |
| 8,506,514 | B2 | 8/2013 | Pedersen et al. |
| 8,509,888 | B2 | 8/2013 | Linder et al. |
| 8,551,092 | B2 | 10/2013 | Morgan et al. |
| 8,707,782 | B2 | 4/2014 | Stein et al. |
| 8,744,580 | B2 | 6/2014 | Doron et al. |
| 8,814,877 | B2 | 8/2014 | Wasielewski |
| 8,911,448 | B2 | 12/2014 | Stein |
| 8,956,418 | B2 | 2/2015 | Wasielewski et al. |
| 9,005,263 | B2 | 4/2015 | Boyden et al. |
| 9,380,980 | B2 | 7/2016 | Revie et al. |
| 9,439,797 | B2 | 9/2016 | Baym et al. |
| 9,459,087 | B2 | 10/2016 | Dunbar et al. |
| 9,532,730 | B2 | 1/2017 | Wasielewski |
| 9,622,701 | B2 | 4/2017 | Stein et al. |
| 9,687,670 | B2 | 6/2017 | Dacey, Jr. et al. |
| RE46,582 | E | 10/2017 | Morgan et al. |
| 9,839,374 | B2 | 12/2017 | Roche et al. |
| 10,034,779 | B2 | 7/2018 | Chen et al. |
| 10,080,509 | B2 | 9/2018 | Wasielewski |
| 10,188,464 | B2 | 1/2019 | Britton et al. |
| 10,219,696 | B2 | 3/2019 | Araci et al. |
| 10,234,934 | B2 | 3/2019 | Connor |
| 10,492,686 | B2 | 12/2019 | Hunter et al. |
| 10,531,826 | B2 | 1/2020 | Wasielewski et al. |
| 10,582,896 | B2 | 3/2020 | Revie et al. |
| 10,660,760 | B2 | 5/2020 | Johannaber et al. |
| 10,667,745 | B2 | 6/2020 | Anker et al. |
| 10,792,162 | B2 | 10/2020 | Johannaber et al. |
| 10,842,432 | B2 * | 11/2020 | Goodchild ............ A61B 90/06 |
| 10,842,636 | B2 | 11/2020 | Johannaber et al. |
| 10,898,106 | B2 | 1/2021 | Bodewes et al. |
| 10,966,788 | B2 | 4/2021 | Britton et al. |
| 11,027,140 | B2 | 6/2021 | Wang et al. |
| 11,071,456 | B2 | 7/2021 | Hunter et al. |
| 11,134,870 | B2 | 10/2021 | Lieb et al. |
| 11,234,825 | B2 | 2/2022 | Johannaber et al. |
| 11,234,852 | B2 | 2/2022 | Koo |
| 11,389,111 | B2 | 7/2022 | Bae |
| 2004/0158294 | A1 | 8/2004 | Thompson |
| 2004/0243148 | A1 | 12/2004 | Wasielewski |
| 2005/0010301 | A1 | 1/2005 | Disilvestro et al. |
| 2006/0047283 | A1 | 3/2006 | Evans et al. |
| 2006/0271199 | A1 | 11/2006 | Johnson |
| 2007/0005141 | A1 | 1/2007 | Sherman |
| 2007/0089518 | A1 | 4/2007 | Ericson et al. |
| 2007/0239165 | A1 | 10/2007 | Amirouche |
| 2008/0033527 | A1 | 2/2008 | Nunez et al. |
| 2008/0065225 | A1 | 3/2008 | Wasielewski et al. |
| 2008/0077016 | A1 | 3/2008 | Sparks et al. |
| 2010/0171394 | A1 | 7/2010 | Glenn et al. |
| 2010/0204551 | A1 | 8/2010 | Roche |
| 2010/0204802 | A1 | 8/2010 | Wilson et al. |
| 2010/0249576 | A1 | 9/2010 | Askarinya et al. |
| 2014/0303739 | A1 | 10/2014 | Mentink et al. |
| 2016/0015319 | A1 | 1/2016 | Billi et al. |
| 2016/0029952 | A1 | 2/2016 | Hunter |
| 2016/0089079 | A1 | 3/2016 | Stein |
| 2016/0192878 | A1 | 7/2016 | Hunter |
| 2016/0242646 | A1 | 8/2016 | Obma |
| 2016/0302721 | A1 | 10/2016 | Wiedenhoefer et al. |
| 2016/0338644 | A1 | 11/2016 | Connor |
| 2017/0065436 | A1 | 3/2017 | Singh et al. |
| 2017/0196508 | A1 | 7/2017 | Hunter |
| 2017/0231559 | A1 | 8/2017 | Cuevas et al. |
| 2017/0296118 | A1 | 10/2017 | Swanson et al. |
| 2017/0319141 | A1 | 11/2017 | Revie et al. |
| 2017/0340243 | A1 | 11/2017 | Jain et al. |
| 2018/0116805 | A1 | 5/2018 | Johannaber et al. |
| 2018/0160966 | A1 | 6/2018 | Inan et al. |
| 2018/0235514 | A1 | 8/2018 | DiSilvestro et al. |
| 2019/0167447 | A1 | 6/2019 | Angibaud |
| 2019/0167988 | A1 | 6/2019 | Shahriari et al. |
| 2019/0283247 | A1 | 9/2019 | Chang et al. |
| 2019/0298998 | A1 | 10/2019 | Coleman et al. |
| 2019/0336049 | A1 | 11/2019 | Shah et al. |
| 2019/0350523 | A1 | 11/2019 | Bailey et al. |
| 2020/0000400 | A1 | 1/2020 | McKinnon et al. |
| 2020/0178898 | A1 | 6/2020 | Revie et al. |
| 2020/0383796 | A1 | 12/2020 | Johannaber et al. |
| 2021/0022874 | A1 | 1/2021 | Johannaber et al. |
| 2021/0059554 | A1 | 3/2021 | Armbruster |
| 2021/0141034 | A1 | 5/2021 | Sharma et al. |
| 2021/0153947 | A1 | 5/2021 | Britton et al. |
| 2021/0186454 | A1 | 6/2021 | Behzadi et al. |
| 2021/0228160 | A1 | 7/2021 | Braganza et al. |
| 2021/0290063 | A1 | 9/2021 | Roche |
| 2021/0366610 | A1 | 11/2021 | Gross et al. |
| 2021/0369471 | A1 | 12/2021 | Gross et al. |
| 2021/0378841 | A1 | 12/2021 | Mokete |
| 2021/0386292 | A1 | 12/2021 | Hunter et al. |
| 2022/0000422 | A1 | 1/2022 | Gross et al. |
| 2022/0015672 | A1 | 1/2022 | Lieb et al. |
| 2022/0047162 | A1 | 2/2022 | Hunter et al. |

FOREIGN PATENT DOCUMENTS

| | | | |
|---|---|---|---|
| WO | 2017096138 | A1 | 6/2017 |
| WO | 2021154885 | A2 | 8/2021 |

(56) References Cited

FOREIGN PATENT DOCUMENTS

OTHER PUBLICATIONS

Ibrahim A, Jain M, et al., "A Smart Knee Implant Using Triboelectric Energy Harvesters". Smart Mater Struct. Feb. 2019;28(2):025040. doi: 10.1088/1361-665X/aaf3f1. Epub Jan. 25, 2019. 39 pgs.

Bhatnagar, Vikrant & Owende, Philip, "Energy Harvesting for Assistive and Mobile Applications". Energy Science & Engineering. 3. 10.1002/ese3.63. (Feb. 2015). 21 pgs.

Schaufler, Anna, et al. "Sensor-based measurement for advanced monitoring and early detection of PE wear in total knee arthroplasties" Current Directions in Biomedical Engineering, vol. 7, No. 2, Oct. 2021, pp. 283-286. <https://doi.org/10.1515/cdbme-2021-2072>.

International Search Report and Written Opinion issued in Appln. No. PCT/US2023/013019 mailed May 24, 2023 (22 pages).

* cited by examiner

102

126      124      128

114

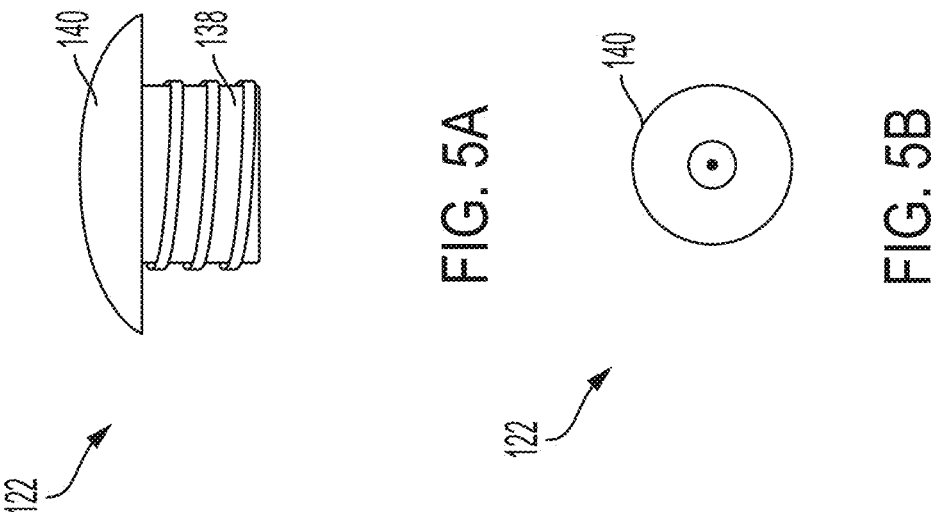
FIG. 5A
FIG. 5B
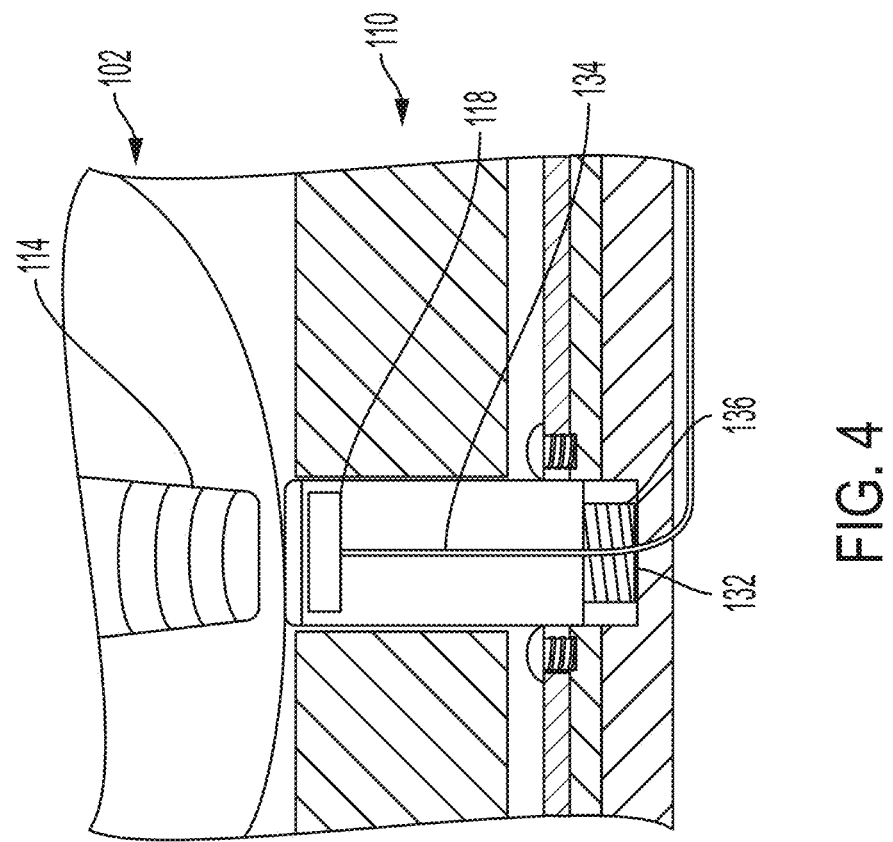
FIG. 4

1210

PRESSURE

IMU

1276

PE

TI

1204

1210

1212

2400

SELF-POWERED PROSTHESIS

CROSS-REFERENCE TO RELATED APPLICATIONS

This application is a continuation of U.S. patent application Ser. No. 18/108,954 filed on Feb. 13, 2023, which claims the benefit of the filing date of U.S. Provisional Patent Application No. 63/444,056 filed Feb. 8, 2023, and which claims the benefit of the filing date of U.S. Provisional Patent Application No. 63/444,045, filed Feb. 8, 2023, and which claims the benefit of the filing date of U.S. Provisional Patent Application No. 63/443,146 filed Feb. 3, 2023, and which claims the benefit of the filing date of U.S. Provisional Patent Application No. 63/483,045, filed Feb. 3, 2023, and which claims the benefit of the filing date of U.S. Provisional Patent Application No. 63/482,659, filed Feb. 1, 2023, and which claims the benefit of the filing date of U.S. Provisional Patent Application No. 63/482,656 filed Feb. 1, 2023, and which claims the benefit of the filing date of U.S. Provisional Patent Application No. 63/482,097 filed Jan. 30, 2023, and which claims the benefit of the filing date of U.S. Provisional Patent Application No. 63/482,109 filed Jan. 30, 2023, and which claims the benefit of the filing date of U.S. Provisional Patent Application No. 63/481,660 filed Jan. 26, 2023, and which claims the benefit of the filing date of U.S. Provisional Patent Application No. 63/481,053 filed Jan. 23, 2023, and which claims the benefit of the filing date of U.S. Provisional Patent Application No. 63/431,094 filed Dec. 8, 2022, and which claims the benefit of the filing date of U.S. Provisional Patent Application No. 63/423,932 filed Nov. 9, 2022, and which claims the benefit of the filing date of U.S. Provisional Patent Application No. 63/419,781 filed Oct. 27, 2022, and which claims the benefit of the filing date of U.S. Provisional Patent Application No. 63/419,522 filed Oct. 26, 2022, and which claims the benefit of the filing date of United States Provisional Patent Application No. 63/419,455 filed Oct. 26, 2022, and which claims the benefit of the filing date of U.S. Provisional Patent Application No. 63/359,384 filed Jul. 8, 2022, and which claims the benefit of the filing date of U.S. Provisional Patent Application No. 63/309,809 filed Feb. 14, 2022, the disclosures of all of which are hereby incorporated herein by reference in their entirety.

FIELD OF INVENTION

The present disclosure relates to implants with sensors and methods for powering implants with sensors, and particularly to self-powered implants and methods for harvesting energy for self-powered implants.

BACKGROUND OF THE INVENTION

An implant with sensors requires power for operating these sensors throughout the lifespan of the implant. Sensors require power to detect, measure, and transmit various human body metrics to monitor implant performance and patient recovery.

Accommodating a battery within an implant, particularly a battery large enough to power an implant throughout the lifespan of the implant, can be challenging. Sensors and associated electronics for the sensor require space within an implant further limit space available for a battery. Larger batteries with higher output capacity must be biocompatible for safe and long-lasting or permanent use.

Depending on the type of implant, the need for power requirements can vary considerably. For example, a pacemaker will require a continuous and steady source of power throughout its lifespan, while a joint implant may only require intermittent power to its sensors during particular activities of the patient.

Utilizing rechargeable batteries in an implant may provide longer implant lifespan, however, these batteries will require periodic and regular charging from an external source. A patient's failure to timely recharge these batteries from the external source will lead to implant sensor failure and inadequate monitoring of the implant and/or patient condition.

Therefore, there exists a need for improved implants with sensors and related methods for powering implants with sensors.

BRIEF SUMMARY OF THE INVENTION

Disclosed herein are implants with sensors and methods for powering implants with sensors.

In accordance with an aspect of the present disclosure, a joint implant is provided. A joint implant according to this aspect may include a first implant and a second implant in contact with or disposed adjacent the first implant. The first implant may be coupled to a first bone of a joint. The first implant may include an energy generator coupled to a transducer. The transducer may be disposed within the first implant. The second implant may include at least one sensor, a battery coupled and a receiver. The battery may be coupled to the least one sensor. The receiver may be coupled to the battery. The receiver may be disposed within the second implant adjacent the transducer. Energy from the energy generator may be transmitted from the transducer of the first implant to the receiver of the second implant.

Continuing in accordance with this aspect, energy from the energy generator may be acoustically transmitted from the transducer of the first implant to the receiver of the second implant. The transducer may be an ultrasonic transducer. The receiver may be an ultrasonic receiver. Energy from the energy generator may be ultrasonically transmitted from the ultrasonic transducer of the first implant to the ultrasonic receiver of the second implant.

Continuing in accordance with this aspect, the energy generator may include a plurality of magnets. The energy generator may generate energy by magnetic induction caused by motion between the plurality of magnets. The motion between the plurality of magnets may be caused by joint implant motion. The energy generator may include one or more biasing elements coupled to the magnets. The biasing elements may be springs.

Continuing in accordance with this aspect, the energy generator may include triboelectric material. The triboelectric material may include a first triboelectric layer with a first electron affinity and a second triboelectric layer with a second electron affinity. The first electron affinity may be different from the second electron affinity. The first triboelectric layer may be separated by a distance from the second triboelectric layer. A motion of the joint implant may cause the distance to vary to generate energy. The first triboelectric layer may slide along the second triboelectric layer during joint implant motion to generate energy.

Continuing in accordance with this aspect, a plurality of sensors may be coupled to the battery. The plurality of sensors may include any of a magnetic sensor, a load sensor, a pH sensor, a temperature sensor, and a pressure sensor coupled to the battery.

Continuing in accordance with this aspect, the battery may receive energy from the receiver.

Continuing in accordance with this aspect, the plurality of sensors, the battery and the receiver may be disposed within a housing of the second implant. The housing may be hermetically sealed. The housing may be metallic.

Continuing in accordance with this aspect, the first implant may define a first monolithic body and the second implant defines a second monolithic body.

Continuing in accordance with this aspect, the joint implant may be a knee implant. The first implant may be a tibial stem and the second implant may be a tibial insert. The tibial stem may be made of cobalt-chrome or titanium. The tibial insert may be made of a cross-linked polyethylene. The first bone may be a tibia.

Continuing in accordance with this aspect, the joint implant may be any of a shoulder, a hip, an ankle, and a wrist implant.

In accordance with another aspect of the present disclosure, an implant system is provided. An implant system according to this aspect, may include a first implant and a second implant disposed adjacent the first implant. The first implant may be coupled to a first bone. The first implant may include an energy generator coupled to a transducer. The transducer may be disposed within the first implant. The second implant may include at least one sensor, and a receiver. The receiver may be coupled to the at least one sensor. The receiver may be disposed within the second implant adjacent the transducer. Energy from the energy generator may be acoustically transmitted from the transducer of the first implant to the receiver of the second implant. The transducer may be an ultrasonic transducer. The receiver may be an ultrasonic receiver.

Continuing in accordance with this aspect, energy from the energy generator may be ultrasonically transmitted from the ultrasonic transducer of the first implant to the ultrasonic receiver of the second implant. The energy generator may include a plurality of magnets. The energy generator may generate energy by magnetic induction caused by motion between the plurality of magnets. The motion between the plurality of magnets may be caused by first and/or second implant motion. The energy generator may include one or more biasing elements coupled to the magnets. The biasing elements may be a spring.

Continuing in accordance with this aspect, the energy generator may include triboelectric material. The triboelectric material may include a first triboelectric layer with a first electron affinity and a second triboelectric layer with a second electron affinity. The first electron affinity may be different from the second electron affinity. The first triboelectric layer may be separated by a distance from the second triboelectric layer. A motion of the first and/or second implant may cause the distance to vary to generate energy. The first triboelectric layer may slide along the second triboelectric layer during first and/or second motion to generate energy.

Continuing in accordance with this aspect, the plurality of sensors may include any of a magnetic sensor, a load sensor, a pH sensor, a temperature sensor, an accelerometer, a gyroscope, an inertial measurement unit ("IMU") and a pressure sensor coupled to the battery. The plurality of sensors may receive energy from the receiver.

Continuing in accordance with this aspect, the plurality of sensors and the receiver may be disposed within a housing of the second implant. The housing may be hermetically sealed. The housing may be metallic.

Continuing in accordance with this aspect, the first implant may define a first monolithic body and the second implant may define a second monolithic body.

Continuing in accordance with this aspect, the implant system may be any of a knee implant, a shoulder implant, a hip implant, an ankle implant, and a wrist implant.

In accordance with another aspect of the present disclosure, a joint implant is provided. A joint implant according to this aspect may include a first implant and a second implant. The first implant may be coupled to a first bone of a joint. The first implant may include a battery coupled to a transducer. The transducer may be disposed within the first implant. The second implant may be in contact with the first implant. The second implant may include at least one sensor and a receiver. The receiver may be coupled to the at least one sensor. The receiver may be disposed within the second implant adjacent the transducer. Energy from the battery may be acoustically transmitted from the transducer of the first implant to the receiver of the second implant.

Continuing in accordance with this aspect, the battery may be rechargeable.

In accordance with another aspect of the present a disclosure, a method for powering a joint implant is provided. A method according to this aspect may include the steps of providing a first implant, coupling an energy generator of the first implant to a transducer, providing a second implant, coupling at least one sensor disposed within the second implant to a battery, coupling a receiver to the battery, and transmitting energy from the energy generator to the transducer of the first implant to the receiver of the second implant. The first implant may be configured to be placed on a first bone. The transducer may be disposed within the first implant. The second implant may be configured to be placed in contact with the first implant. The battery may be disposed within the second implant. The receiver may be disposed within the second implant adjacent the transducer.

Continuing in accordance with this aspect, the step of transmitting energy may include acoustically transmitting energy from the transducer of the first implant to the receiver of the second implant.

In accordance with another aspect of the present disclosure, a method for powering a joint implant is provided. A method according to this aspect may include the steps of providing a first implant configured to be placed on a first bone and providing a second implant configured to be placed adjacent the first implant. The first implant may include an energy generator coupled to a transducer. The transducer may be disposed within the first implant. The second implant may include at least one sensor coupled to a battery. The battery may be coupled to a receiver. The receiver may be disposed within the second implant adjacent the transducer such that the energy generator may transmit energy from the energy generator to the transducer of the first implant to the receiver of the second implant.

BRIEF DESCRIPTION OF THE DRAWINGS

A more complete appreciation of the subject matter of the present disclosure and the various advantages thereof can be realized by reference to the following detailed description, in which reference is made to the following accompanying drawings:

FIG. 4 is a partial view of an encoder read head and a load sensor of a tibial implant of the knee joint implant of FIG. 1;

FIG. 5A is a front view of an antenna of the knee joint implant of FIG. 1;

FIG. 5B is a top view of the antenna of FIG. 5A;

DETAILED DESCRIPTION

Reference will now be made in detail to the various embodiments of the present disclosure illustrated in the accompanying drawings. Wherever possible, the same or like reference numbers will be used throughout the drawings to refer to the same or like features within a different series of numbers (e.g., 100-series, 200-series, etc.). It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

As used herein, the terms "load" and "force" will be used interchangeably and as such, unless otherwise stated, the explicit use of either term is inclusive of the other term. Similarly, the terms "magnetic markers" and "markers" will be used interchangeably and as such, unless otherwise stated, the explicit use of either term is inclusive of the other term.

As used herein, the terms "power" and "energy" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term. The term "joint implant" means a joint implant system comprising two or more implants. Similarly, the terms "energy generator" and "energy harvester" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the present disclosure. As used herein, when referring to bones or other parts of the body, the term "anterior" means toward the front part of the body or the face, and the term "posterior" means toward the back of the body. The term "medial" means toward the midline of the body, and the term "lateral" means away from the midline of the body. The term "superior" means closer to the head, and the term "inferior" means more distant from the head.

Figure 1:
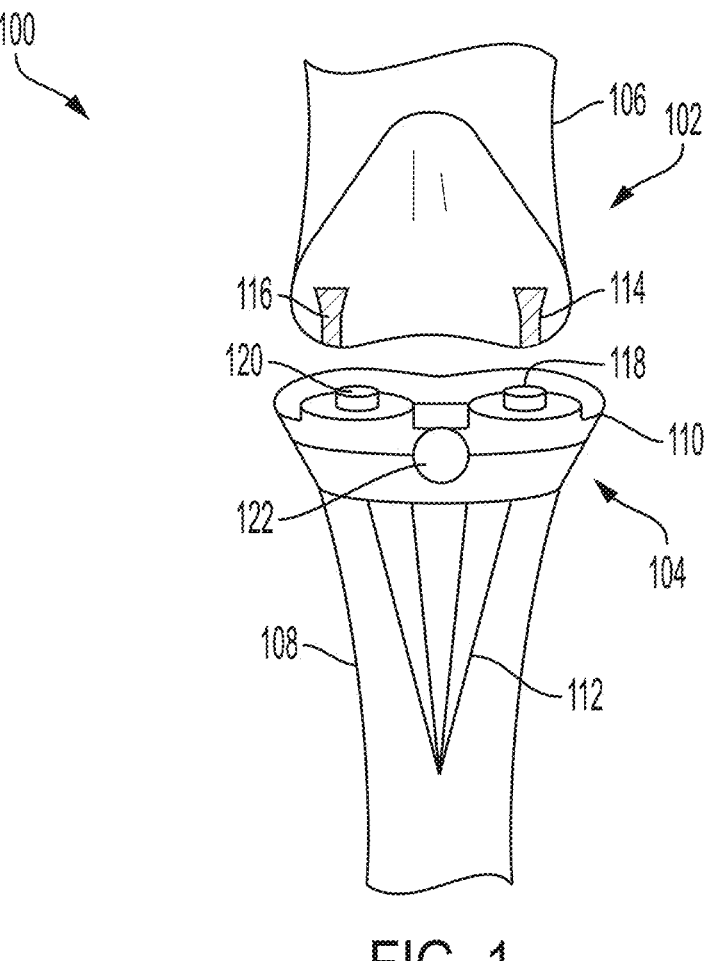
FIG. 1 is a front view of a knee joint implant according to an embodiment of the present disclosure.

FIG. 1 is a front view of a knee joint implant 100 according to an embodiment of the present disclosure. Knee joint implant 100 includes a femoral implant 102 located on a femur 106 and a tibial implant 104 located on a tibia 108. Tibial implant 104 has a tibial insert 110 configured to contact femoral implant 102, and a tibial baseplate or tibial stem 112 extending distally into tibia 108. Femoral implant 102 includes a medial encoder track 114 located on a medial side and a lateral encoder track 116 on a lateral side of the femoral implant. While the encoder tracks are shown along a surface of femoral implant 102 in FIG. 1, these tracks can be located within or partially within a femoral implant on the medial and lateral sides thereof in other embodiments. The encoder tracks can be made of various structures, including magnetic tape of varying lengths and magnetic markers positioned at discrete locations. The resolution of the encoder track can be adjusted depending on the required precision of the measured parameters such as joint displacement, joint rotation, joint slip, etc. Tibial insert 110 includes a medial read head 118 and lateral read head 120 to read a magnetic flux density from medial encoder track 114 and lateral encoder track 116, respectively. Medial read head 118 and lateral read head 120 can be any suitable magnetometer configured to detect and measure magnetic flux density, such as a Hall effect sensor. As tibia 108 rotates with reference to femur 106 during knee flexion and extension, medial encoder track 114 and lateral encoder track 116 move along medial read head 118 and lateral read head 120, respectively. This movement causes a change in magnetic flux density which is detected by read heads 118, 120, and can be utilized to measure knee joint implant 100 movement, rotation, speed and range of articulation, motion/activity, joint slip, and other motion related information. The magnetic-mechanic coupling of the read heads with the encoder tracks allows for direct, instantaneous, and continuous measurements of these knee joint implant parameters. A data transmitter such as an antenna 122 located on tibial insert 110 transmits the knee joint implant parameters measured by the read heads via Bluetooth or other similar wireless means to an external source such as a smart phone, tablet, monitor, network, etc. to allow for real time review of the knee joint implant performance.

Figure 2:
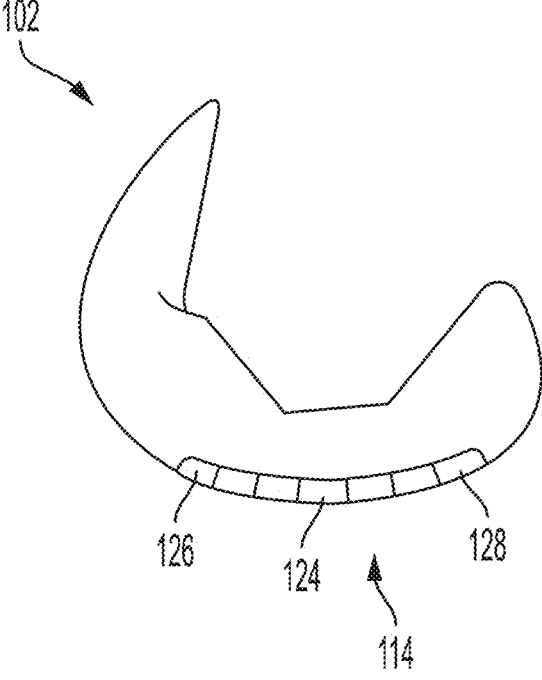
FIG. 2 is a side view of a femoral implant of the knee joint implant of FIG. 1.
Figure 3B:
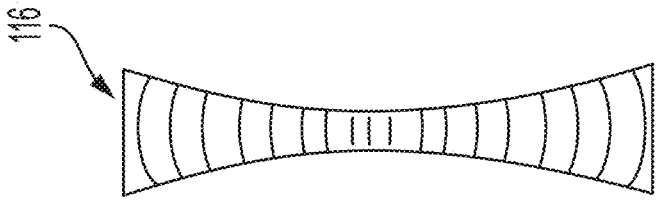
FIG. 3B is schematic view of encoder tracks of the femoral implant of FIG. 2.
Figure 3A:
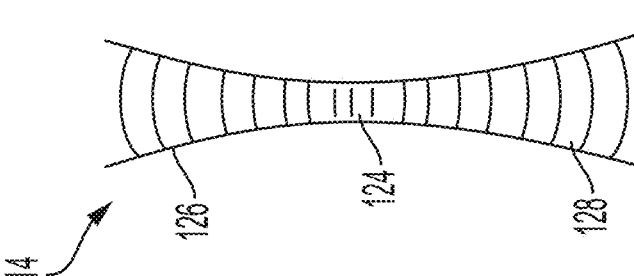
FIG. 3A is a bottom view of the femoral implant of FIG. 2.

FIGS. 2-3B illustrate additional details of femoral implant 102, medial encoder track 114 and lateral encoder track 116. As shown in FIG. 2, medial encoder track 114 extends from an anterior portion 126 of femoral implant 102 to a posterior portion 128 of the femoral implant along a track axis 130. Medial encoder track 114 includes a central portion 124 which is narrower than anterior and posterior portions 126, 128 as shown in FIG. 3A. As shown in FIG. 3B, medial encoder track 114 includes arched or curved magnetic lines to compensate for joint rotations in order to maintain uniform readings during a full range of motion of the knee joint. Similarly, lateral encoder track 116 extends from an anterior portion to a posterior portion of the femoral implant and includes a narrow central portion relative to the anterior and posterior portions with arched or curved magnetic lines. The conical profile and curved magnetic lines of the encoder tracks are configured to compensate for joint rotational motion and maintain alignment and coupling between the read heads and the tracks. This maximizes measurement collection and measurement accuracy during a full range of motion of the knee joint. The shape, size and location of the encoder tracks can vary depending on the implant.

FIG. 4 shows details of a medial side of tibial insert 110. Tibial insert 110 includes a medial load sensor 132 in connection with medial read head 118 via a medial connector 134. Medial load sensor 132 is a load measuring sensor such as a strain gauge or piezoelectric sensor configured to measure loads or forces transmitted from medial read head 118 via medial connector 134. Medial connector 134 can be a rigid member such as a connecting rod to transmit loads from medial read head 118 to medial load sensor 132. As shown in FIG. 4, a portion of the medial side of femoral implant 102 directly contacts medial read head 118 to transmit loads (medial side loads), which is then measured by medial load sensor 132. Medial read head 118 is spring-loaded by a medial load spring 136 located below medial load sensor 132 to ensure contact between medial read head 118 and femoral implant 102. Similarly, a lateral side of tibial insert 110 includes a lateral load sensor, a lateral connector, and a lateral load spring. The lateral load sensor is configured to measure lateral loads between femoral implant 102 and tibial implant 104. Measured medial and lateral loads are transmitted via antenna 122 to an external source. Thus, knee joint implant 100 can simultaneously provide knee motion information (rotation, speed, flexion angle, etc.) and knee load (medial load, medial load center, lateral load, lateral load center, etc.) in real time to an external source.

Details of antenna 122 are shown in FIGS. 5A and 5B. Antenna 122 includes screw threads configured to be attached to tibial insert 110. Antenna 122 can include a coax interface to shield knee joint and improve transmission between knee joint implant 100 and the external source. A battery is located adjacent antenna 122 (not shown) to power knee joint implant 100. Antenna 122 can serve as a charging port via radio frequency (RF) or inductive coupling if a rechargeable battery is used. The location of battery and antenna 122 in tibial insert 110 allow for convenient access to remove and replace these components if necessary. Various other sensors such as a temperature sensor, pressure sensor, accelerometer, gyroscope, magnetometer, pH sensor, etc., can be included in knee joint implant 100 as more fully described below.

Figure 6:
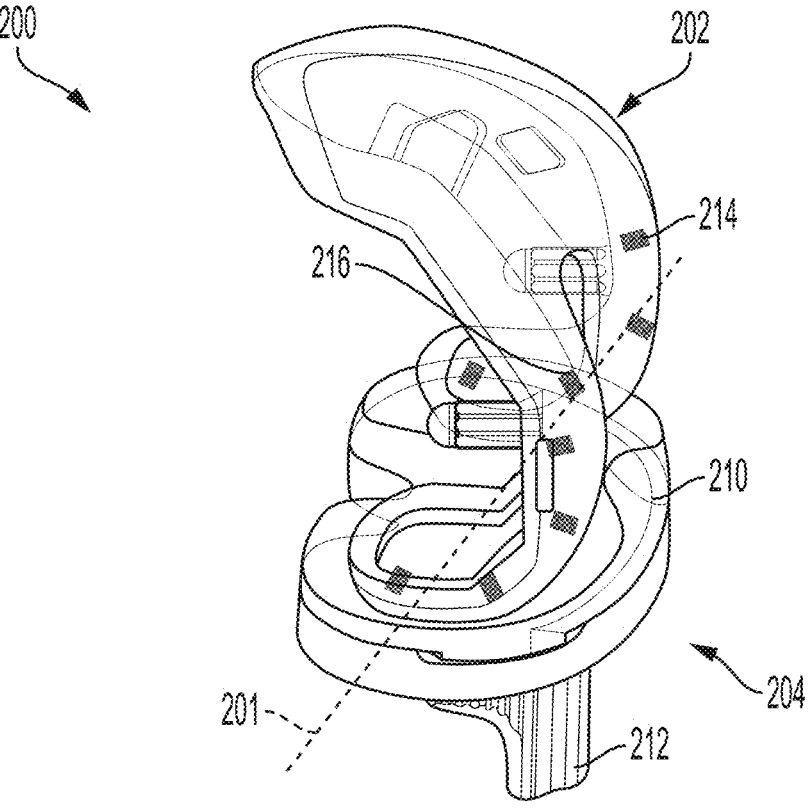
FIG. 6 is a perspective side view of a knee joint implant according to another embodiment of the present disclosure.
Figure 7:
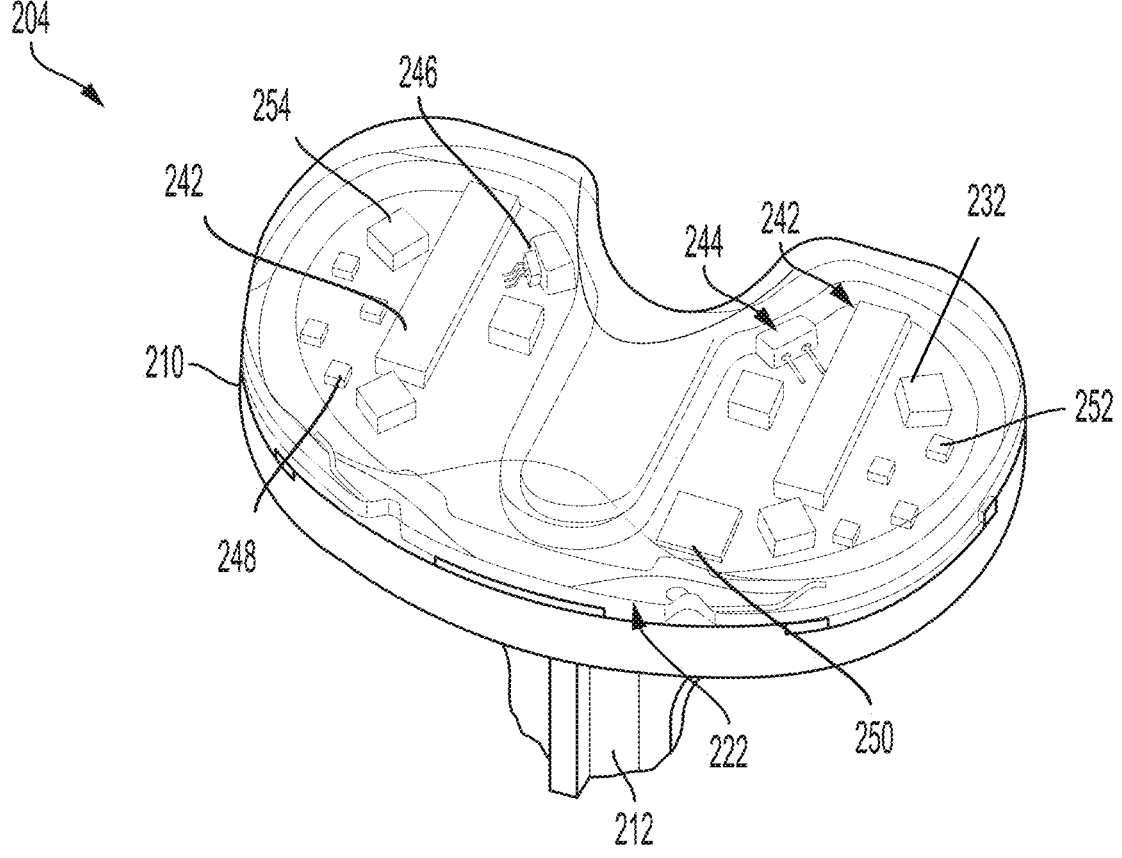
FIG. 7 is a perspective front view of a tibial implant of the knee joint implant of FIG. 6.
Figure 8:
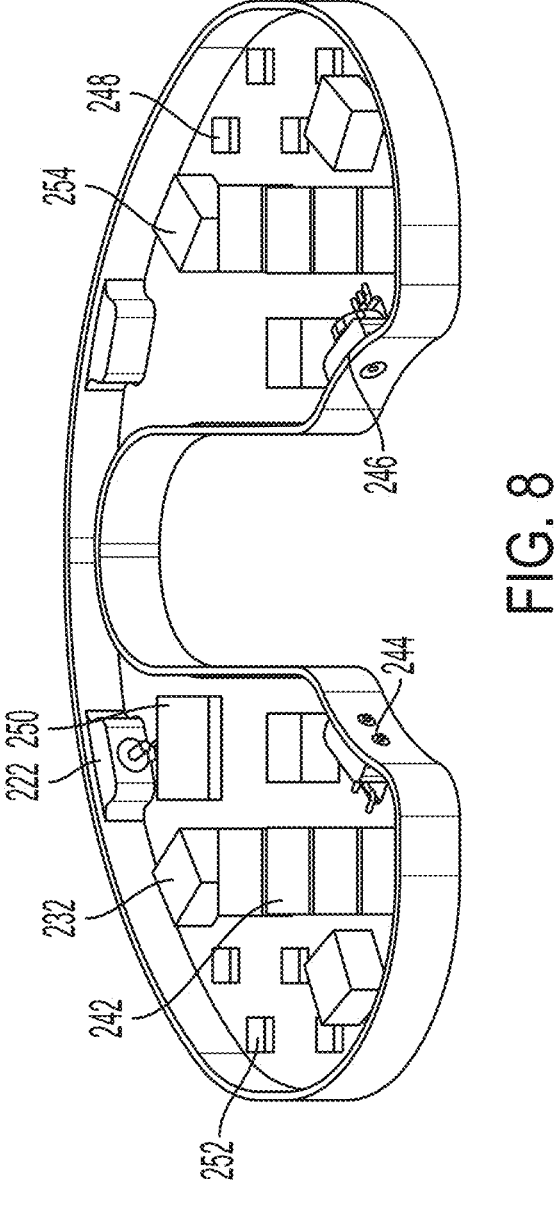
FIG. 8 is a partial perspective view of an insert of the tibial implant of FIG. 6

FIG. 6 is a perspective side view of a knee joint implant 200 according to another embodiment of the present disclosure. Knee joint implant 200 is similar to knee joint implant 100, and therefore like elements are referred to with similar numerals within the 200-series of numbers. For example, knee joint implant 200 includes a femoral implant 202, a tibial implant 204 with a tibial insert 210 and a tibial stem 212. However, knee joint implant 200 includes magnetic medial markers 214 and magnetic lateral markers 216 located at discrete locations along the medial and lateral sides of femoral implant 202, respectively.

Figure 9:
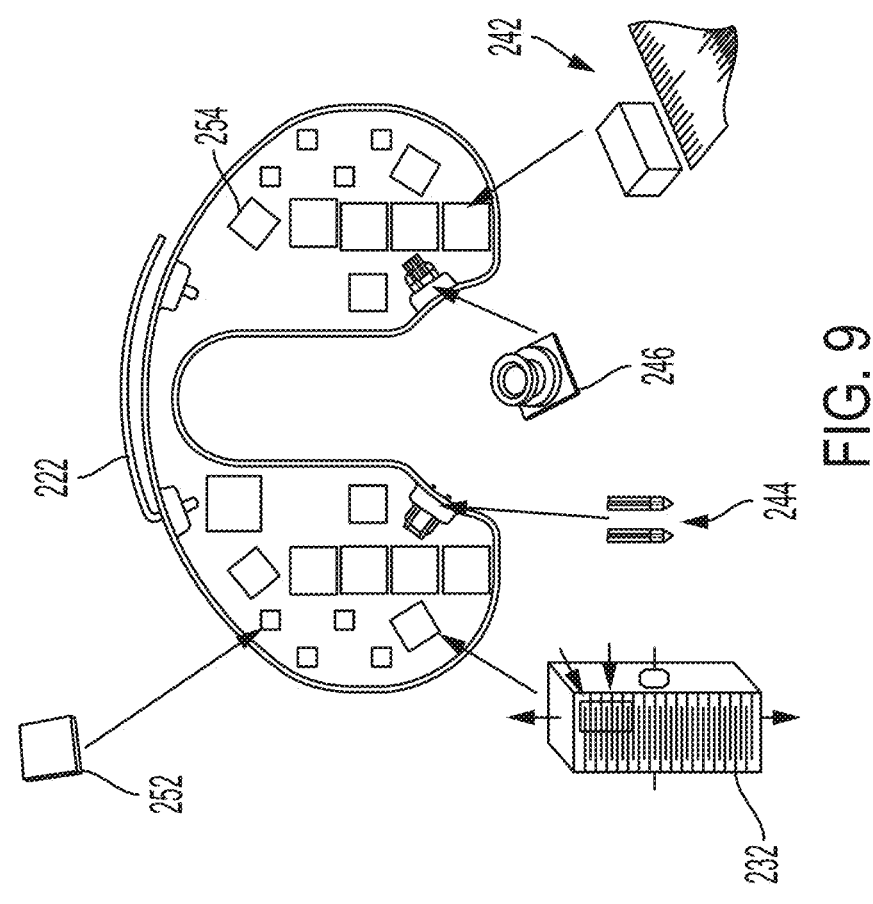
FIG. 9 is a partial top view of the insert of FIG. 8 showing details of various insert components.
Figure 9:

Details of tibial insert 210 are shown in FIGS. 7-11. Tibial insert 210 includes batteries 242 on both medial and lateral sides. Batteries 242 can be solid state batteries, lithium ion batteries, lithium carbon monofluoride batteries, lithium thionyl chloride batteries, lithium ion polymer batteries, etc. As best shown in FIG. 9, Hall sensor assemblies, with each assembly including at least one Hall sensor, are used as a medial marker reader 252 and a lateral marker reader 248 to read medial markers 214 and lateral markers 216, respectively. Each Hall sensor assembly can include multiple Hall sensors arranged in various configurations and orientations. For example, the Hall sensor assembly can include Hall sensors oriented in Cartesian coordinates. As the tibia rotates with reference to the femur during knee flexion and extension, medial markers 214 and lateral markers 216 move along medial marker reader 252 and lateral marker reader 248, respectively. This movement causes a change in magnetic flux density, which is detected by marker readers 252, 248, to measure knee joint implant 200 movement, rotation, speed and range of articulation, motion/activity, joint slip, and other motion related information. The magnetic-mechanic coupling of the marker readers with the markers allows for direct, instantaneous, and continuous measurements of these knee joint implant parameters without the need to process this information via an algorithm or other means. While eight Hall sensor assemblies (four on each side) are shown in this embodiment, other embodiments can have more than eight or less than eight Hall sensor assemblies positioned at various locations. The arrangement of marker readers and markers provide absolute positions of knee joint implant 200 supporting wake-up-and-read kernels. Thus, no inference of movement by data synchronization techniques is required to obtain absolute position data of knee joint implant 200. The number of medial markers 214 can be different from the number of lateral markers 216 to account for variation in signal fidelity between these sides. For example, seven magnetic markers can be provided on the medial side and only four magnet markers can be provided on the lateral side to improve signal fidelity and motion detection precision on the medial side.

As best shown in FIG. 9, three piezo stacks on the medial side serve as medial load sensors 232, and three piezo stacks on the lateral side serve as lateral load sensors 254. The staggered or non-linear arrangement of the three piezo stacks on the medial and lateral sides allow for net load measurements and identification of resultant load centers at the medial and lateral sides. Thus, knee joint implant 200 can simultaneously provide knee motion information (joint rotation, joint speed, joint flexion angle, joint slippage, etc.) and knee load (medial load, medial load center, lateral load, lateral load center, etc.) in real time to an external source. The piezo stacks are configured to generate power from the patient's motion by converting pressure on the piezo stacks to charge batteries 242 as more fully described below. Thus, knee joint implant 200 does not require external charging devices or replacement batteries for the active life of the implant.

Tibial insert 210 includes an infection or injury detection sensor 244. For example, the infection or injury detection can be a pH sensor configured to measured bacterial infection by measuring the alkalinity of synovial fluid to provide early detection of knee joint implant 200 related infection. A temperature and pressure sensor 246 is provided in tibial insert 210 to monitor knee joint implant 200 performance. For example, any increase in temperature and/or pressure may indicate implant-associated infection. Pressure sensor 246 is used to measure synovial fluid pressure in this embodiment. Temperature and/or pressure sensor 246 readings can provide early detection of knee joint implant 200 related infection. Thus, injury detection sensors 244 and 236 provide extended diagnostics with heuristics for first level assessment of infections or injury related to knee joint implant 200. An onboard processor 250 such as a micro-controller unit ("MCU") is used to read sensors 244 and 236 and process results for transmission to an external source. This data can be retrieved, processed, and transferred by the MCU via antenna 222 continuously, at predefined intervals, or when certain alkalinity, pressure, and/or temperature thresholds, or any combinations thereof, are detected.

Figures 10, 11:
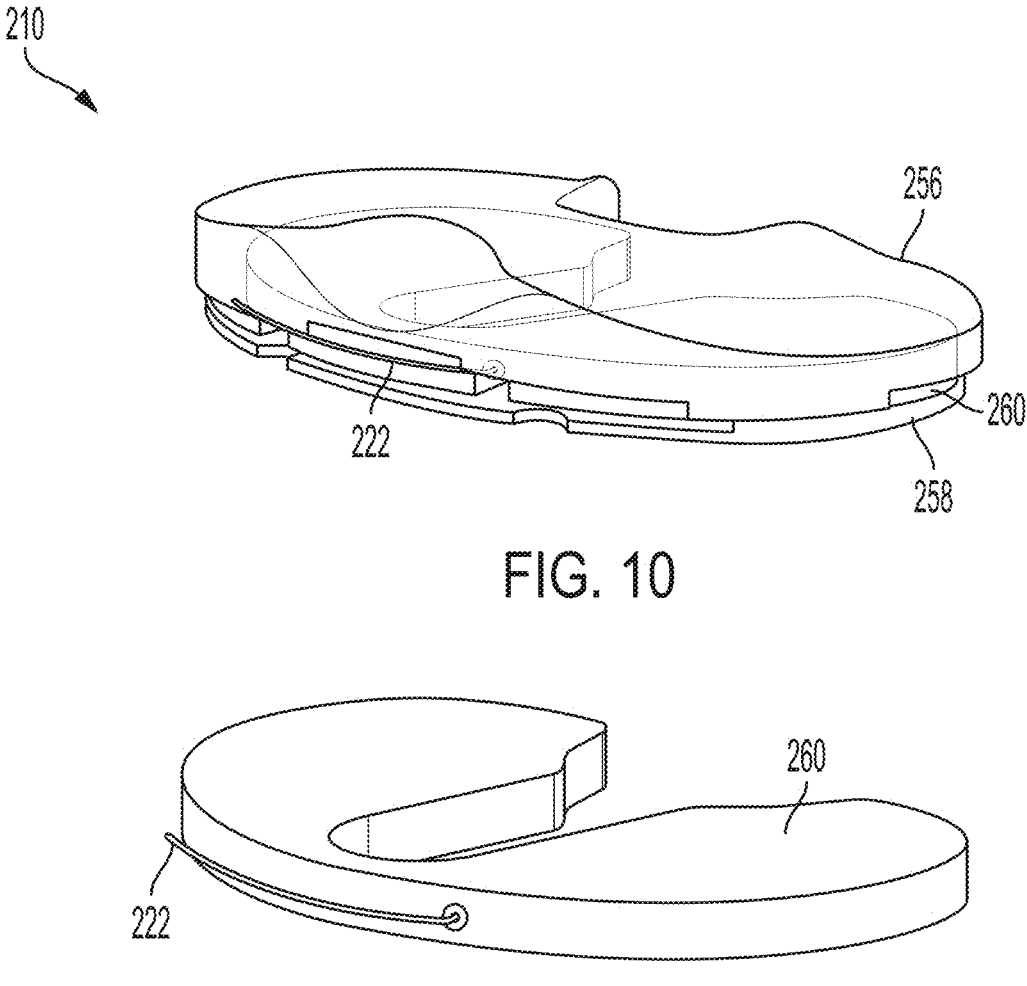
FIG. 10 is a perspective side view of the insert of the tibial implant of FIG. 7.
FIG. 11 is a perspective side view of a cover of the insert of FIG. 10.

The various sensors and electronic components of tibial insert 210 are contained within an upper cover 256 and a lower cover 258 as shown in FIG. 10. The upper and lower covers can be made from a polymer. Antenna 222 is located on an anterior portion of knee joint implant 200 to provide better line of site for transmitting data with less interference. The antenna is fixed inside the polymer covers to provide predictable inductance and capacitance. A cover 260 encloses the sensors and electronic components of tibial insert 210 as shown in FIG. 11. Cover 260 can be a hermetic cover to hermetically seal tibial insert 210. Cover 260 is preferably made of metal and provides radio frequency ("RF") shielding to the knee joint.

The modular design of knee joint implant 200 provides for convenient maintenance of its components. For example, an in-office or outpatient procedure will allow a surgeon to access the tibia below the patella (an area of minimal tissue allowing for fast recovery) to access component of knee joint implant 200. The electronic components and sensors of knee joint are modular and connector-less allowing for convenient replacement of tibial insert 210 or upgrades to same without impacting the femoral implant or the tibial stem.

Figure 12:
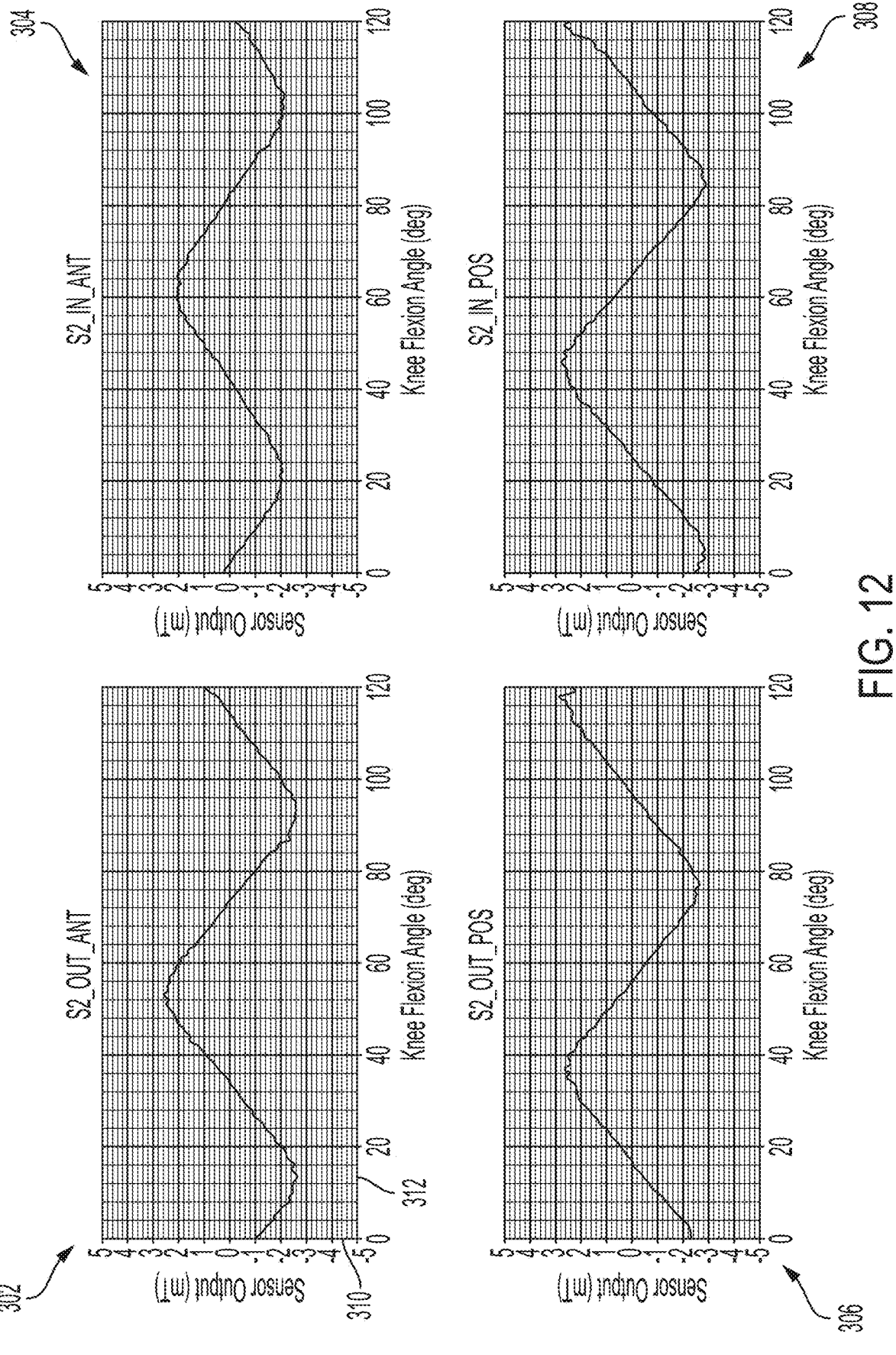
FIG. 12 are graphs showing magnetic flux density measurements of the implant sensors and knee flexion angles.

Graphs plotting magnetic flux density measurements 310 and knee flexion angles 312 are shown in FIG. 12. Magnetic flux density measurements 310 are generated from the magnetic-mechanic coupling of marker readers 248, 252 with the markers 214, 216 as more fully described above. Graphs 302 and 304 show magnetic flux density (mT) measurements from two Hall sensor assemblies (medial marker reader 252 or lateral marker reader 248) for a first range of motion of the knee joint. Similarly, graphs 306 and 308 show magnetic flux density (mT) measurements from two Hall sensors (medial marker reader 252 or lateral marker reader 248) for a second range of motion of the knee joint. The placement of magnetic markers 214, 216 on the femoral component create a sinusoidal magnetic flux density around femoral implant 202. As the femoral implant 202 rotates around an axis of rotation 201 shown in FIG. 6, the marker readers read sine and cosine waveforms. The magnitude of the sine and cosine waves are interpolated to a near linear knee flexion angle. Placing the individual magnetic markers of medial markers 214 and lateral markers 216 at different separation angles on each condyle of femoral implant 202 creates a phase shift in the measurements from one condyle to the next as the knee rotates. This phase shift can then be used to correct for any rollovers in the interpolated waveform. Thus, marker readers 248, 252 and markers 214, 216 serve as an absolute rotation sensor measuring knee flexion through a full range of motion of knee joint implant 200. In addition to the two Hall sensor assemblies on the lateral and medial side of tibial insert 210, the remaining Hall sensor assemblies of marker readers 248, 252 allow for 6-degrees of freedom movement measurements of knee joint implant 200 as more fully explained below. While an absolute magnetic encoder is disclosed in this embodiment, other embodiments can include a knee joint implant with an incremental magnetic encoder.

Figure 13:
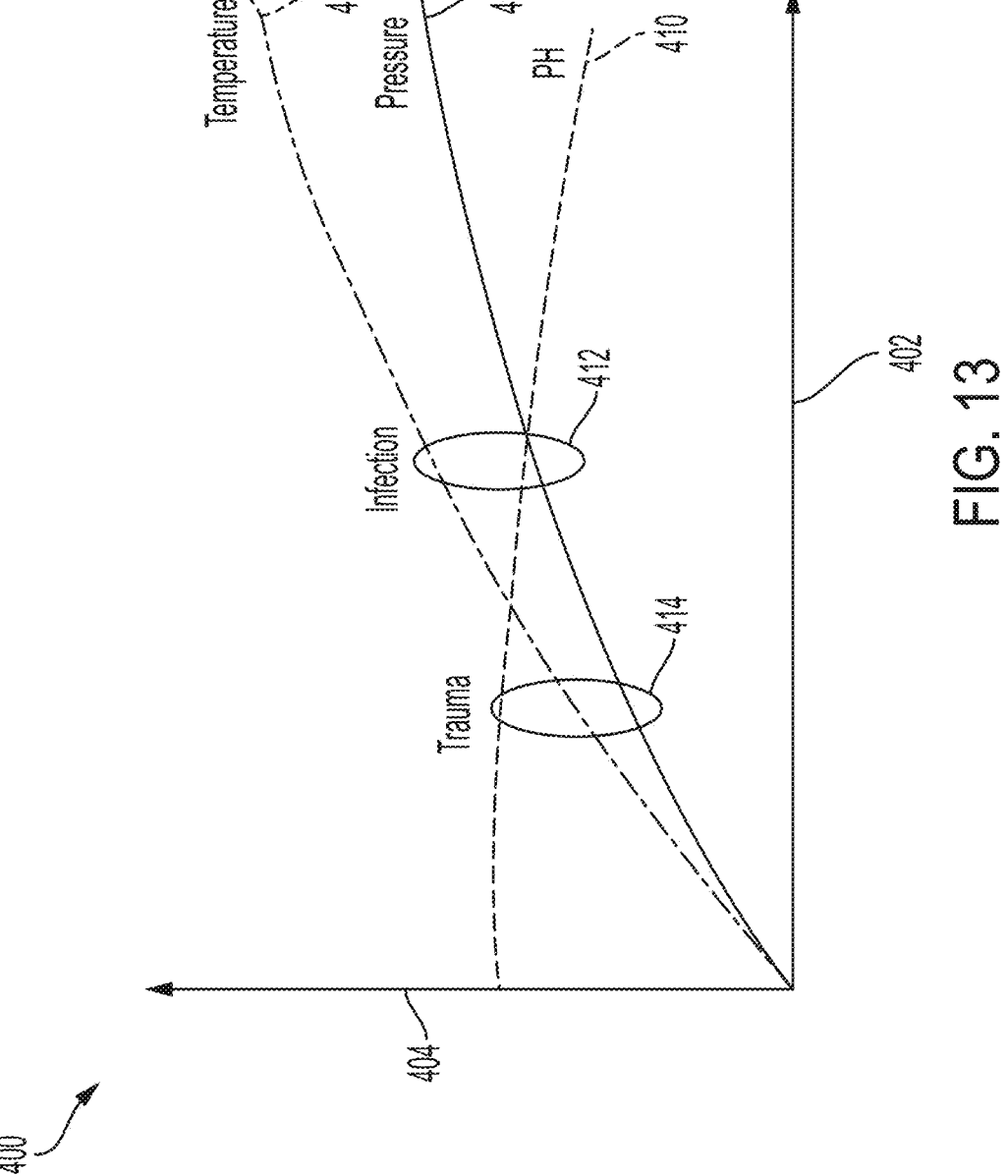
FIG. 13 is a graph showing various implant sensor readings of the knee joint implant of FIG. 6.
Figure 14:
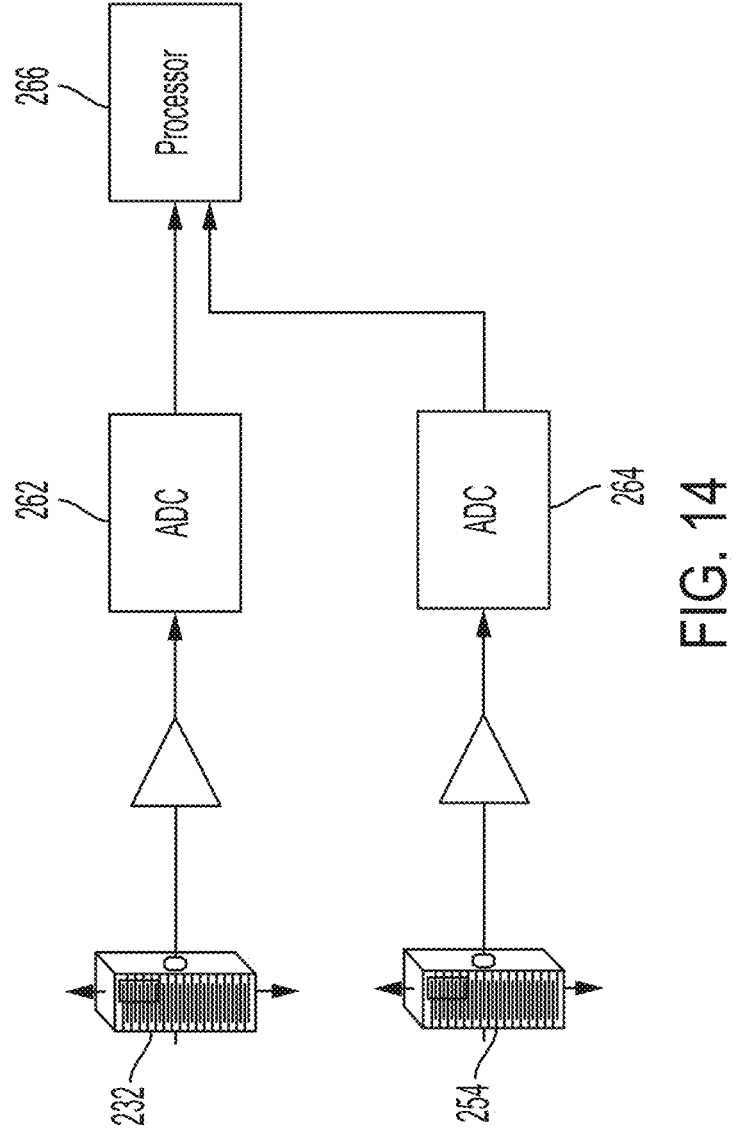
FIG. 14 is a schematic view of implant sensors of the knee joint implant of FIG. 6 in communication with a processor.

FIG. 13 is a graph showing various implant injury detection sensor readings 404 of knee joint implant 200 for early detection of knee joint implant related infection and/or failure. Pressure 408 and temperature 406 are measured using temperature and pressure sensor 246, and alkalinity 410 is measured using pH sensor 244 over time 402. As more fully explained above, alkalinity 410 measurements of joint synovial fluid can indicate bacterial infection to provide early detection of knee joint implant 200 related infection. Increase in pressure 408 and temperature 406 readings may indicate implant-associated infection. Variation or change in synovial fluid pressure 408 may indicate implant malfunction. In addition to predetermined absolute thresholds of the temperature, pressure and alkalinity readings indicating impending infection or implant failure, collective analysis of these readings can offer early detection warning ahead of the failure/infection thresholds. As shown in FIG. 14, a combination of temperature, pressure and alkalinity may indicate early detection of trauma 414 or infection 412. Thus, injury detection sensor readings provide extended diagnostics with heuristics for first level assessment of infections or injury related to knee joint implant 200.

In addition to the sensors described above, particularly with reference to knee joint implants 100 or 200, it is contemplated that the implant may include any type and any number of sensors useful for detecting signs of infection, inflammation, injury, etc. within the knee joint. For example, knee joint implant 200 may include an optical sensor capable of measuring the turbidity of the synovial fluid, and/or a blood sensor or analyzer capable of capturing data on pathogens present in the joint, which may allow for a more accurate treatment in the case of infection. Still further, the blood analyzer may include other functions such as glucose analysis, which may be useful for cases of diabetes in joint replacement.

As noted above, the data measured and gathered by the various sensors are read by the processor 250, such as an MCU, to process and transfer the measurements to an external source 5845 via the antenna 222. Processor 250 can send data in packets arranged by data types. For example, data packets containing Hall sensor position, IMU gyro, accelerometer, pH, pressure, temperature, etc. can be each transmitted under unique IDs. The type of data and frequency of measurement can be defined by a physician via a platform such as OrthoLogIQ, and sent over the air to the implant by a paired mobile device. During normal operation, the processor can be configured to run a particular task (such as a list of measurements assigned by a physician) at a defined rate (the frequency). The data can then be stored in local FRAM. The processor can then go to sleep until it is woken up by a timer interrupt to read, make readings, store data in memory, and return to sleep status as scheduled. Data upload can be during a defined period (primary) or on first chance (secondary). As shown in FIG. 86, the external source 5845 may be any device, such as one of the devices identified above, and is connected to a network such as a cloud network 5850. That is, the stream of data relayed from the processor 250 to the external source 5845 is fed into storage 5852 of the cloud 5850 and incorporated into a single or a plurality of neural network functions 5854, thus passing from a user 5840 to the cloud 5850 as shown in FIG. 86. For ease of description, all data obtained by a single implant in a respective user 5840 or patient will be referred to as a single set of data. Thus, when a first type of data is measured by the sensors and transmitted from the processor 250 to the external source 5845, the external source 5845 stores that data in the neural network 5854 of the cloud 5850. This process may then be repeated with a second user 5840 or patient, such that a second set of data is measured by the sensors of a knee joint implant 200 implanted in the knee joint of second user 5840 or patient, processed by the processor 250, and transmitted to the same external source 5845 by the antenna 222 of the second knee joint implant 200 to then be stored in the neural network 5854 of the cloud 5850. It is also contemplated that the second set of data may be conveyed to a second external source different from the first external source to which the first set of data was conveyed, however, all external sources may be connected to the same neural network 5854. This process may continue for additional users 5840, thereby storing and accumulating a plurality of data sets in the neural network 5854.

Some of the content stored in the neural network 5854 of the cloud 5850 includes, as described above, a set of data from each knee joint implant 200. Each set of data may include several types of data. That is, a first type of data may be obtained from a first type of sensor (e.g., temperature readings may be obtained from a temperature sensor, or pH readings may be obtained from a pH sensor). From such readings of each type and/or set of data, a clinician makes a diagnosis of the state of the knee joint or knee joint implant 200, either based on the set of data or on other factors (such as information provided by the patient), or a combination thereof. The clinician's diagnosis includes the determination of the knee joint or knee joint implant 200 being in any one of a variety of states, such as a healthy state, an infected state, an inflamed state, an injured state, or the like. The diagnosis may be manually entered into the external source 5845 by the clinician and thereby associated with the corresponding set of data in the neural network 5854.

After a first set of data from a first knee joint implant 200 in a first user 5840 is provided in the neural network 5854 with an associated diagnosis of the state of the knee joint implant 200 or knee joint, such a process may be repeated for a second set of data from a second knee joint implant 200 in a second user 5840, and may continue thereafter for any number of patients and sets of data which the cloud 5850 is capable of holding. As shown in FIG. 86, the neural network 5854 is operatively coupled to a software system 5860 which analyzes the various existing sets of data and associated diagnoses stored in the neural network 5854 to make inferences and estimations on the state of the knee joint and/or the knee joint implant 200. That is, the software system 5860 interprets each type of data within each set of data in view of the corresponding diagnoses of the respective implant which already exists within the neural network 5854 of the cloud 5850 to then comes to a conclusion about the state of another patient's knee joint implant 200. For example, based on existing sets of data stored in the neural network 5854, the software 5860 may define certain predetermined values with which the software 5860 will determine that if any of the types of data were to match such predetermined values, the software 5860 would deem a new patient's knee joint implant 200 to be in a certain state. In other examples, the software 5860 may define a range of predetermined values with which the software 5860 will determine that if any of the types of data were to fall outside of the predetermined range, the software 5860 would deem the new patient's knee joint implant 200 to be in a certain state, and alternatively may be deemed to be in a different state if the sensor measurements were to fall inside the predetermine range of values. For instance, the software 5860 might conclude that when the temperature of a knee joint implant 200 falls between X and Y, the knee joint is in a healthy state. However, when the measured temperature of a knee joint implant 200 falls outside of (e.g., above) the range between X and Y or above a threshold temperature, the knee joint may be determined to be in an inflamed state. As described above, the software 5860 takes into account a combination of the different types of data (e.g., temperature, pressure, pH, etc.) to conclude that a knee joint or a knee joint implant 200 is in a particular state. For instance, as shown by the graph in FIG. 13, the software system 5860 takes multiple types of data from multiple sensors and formulates a determination of the state of the joint or joint implant while factoring in each the measurements from each sensor.

Upon determining the state of a knee joint or a knee joint implant 200, the software 5860 may then initiate an alert or a warning, depending on the type of state it has determined the knee joint or implant 200 to be in. For example, if the knee joint or implant 200 is determined by the software 5860 to be in an infected state, the software 5860 initiates a warning notifying the clinician of the patient state, or notifying the client of the same through the client portal 5856. In some scenarios, such an alert is provided prior to the patient's feeling of pain or discomfort and therefore prior to a clinician's diagnosis would have occurred had the knee joint implant 200 not provided the alert. It is contemplated that the processor 250 of the implant 200 may communicate with the external source when prompted or activated by the patient (e.g., in the patient's home) or by the clinician (e.g., in the clinician's office). It is also contemplated that the processor 250 may communicate with the external source 5845 automatically when within a certain proximity of the external source 5845, allowing the software 5860 to issue a warning to the client portal 5856 even when unsuspected by the patient. In some examples, the client portal 5856 is accessible through the external source 5845. In further examples, if the software 5860 determines that the knee joint and the knee joint implant 200 are in a healthy state, the software 5860 may issue a notice to the patient/clinician indicating such condition (e.g., when the patient or clinician activates communication between the implant 200 and the external 5845 source), or the implant 200 may issue nothing at all.

The set of data of each patient implant 200 stored in the neural network 5854 of the cloud 5850 will remain in the neural network 5854 for as long as permitted by the clinician. However, it is also contemplated that the software 5860 may be capable of detecting an outlier set of data based on an associated diagnosis or manual input from the clinician, and the software 5860 may be capable of disregarding such outliers from its interpretations or removing such data from the neural network 5854 altogether. Generally, with each additional set of data from each patient implant 200 that is added to the neural network 5854, the software 5860 uses artificial intelligence to update its reference points and further refine its ability to detect the state a joint or joint implant 200. For example, with each addition of a new set of data from an implanted implant 200 determined to be in a healthy state, or a new set of data from an implanted implant 200 determined to be in an infected state, etc., the software 5860 may modify its predetermined values or the predetermined ranges of values which it uses to determine the state of a knee joint or implant 200, thereby further enhancing its accuracy of detection with each addition of new data. Therefore, the software 5860 is able to draw conclusions from an aggregate of data history stored within the neural network 5854, and the knowledge base of the neural network 5854 continuously improves over time.

In some examples, knee joint implant 200 employs a sensor redundancy system 6270 to filter the measured data using sensor redundancy, as shown in FIGS. 96A-96D, which helps to optimize and ensure accurate data measurements. In the example described herein, the plurality of redundant sensors is detailed with respect to the Hall sensors included in knee joint implant 200, however, it is contemplated that this concept may apply to any other type of sensor included in knee joint implant 200, such as temperature sensors, pressure sensors, accelerometers, gyroscopes, magnetometers, pH sensors, etc., specifically when more than one of the same type of sensor is included in the implant. Although knee joint implant 200 is described above as including eight Hall sensors assemblies, the example described herein with respect to FIGS. 96A-96D includes six Hall sensors, labeled sequentially as HS1-HS6. Each Hall sensor HS1-HS6 detects at least a positioning coordinate in each of an X-direction, a Y-direction, and a Z-direction as shown in FIG. 96A, which may be used to sense movement, rotation, speed and range of articulation, motion/ activity, joint slip, and other motion related information as described above. Each Hall sensor is operatively and electrically coupled to a processor or microcontroller unit ("MCU") 6272 so that the data obtained by each of the sensors can be processed into information to be output by the knee joint implant 200. The data read from each Hall sensor is marked with a poison value and arranged into data packets, or packetized, by the MCU 6272 which can be later interpreted as described below in more detail.

The MCU 6272, disposed within the knee joint implant 200, is operatively coupled to a channel detector 6274, e.g., via a wireless connection such as Bluetooth, which is able to read the data processed by the MCU 6272 from each Hall sensor HS1-HS6. In the illustrated example, the MCU 6272 is configured to communicate with an external source disposed outside of the knee joint implant 200 via, for example, an antenna disposed within the implant. The channel detector 6274 may be either included in or coupled to the external source. In some situations, all of the Hall sensors may measure and record consistent and generally accurate data, and the data from all six sensors can be used to determine the positioning and movement of knee joint implant 200. However, in other situations, any one or a plurality of the Hall sensors HS1-HS6 may produce inaccurate data for any reason, such as electrical noise. For example, in FIGS. 96A-96C, HS3 is outputting flawed or excludable data which preferably would not be considered in the collective positioning data gathered by the Hall sensors. Thus, the excludable data recorded by Hall sensor HS3 is tagged as having inaccurate data that should not be considered (as indicated in FIG. 96B wherein the "X-Y-Z" coordinates for HS3 are replaced with "F-F-F.") As shown in FIG. 96D, the channel detector 6274 is operatively coupled to, e.g., via a wireless connection such as Bluetooth, and can automatically engage a neural network 6276 including various channels to process only the valid channel data suppressing the data tagged for exclusion. The measurements from each Hall sensor are each fed into a corresponding channel That is, the data from HS1 is associated with channel 1, HS2 with channel 2, HS3 with channel 3, HS4 with channel 4, HS5 with channel 5, and HS6 with channel 6. The channel detector 6274 can be external to knee joint implant 200, and may be included in, for example, the external source communicating with the implant. The channel detector may communicate with the neural network 6276, which may be configured to communicate with various implants or other devices to accumulate and store data points from such devices. Thus, the MCU 6272 may compare and analyze only the data received from the Hall sensors of knee joint implant 200 to determine that one of the sensors has provided flawed data, or alternatively, the MCU 6272 may compare the data received from the Hall sensors with data contained and accumulated within the neural network to identify a flawed measurement.

In the illustrated example, HS3 is passing inaccurate data through channel 3. After the channel outputting inaccurate data is affirmatively identified and tagged, e.g., channel 3, the channel is automatically removed from consideration by the detector 6274 based on its data tag so that only the remaining channels outputting accurate data are selected by the detector 6274 for consideration of their respective data, which in this example includes channel 1, channel 2, channel 4, channel 5 and channel 6. In other words, the detector 6274 chooses the five remaining channels having accurate measurements to compile and output the positioning information collectively detected by the properly functioning Hall sensors.

In alternative embodiments, the channel detector may be included in the implant itself. The implant may have its own internal neural network in which it collects and accumulates data from the implant over time, or in which data can be uploaded and stored within the implant's internal neural network to allow the implant itself to detect and tag inaccurate data measurements.

The sensor redundancy system 6270 may be activated automatically, e.g., in accordance with a timed schedule or when brought into proximity with an external source. Alternatively, the sensor redundancy system 6270 may be activated manually by a user, such as the patient or a clinician. In either example, the sensor redundancy system 6270 may be optimized for power savings such that the system is powered off when not in use.

It should be understood that the exclusion of inaccurate data using sensor redundancy system 6270 is not limited to the example described herein in which the knee joint implant 200 includes six Hall sensors and one of the Hall sensors produces inaccurate data. Sensor redundancy may be applied in any implant having at least two Hall sensors, and preferably more than two sensors to further ensure the accurate measurements and the inaccurate measurements are correctly identified. For instance, knee joint implant 200 may indeed have eight Hall sensors gathering data relating to the movement of the knee joint, wherein any one or more of those eight sensors may malfunction at any given moment, which will then be tagged by the processor, detected and excluded by the channel detector 6274. It is contemplated that more than one sensor among the group of sensors may experience noise or produce unusable data, and that more than one channel can be identified and excluded from the selection of data. In such examples, a greater number of sensors may be advantageous so that inaccurate data can be confidently identified in the one, two, etc. malfunctioning sensors while still having a majority of the sensors, e.g., six or seven, still functioning properly and collecting useful positioning data. That is, incorporation of a greater number of sensors may help the MCU or the detector identify which channels have inaccurate data and should be excluded.

It should also be understood that the Hall sensors in the illustrated example may be replaced with any other type of sensor, and the same operations as described above may be performed to filter out inaccurate data from a plurality of such sensors. It should also be understood that the sensor redundancy system is not limited to use in knee joint implant 200, but may be used in any type of implant, including alternative implants described throughout this application, or outside the context of implants for measuring any type of data.

The sensor redundancy system 6270 provides for resilient operation of the knee joint implant's ability to measure and output data about the knee joint and/or the implant. That is, by identifying and removing improper data, the sensor redundancy system 6270 reinforces the implant's ability to output data either automatically or upon request, and also reduces the likelihood of the implant from outputting incorrect or misleading data, e.g., a situation in which a sensor is interrupted or otherwise recording wrongly affected data, and such data would have been factored into the movement or positioning information provided by the implant. Thus, the system provides redundancy and resiliency to ensure functioning operations in the face of component failure.

Additionally, the system reduces processing requirements and improves efficiency by removal of the channel That is, once a channel is removed, the data processing associated with that channel decreases, thereby reducing the processing requirement.

In another embodiment, the sensor redundancy system can be used to control engagement/activity of the plurality of sensors manually or automatically. For example, the sensor redundancy system can deactivate Hall sensors by turning off the device for power savings, perform individual access tests, manage responses in noisy environments, etc. The sensor redundancy system can be used to target and use only specific sensors or rely more on specific sensors instead of using/relying on all sensors for data collection in particular applications such as characterizing movement with specific points of interest.

Figure 15:
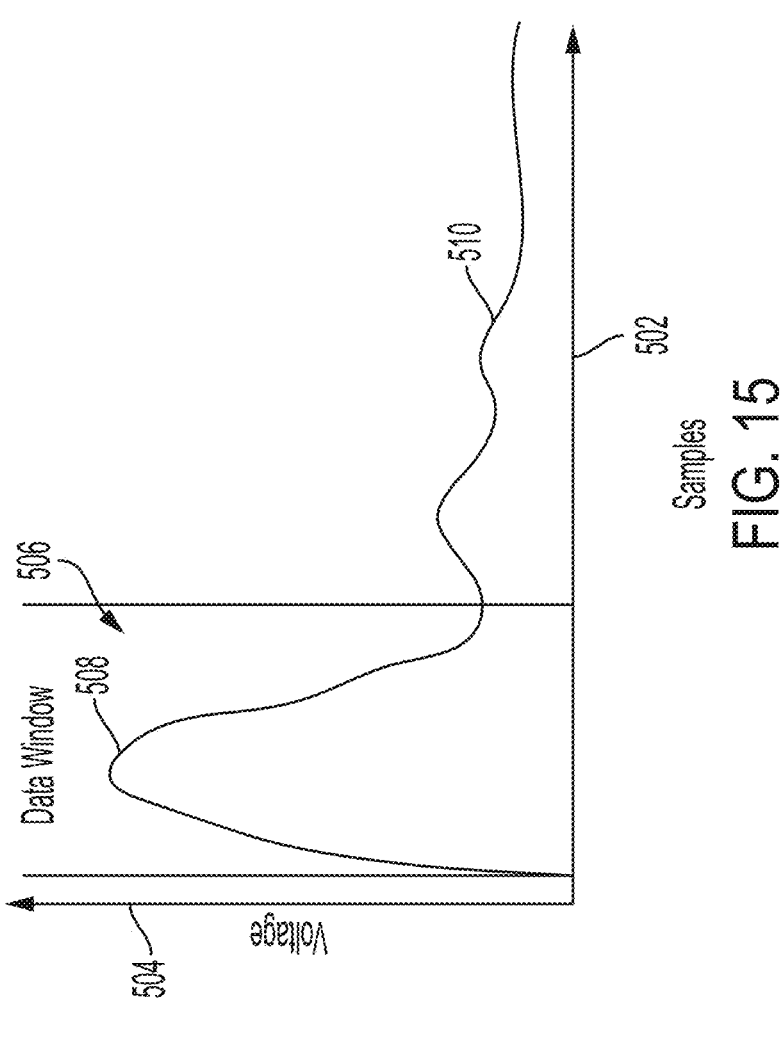
FIG. 15 is a graph showing voltage measurements of the implant sensors.
Figure 15:

FIG. 14 is a schematic view of piezo stacks of medial load sensors 232 and lateral load sensor 254 in communication with a processor 266. Analog impulses generated by the piezo stacks when subjected to loading are converted to continuous digital signals via analog-to-digital converters 262 and 264 as shown in FIG. 14. The continuous digital signals (voltage) 508 can be serially loaded into a shift register and measured as shown in a graph 500 of FIG. 15. A sampling window 506 is selected to identify a peak reading 508 to detect knee joint motion. For continuous loading case, such as when a patient is standing, additional sensors such as an inertial measurement unit ("IMU") located in the tibial insert or other locations on knee joint implant 200 can be used to detect or confirm knee joint position. Load data from piezo stacks and IMU measurements can be used to create load and motion profiles for patient-specific or patient-independent analyses.

Figure 16:
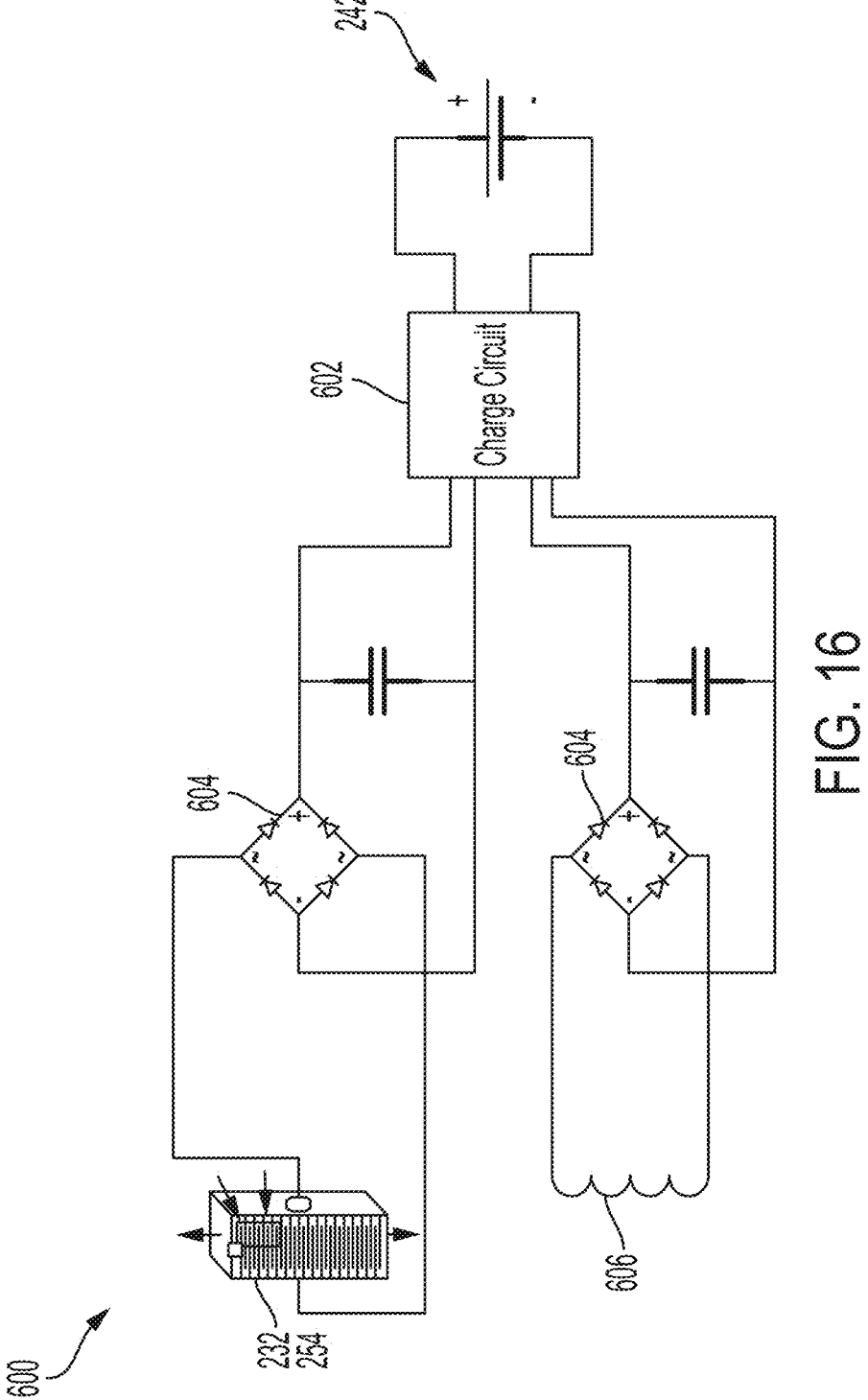
FIG. 16 is a schematic view of a charging circuit for the knee joint implant of FIG. 6.
Figures 17A, 17B:
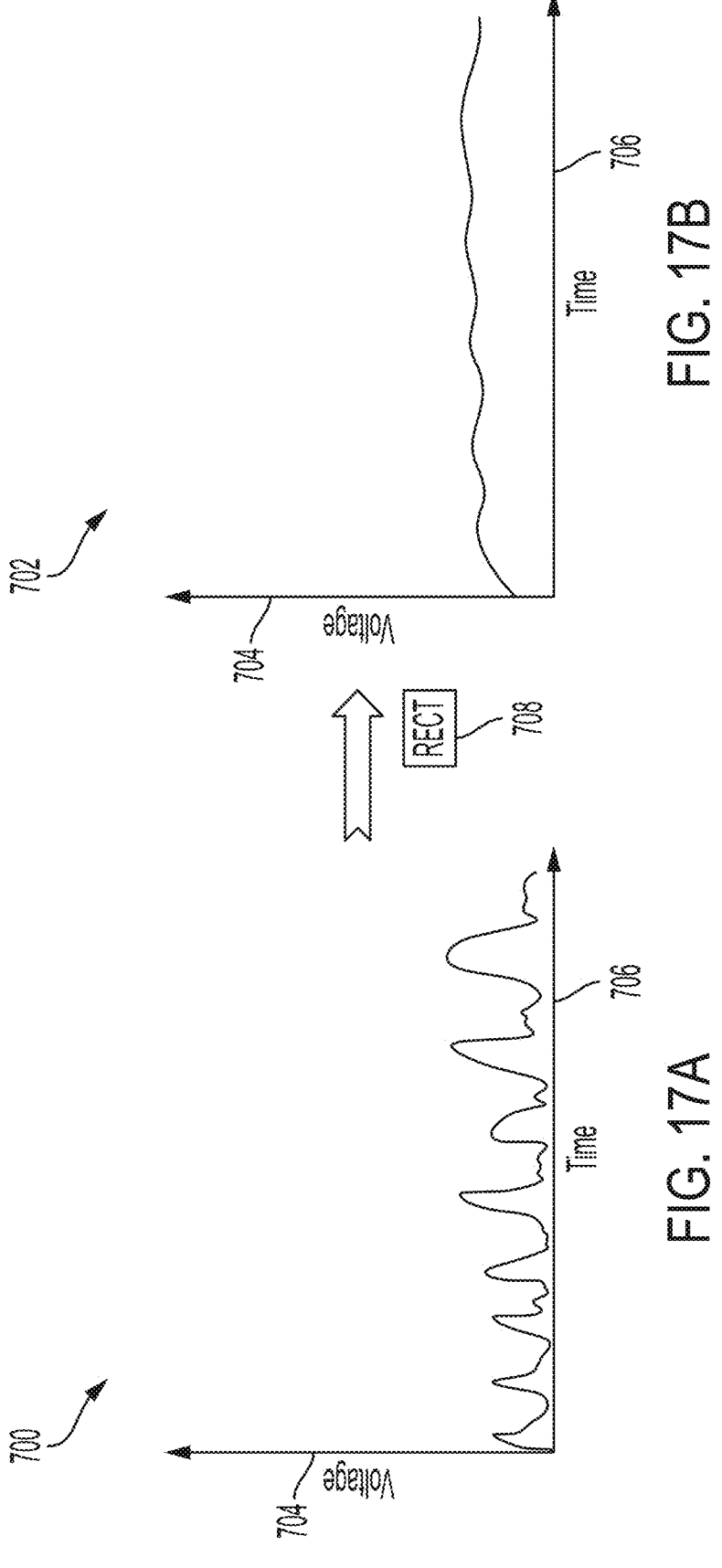
FIG. 17A is a graph showing measured voltage of the implant sensors.
FIG. 17B is a graph showing rectified voltage of the implant sensors.

FIG. 16 is a schematic view of a charging circuit 600 for charging battery 242 of knee joint implant 200. The charging circuit includes a charge circuit 602 connected to a charging coil 606 and piezo stacks of medial load sensors 232 and lateral load sensors 254 via bridge rectifier 604. Charging circuit is configured to direct charge to battery 242 utilizing inputs from one or more piezo stacks from the medial or lateral load sensors. This allows for singular or combined charging using individual or multiple piezo stacks. A minimum voltage output threshold of the piezo stacks can be predetermined to initiate battery charging. For example, when a patient is asleep, low piezo stack pulses will not be used to charge battery 242. Raw piezo stack pulses (voltage 704) as shown in a graph 700 of FIG. 17 over time 706 are rectified by a voltage rectifier 708 to produce a rectified and smoothed voltage output (voltage 704) shown in a graph 702 of FIG. 17B. The rectified and smoothed voltage output from the piezo stacks is used to charge battery 242. Thus, power harvesting from motion of knee joint implant 200 is achieved by using the pulses generated by the piezo stacks.

Figure 18:
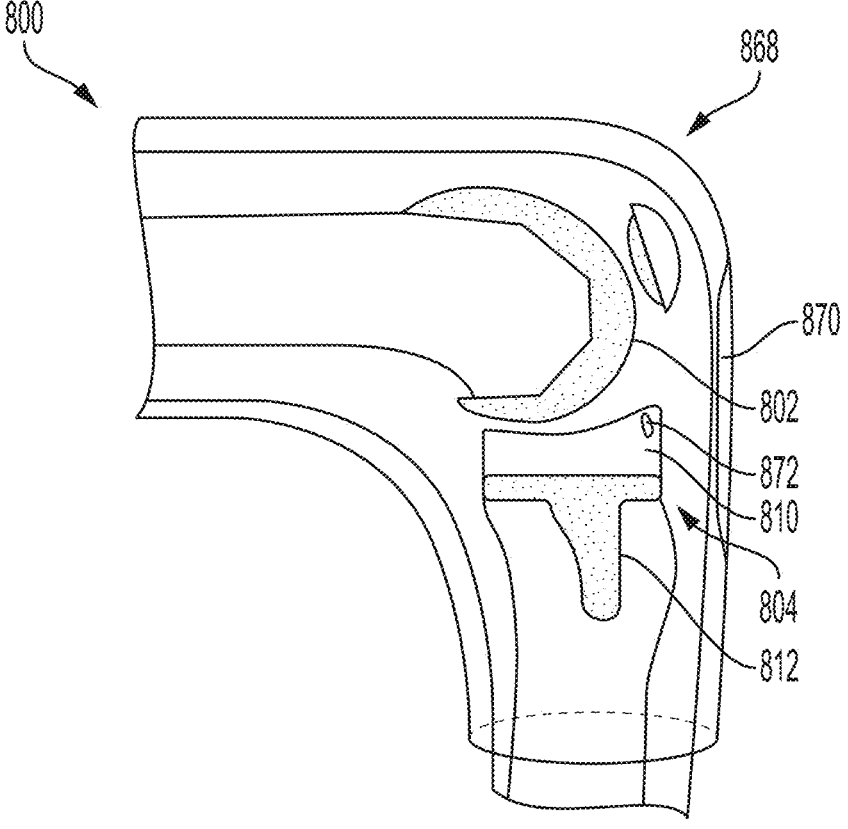
FIG. 18 is a schematic view of a knee joint implant with a charging sleeve according to an embodiment of the present disclosure.

FIG. 18 is a schematic view of a knee joint implant 800 according to another embodiment of the present disclosure. Knee joint implant 800 is similar to knee joint implant 200, and therefore like elements are referred to with similar numerals within the 800-series of numbers. For example, knee joint implant 800 includes a femoral implant 802, a tibial implant 804 with a tibial stem 812 and a tibial insert 810. However, knee joint implant 800 includes a chargeable implant coil 872 located in tibial insert 810 which can be charged by an external coil 870 contained in an external sleeve 868 as shown in FIG. 18.

Figure 19:
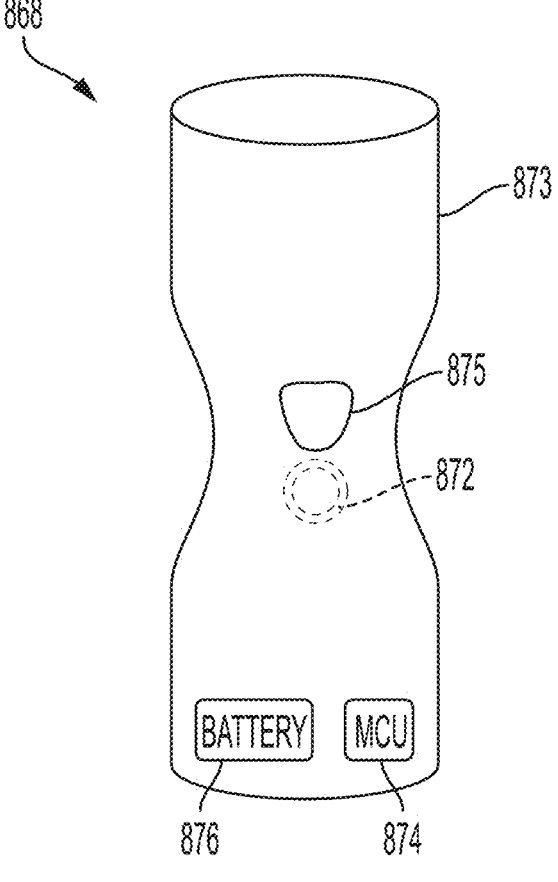
FIG. 19 is a front view of the charging sleeve of the knee joint implant of FIG. 17.

External sleeve 868 shown in FIG. 19 includes an outer body 873 made of stretchable fabric or other material. Outer body 873 is configured to be a ready-to-wear pull-on knee sleeve which a patiently can conveniently put on and remove. A kneecap indicator 875 allows the patient to conveniently align sleeve 868 with knee joint implant 800 for proper placement of external coil 870 with reference to implant coil 872 for charging. As shown in FIG. 18, when a patient aligns external sleeve 868 using kneecap indicator 875 and assumes a flexion position, external coil 870 is adjacent to implant coil 872 for proper charging. External sleeve 868 includes a battery 876 and a microcontroller 874 as shown in FIG. 19. Battery 876, which can be conveniently replaced, provides power to external coil 870. In another embodiment, external coil 870 may be charged by an external source not located on sleeve 868.

Figure 21:
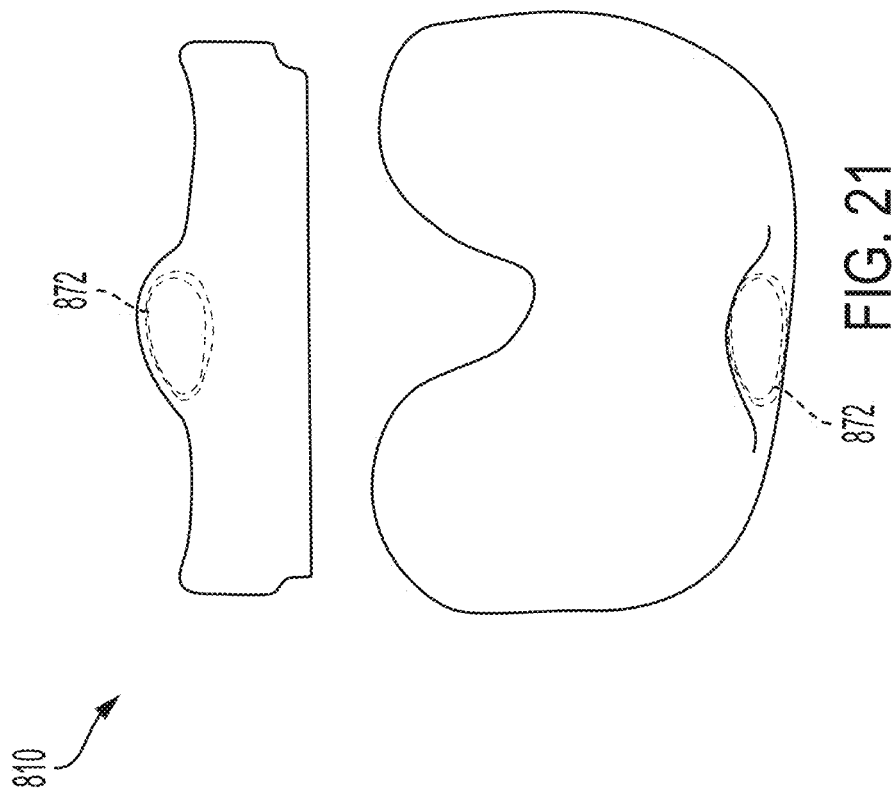
FIG. 21 shows top and front views of the insert of FIG. 19.
Figure 20:
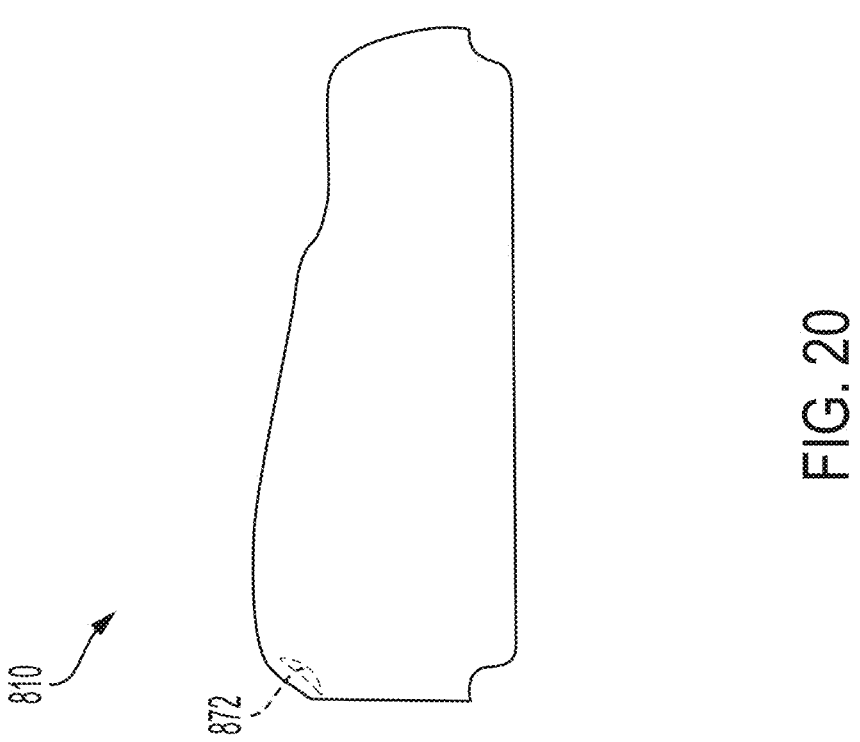
FIG. 20 is a side view of an insert of the knee joint implant of FIG. 17.

FIG. 20 shows a side view of tibial insert 810 of knee joint implant 800. Tibial insert 810 is made of a polymer or other suitable to facilitate charging of implant coil 872. Implant coil 872 is located within tibial insert 810 at an indent or depression at a proximal-anterior corner of the tibial insert as show in FIG. 20 and FIG. 21 (top and front views of tibial implant 810). The proximal-anterior location of implant coil 872 maximizes access to external coil 870 for efficient and convenient charging.

Figure 22B:
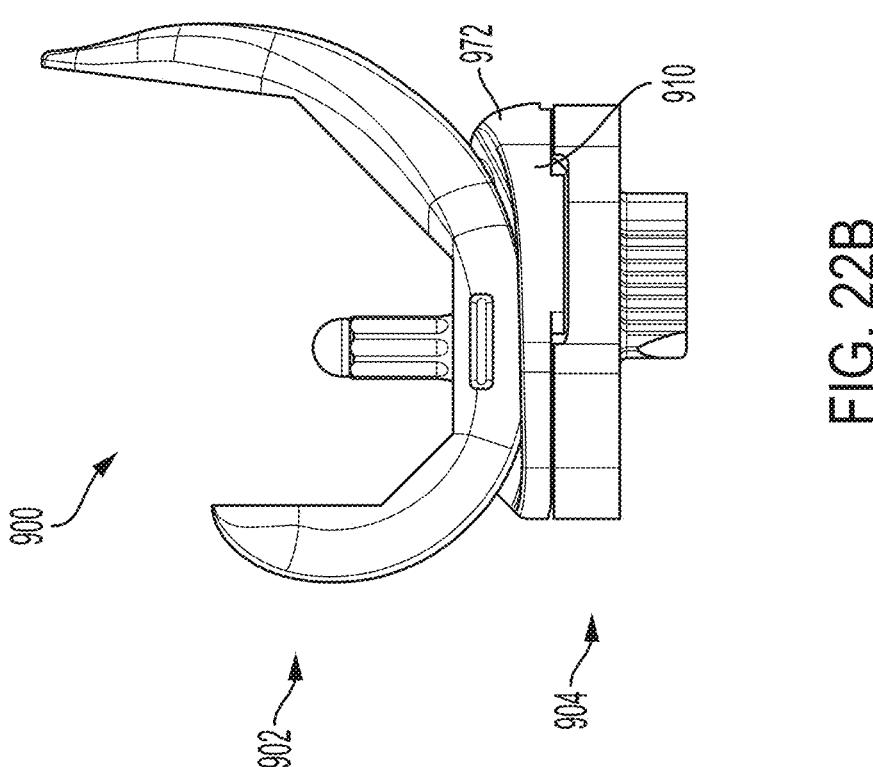
FIG. 22B is a side view of the knee joint implant of FIG. 22A.
Figure 22A:
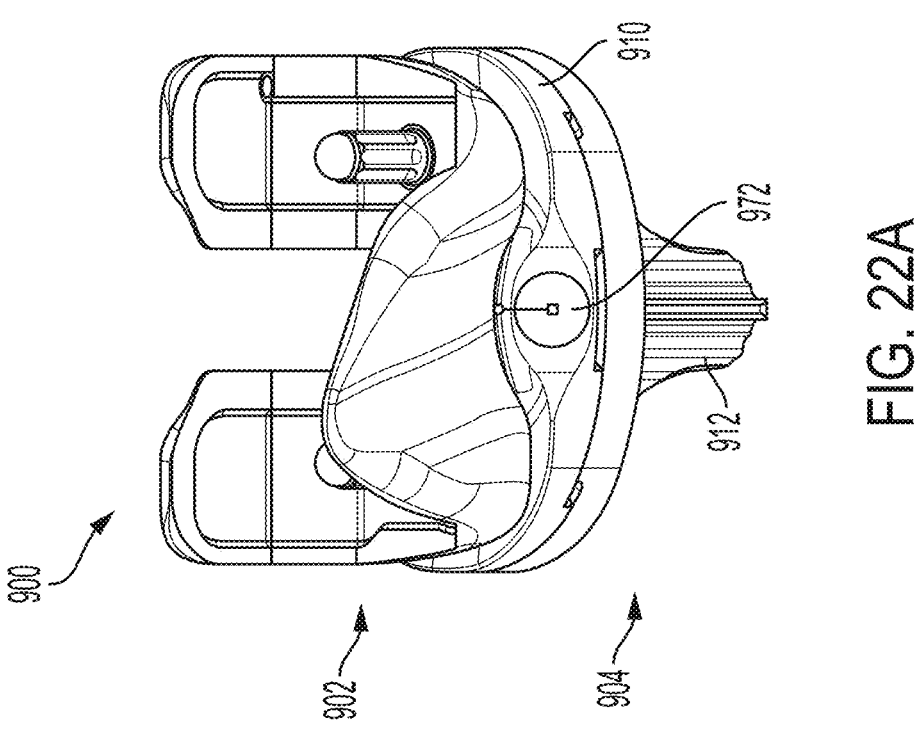
FIG. 22A is front view of a knee joint implant according to another embodiment of the present disclosure.

FIGS. 22A and 22B show a knee joint implant 900 according to another embodiment of the present disclosure. Knee joint implant 900 is similar to knee joint implant 800, and therefore like elements are referred to with similar numerals within the 900-series of numbers. For example, knee joint implant 900 includes a femoral implant 902, a tibial implant 904 with a tibial stem 912 and a tibial insert 910. However, knee joint implant 900 includes a chargeable implant coil 972 located at anterior end of tibial insert 910 which can be charged by an external coil 970 (not shown). An external sleeve as described with reference knee joint implant 900, or another charging mechanism can be used to conveniently charge implant coil 972.

Figure 23B:
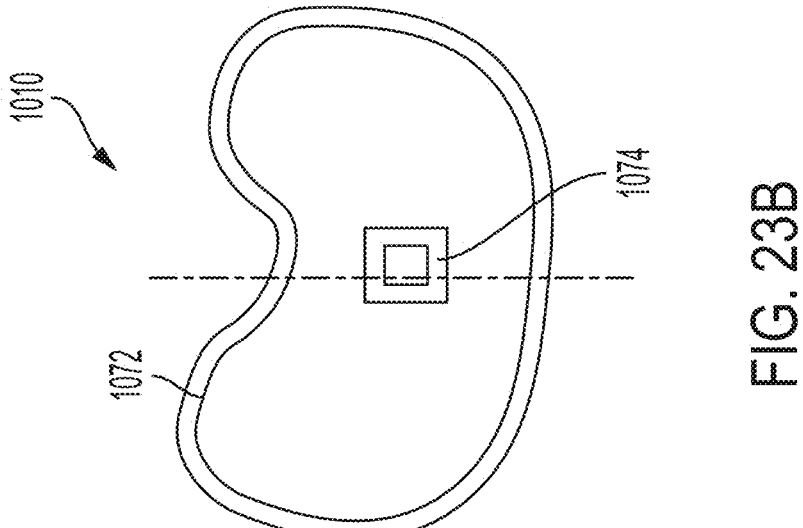
FIG. 23B is a top view of an insert of the tibial implant of FIG. 22A.
Figure 23A:
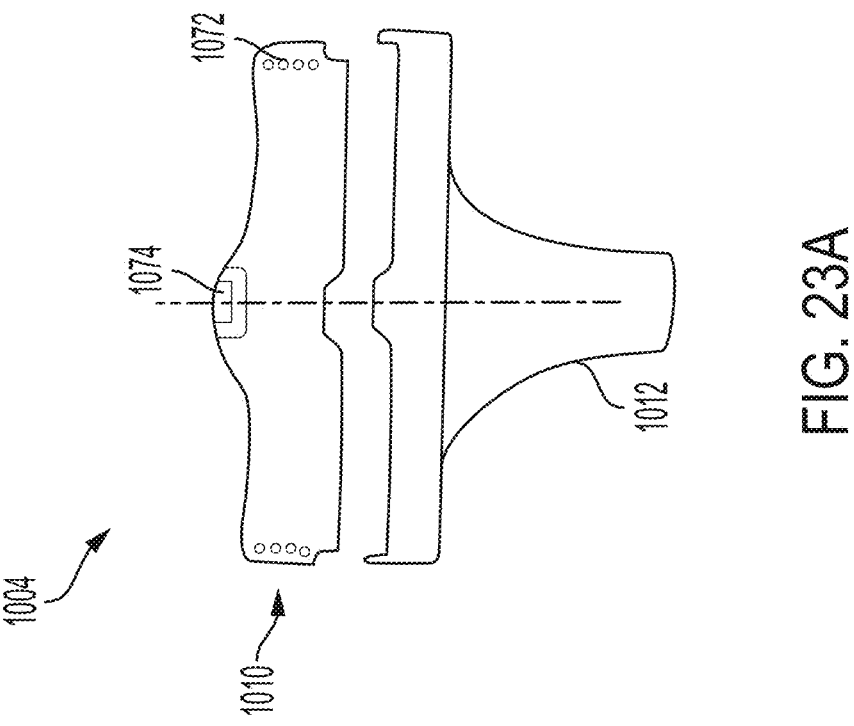
FIG. 23A is a front view of a tibial implant according to another embodiment of the present disclosure.

FIG. 23A is a front view of a tibial implant 1004 according to an embodiment of the present disclosure. Tibial implant 1004 is similar to tibial implant 204, and therefore like elements are referred to with similar numerals within the 1000-series of numbers. For example, tibial implant 1004 includes a tibial stem 1012 and a tibial insert 1010. However, tibial insert 1010 includes a charging coil 1072 located around a periphery of the tibial insert 1010 as shown in FIG. 23B. A spectroscopy sensor 1074 in tibial insert 1010 serves as an infection detection sensor for tibial implant 1004. Spectroscopy sensor 1074 is configured to identify the onset of biofilm on tibial implant (or a corresponding femoral implant) to provide early detection of implant related infection.

Figure 24B:
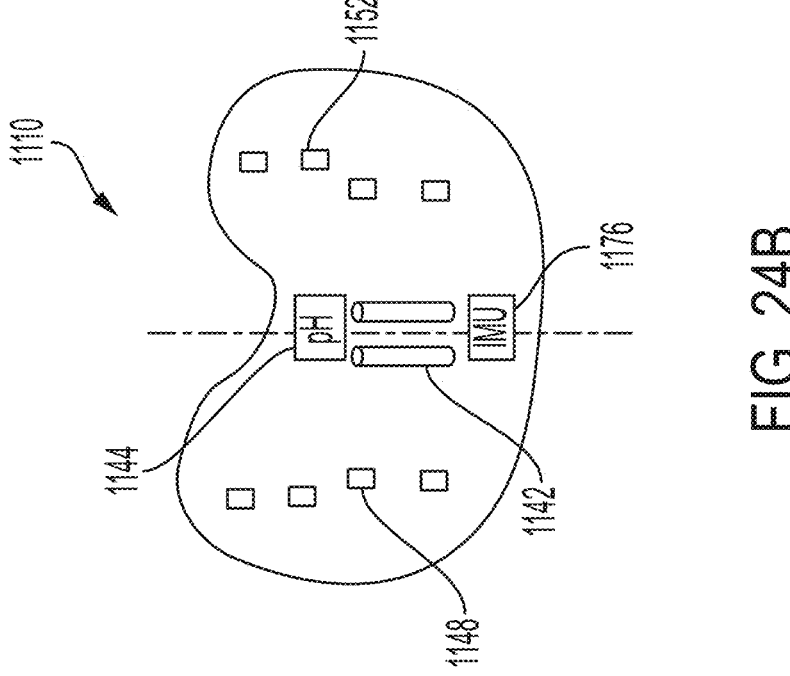
FIG. 24B is a top view of an insert of the tibial implant of FIG. 24A.
Figure 24A:
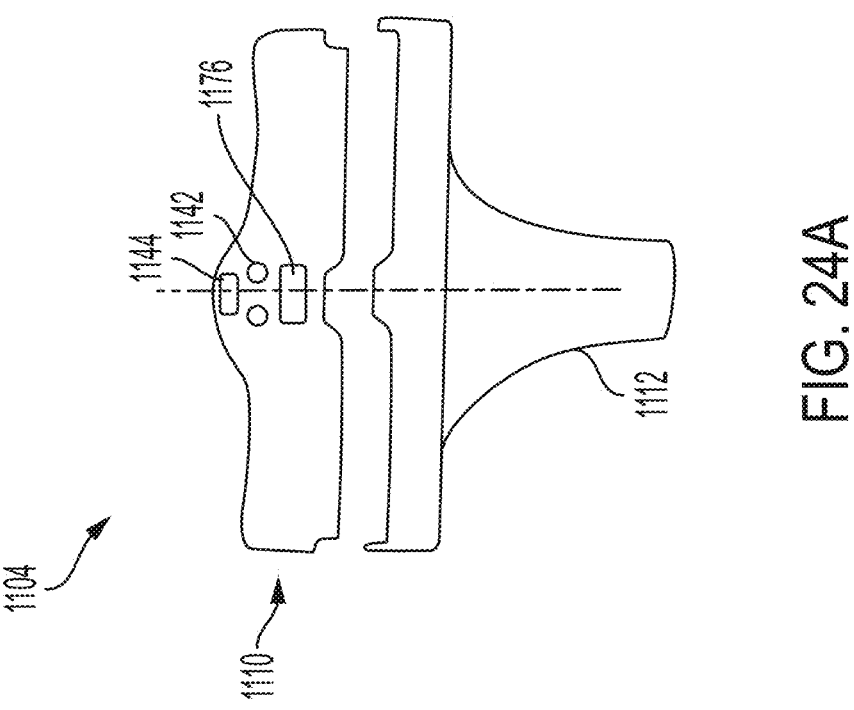
FIG. 24A is a front view of a tibial implant according to another embodiment of the present disclosure.

FIG. 24A is a front view of a tibial implant 1104 according to an embodiment of the present disclosure. Tibial implant 1104 is similar to tibial implant 204, and therefore like elements are referred to with similar numerals within the 1100-series of numbers. For example, tibial implant 1104 includes a tibial stem 1112 and a tibial insert 1110. However, tibial insert 1110 includes an IMU 1176 and five Hall sensor assemblies for each of the medial and lateral marker readers. The arrangement of the Hall sensor assemblies differ from tibial insert 210. Sensor data from IMU 1176 provides additional knee implant joint movement data as more fully explained above. For example, IMU 1176 can detect or confirm knee joint position during continuous loading positions of a patient such as standing. IMU data can reveal, or support measurements related to gait characteristics, stride, speed, etc., of a patient. pH sensor 1144 of tibial insert 1110 is located adjacent to a proximal face of the tibial insert at a central location as shown in FIG. 24B. All sensors of tibial implant 1104 are powered by batteries located in tibial insert 1110.

Figure 25B:
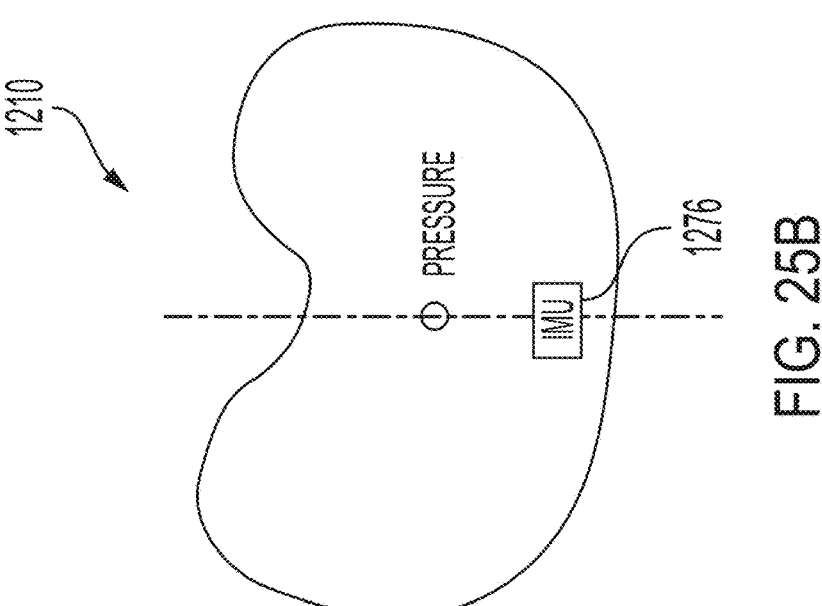
FIG. 25B is a top view of an insert of the tibial implant of FIG. 25A.
Figure 25A:
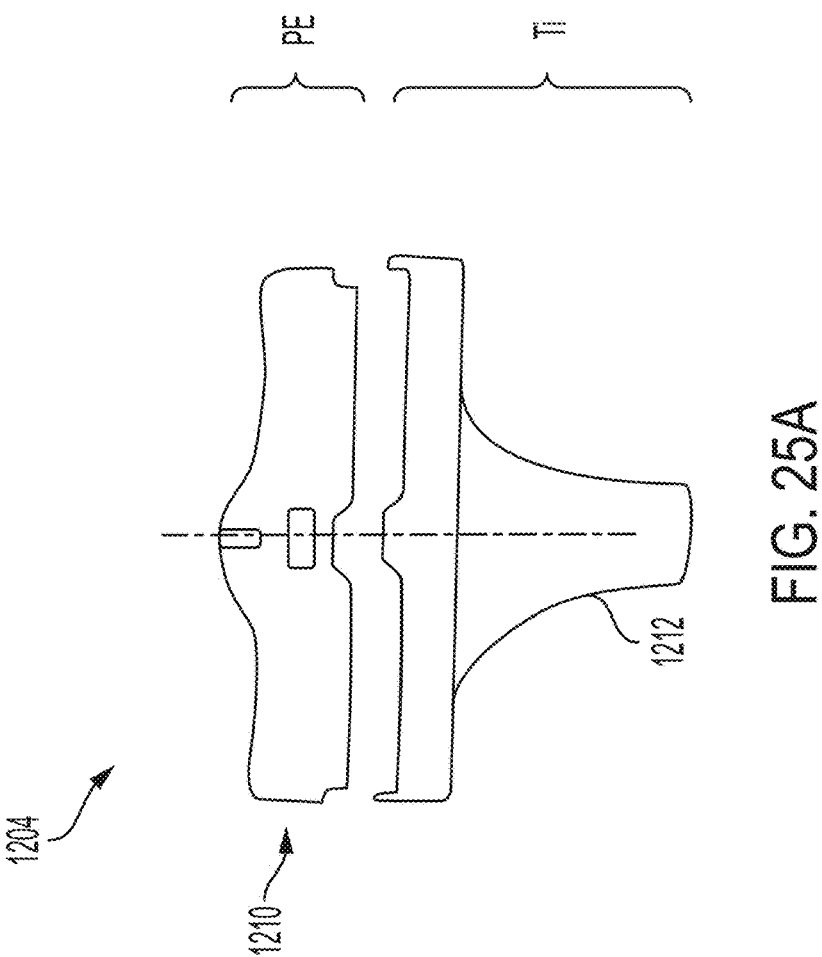
FIG. 25A is a front view of a tibial implant according to another embodiment of the present disclosure.

A tibial implant 1204 according to another embodiment of the present disclosure is shown in FIGS. 25A and 25B. Tibial implant 1204 is similar to tibial implant 204, and therefore like elements are referred to with similar numerals within the 1200-series of numbers. For example, tibial implant 1204 includes a tibial stem 1212 and a tibial insert 1210. However, tibial insert 1210 includes an IMU 1276 and a pressure sensor. Tibial insert 1210 is made of polyethylene and tibial stem 1212 is made of titanium in this embodiment.

Figure 26:
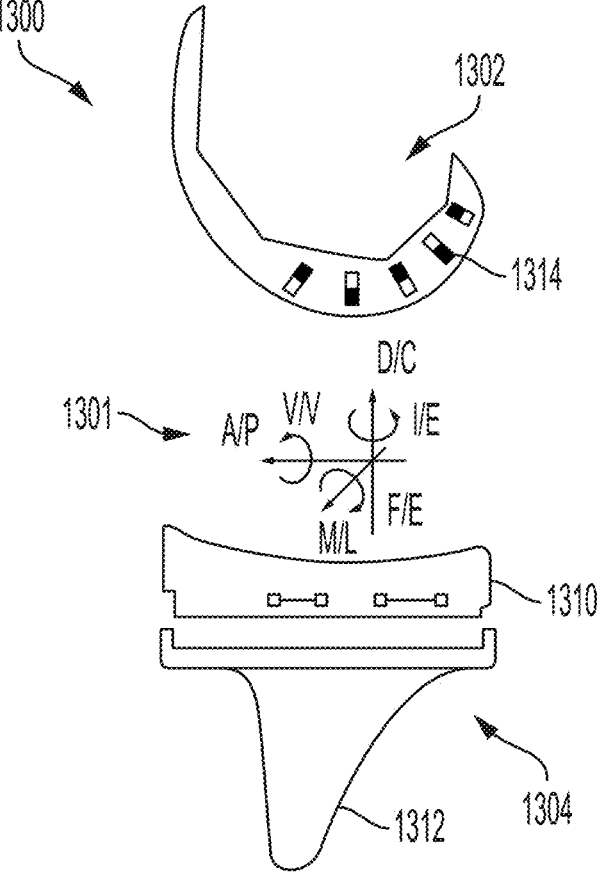
FIG. 26 is a front view of a knee joint implant according to another embodiment of the present disclosure.
Figure 27:
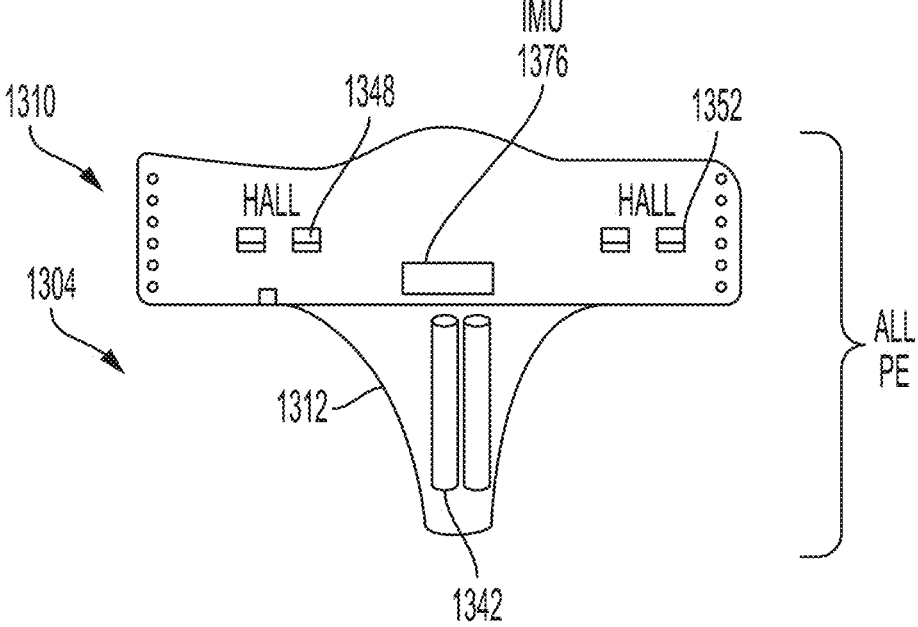
FIG. 27 is a front view of a tibial implant of the knee joint implant of FIG. 26.

FIG. 26 is a side view of a knee joint implant 1300 according to another embodiment of the present disclosure. Knee joint implant 1300 is similar to knee joint implant 200, and therefore like elements are referred to with similar numerals within the 1300-series of numbers. For example, knee joint implant 1300 includes a femoral implant 1302, a tibial implant 1304 with a tibial stem 1312 and a tibial insert 1310. However, battery 1342 of knee joint implant 1300 are located in tibial stem 1312 as best shown in FIG. 27. Locating batteries 1342 in tibial stem provides room for additional sensors in tibial insert 1310. The tibial stem and tibial insert 1310 can be made of polyethylene in this embodiment. Various knee joint implant motion data 1301 collected by magnetic markers and marker readers is shown in FIG. 26. Motion data 1301 can include internal-external rotation, medial-lateral rotation, *varus*-valgus rotation, etc.

Figure 28:
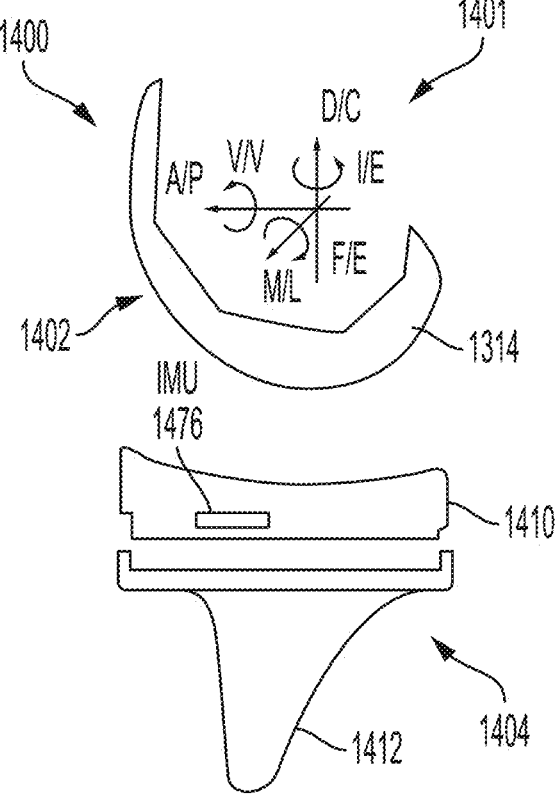
FIG. 28 is a schematic side view of a knee joint implant illustrating various measurements according to another embodiment of the present disclosure.

A knee joint implant 1400 according to another embodiment of the present disclosure is shown in FIG. 28. Knee joint implant 1400 is similar to knee joint implant 200, and therefore like elements are referred to with similar numerals within the 1400-series of numbers. For example, knee joint implant 1400 includes a femoral implant 1402, a tibial implant 1404 with a tibial stem 1412 and a tibial insert 1410. However, tibial insert 1410 includes an IMU 1476. Sensor data from IMU 1476 provides additional knee implant joint motion data 1401. Motion data 1401 can include internal-external rotation, medial-lateral rotation, *varus*-valgus rotation, etc. for reviewing knee joint implant 1400 performance. For example, internal-external rotation measurements exceeding a predetermined threshold can indicate knee joint implant lift-off (instability), medial-lateral rotation measurements exceeding predetermined thresholds can indicate knee joint implant stiffness. Combining these measurements with inputs from the various other sensors of tibial insert 1410 will provide a detailed assessment of knee joint implant 400 performance.

Figure 29:
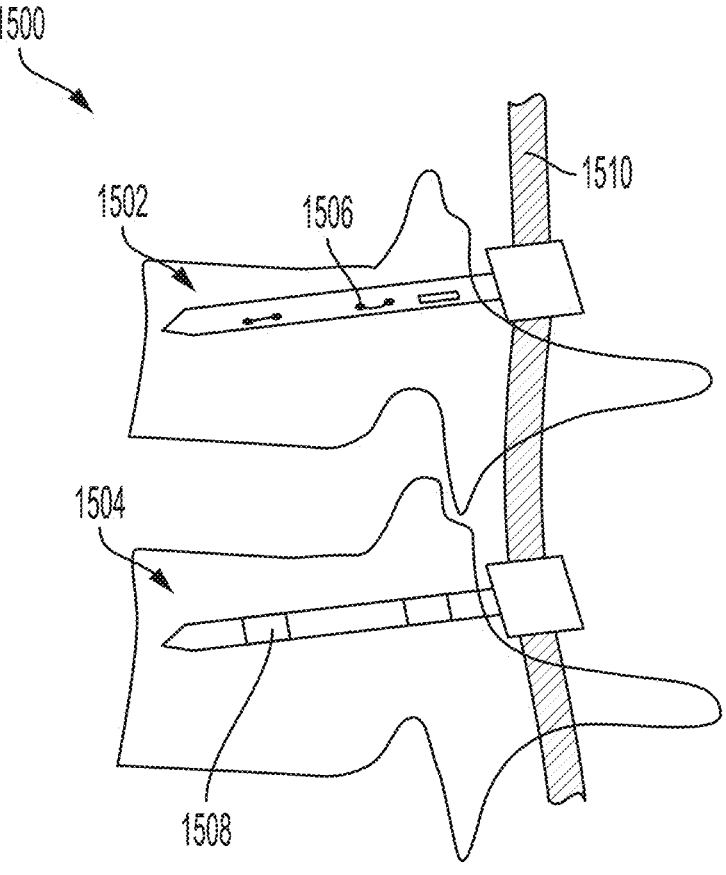
FIG. 29 is a schematic side view of a spinal implant assembly according to another embodiment of the present disclosure.

Referring now to FIG. 29, a spinal implant assembly 1500 is shown according to an embodiment of the present disclosure. Spinal implant assembly 1500 includes a spinal implant 1510 such as a plate, rod, etc., secured to first and second vertebrae by a first fastener 1502 and a second fastener 1504, respectively. The first and second fasteners can be screws as shown in FIG. 29. First fastener 1502 includes magnetic flux density detectors such as Hall sensor assemblies 1506 located along a body of the fastener 1502. Second fastener 1504 includes magnetic markers 1508 located along a body of the fastener. Any movement of second fastener 1504 with respect to the first fastener is detected and measured by Hall sensor assemblies 1506. Thus, the first and second fasteners function as an absolute or incremental encoder to detect spinal mobility of a patient during daily activity. As described with reference to the knee joint implants disclosed above, various other sensors such as temperature, pressure, pH, load, etc., can be included in fast fastener 1502 to provide additional measurements related to spinal implant assembly 1500 performance during a patient's recovery and rehabilitation. Ideally, there should be little to no movement between the first and second vertebrae for successful for spinal fusion. Therefore, any movement detected between the first and second fastener may indicate a compromised spinal implant assembly.

Figure 30:
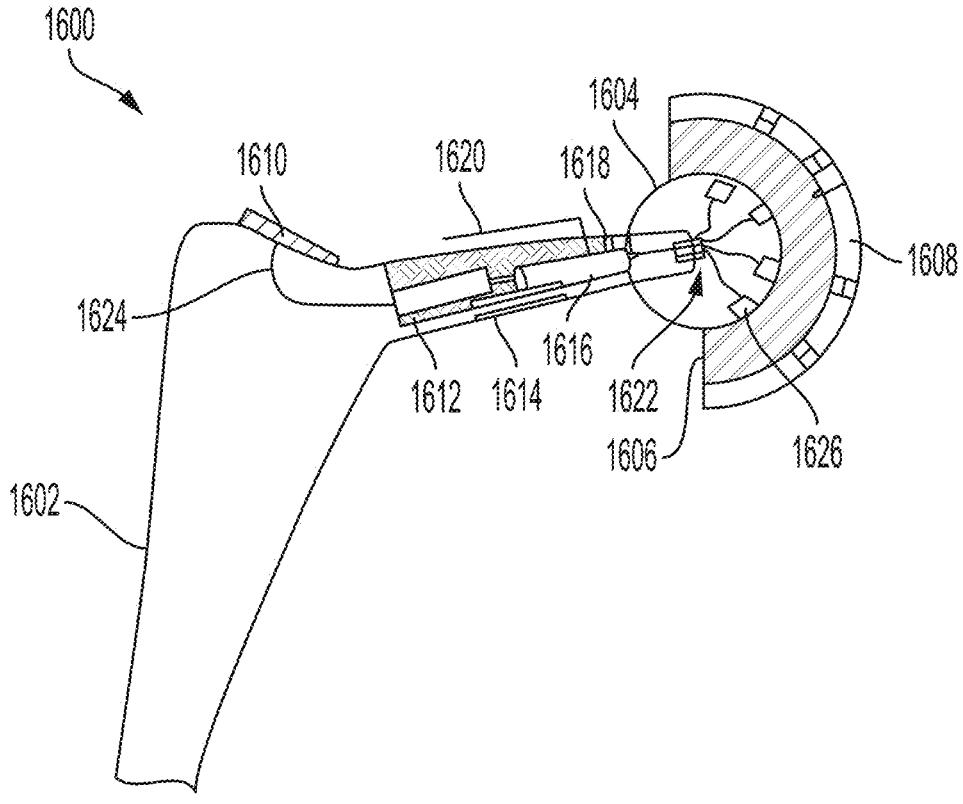
FIG. 30 is side view of a hip implant according to another embodiment of the present disclosure.
Figure 31C:
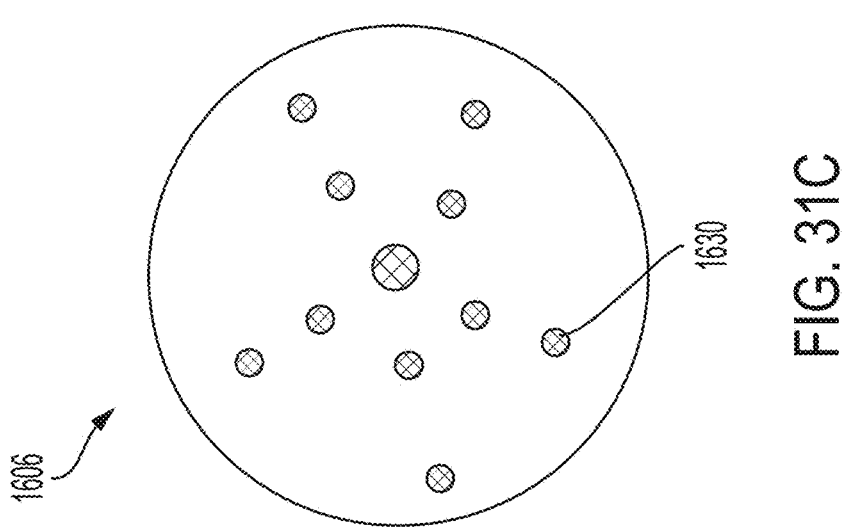
FIG. 31C is a top view of the sensor assembly and the insert of FIG. 31B.
Figure 31B:
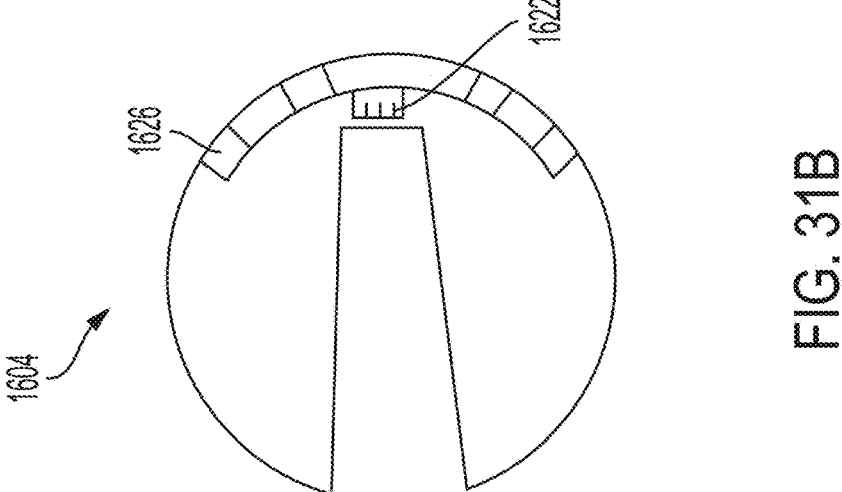
FIG. 31B is a side view of the sensor assembly and an insert of the hip implant of FIG. 31A.
Figure 31A:
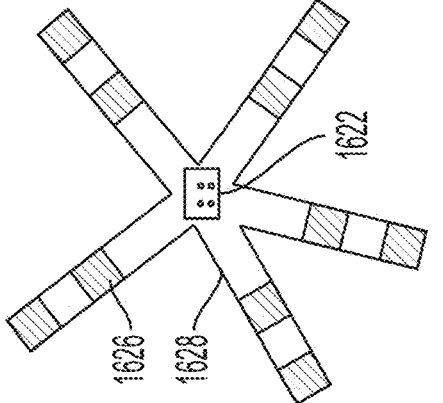
FIG. 31A is a schematic view of a sensor assembly of the hip implant of FIG. 30.

FIG. 30 is side view of a hip implant 1600 according to an embodiment of the present disclosure. Hip implant 1600 includes a stem 1602, a femoral head 1604, an insert 1606 and an acetabular component 1608. Magnetic flux density sensors such as Hall sensor assemblies 1626 are located on a flex connect 1628 and placed around femoral head 1604 as shown in FIGS. 31A and 31B. A connector 1622 on flex connect 1628 allows for convenient connection of femoral head 1604 with stem 1602. Magnetic markers 1630 are located on insert 1606 as best shown in FIG. 31C. Any motion of insert 1606 is detected by Hall sensor assemblies 1626 by measuring the change in magnetic flux density. Thus, Hall sensor assemblies 1626 and markers 1630 function as an absolute or incremental encoder to detect hip movement of a patient during daily activity.

Hip implant 1600 includes a charging coil 1610 located on stem 1602 as shown in FIG. 30. Charging coil 1610 charges a battery 1612 via a connector 1624 to power the various sensors located in hip implant 1600. A load sensor 1614 such a strain gauge detects forces between stem 1602 and acetabular component 1608 to monitor and transmit hip loads during patient rehabilitation and recovery. Various electronic components 1616, including sensors described with reference to knee joint implants, are located in stem 1602. A pH sensor 1618 located on stem can measure alkalinity and provide early detection notice of implant related infection. Data from these sensors is transmitted to an external source via an antenna 1620 as described with reference to the knee joint implants disclosed above.

Figure 32:
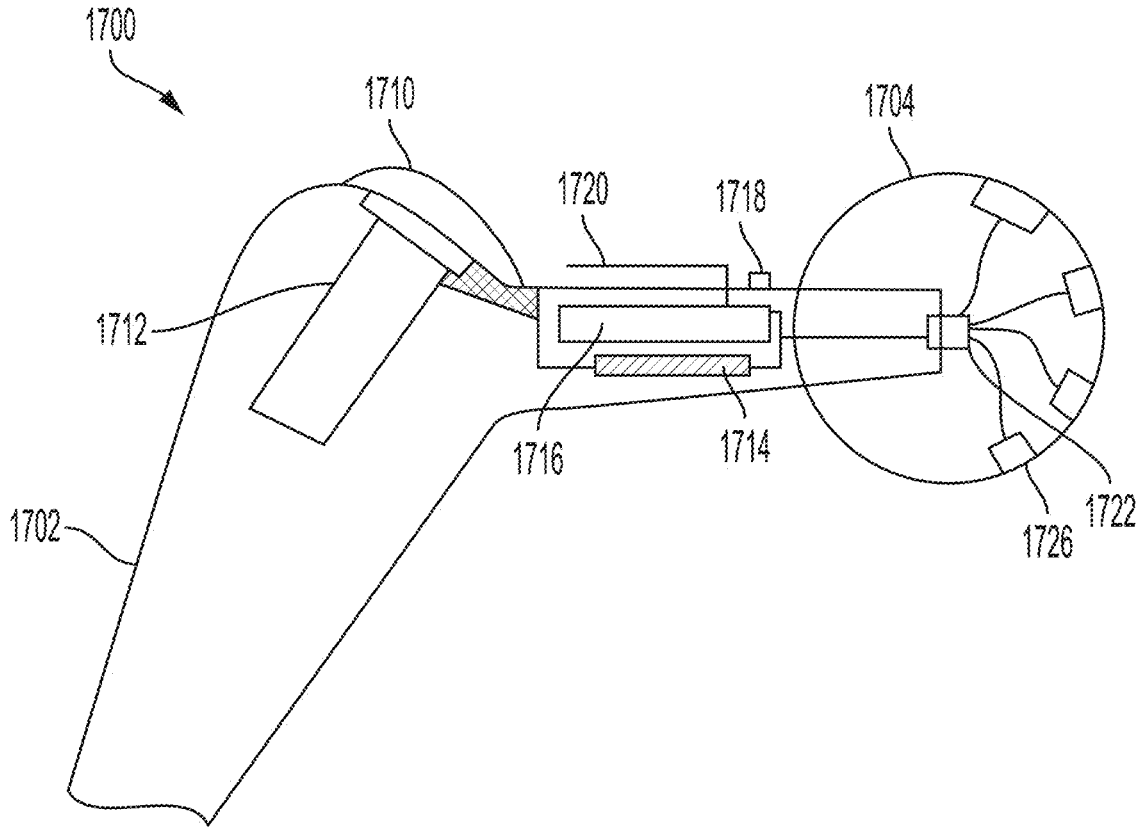
FIG. 32 is a side view of a hip implant according to another embodiment of the present disclosure.
Figure 33:
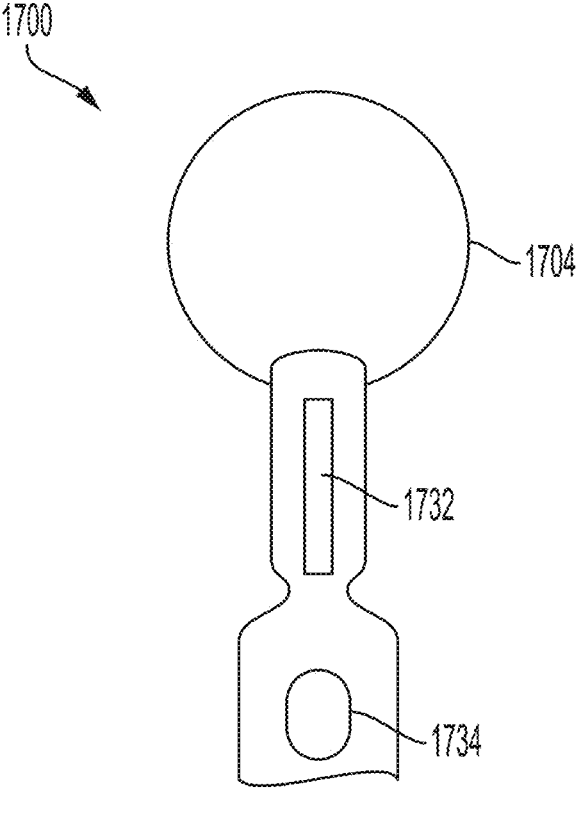
FIG. 33 is a partial top view of the hip implant of FIG. 32.

FIG. 32 is a side view of a hip implant 1700 according to another embodiment of the present disclosure. Hip implant 1700 is similar to hip implant 1600, and therefore like elements are referred to with similar numerals within the 1700-series of numbers. For example, hip implant 1700 includes a stem 1702, a femoral head 1704 and an acetabular component (not shown). However, battery 1712 of hip implant 1700 is located away from electric components 1716 as best shown in FIG. 32. Battery 1712 can be conveniently inserted into hip implant 1700 via a slot 1734 as shown in FIG. 33. Similarly, electric components 1716 can be inserted into hip implant 1700 via a slot 1732. This allows for convenient replacements and upgrades to the battery and electric components without disturbing hip implant 1700.

Figure 34:
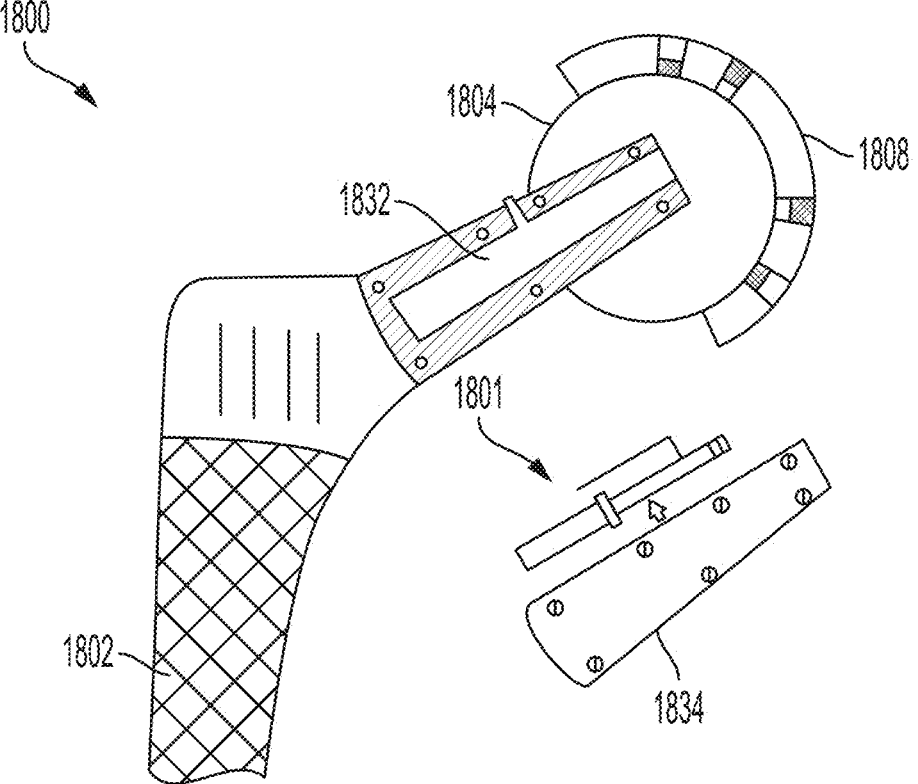
FIG. 34 is a side view of a hip implant according to another embodiment of the present disclosure.

FIG. 34 is a side view of a hip implant 1800 according to another embodiment of the present disclosure. Hip implant 1800 is similar to hip implant 1600, and therefore like elements are referred to with similar numerals within the 1800-series of numbers. For example, hip implant 1800 includes a stem 1802, a femoral head 1804 and an acetabular component (not shown). However, slot 1832 of hip implant 1800 is configured to receive all electronic components structured as a modular electronic assembly 1801 or a sensor assembly. A slot cover 1834 ensures that electronic assembly 1801 is secured and sealed in slot 1832. Thus, hip implant 1800 can be easily provided with replacement or upgrades to the electric components without disturbing hip implant 1800.

Figure 35:
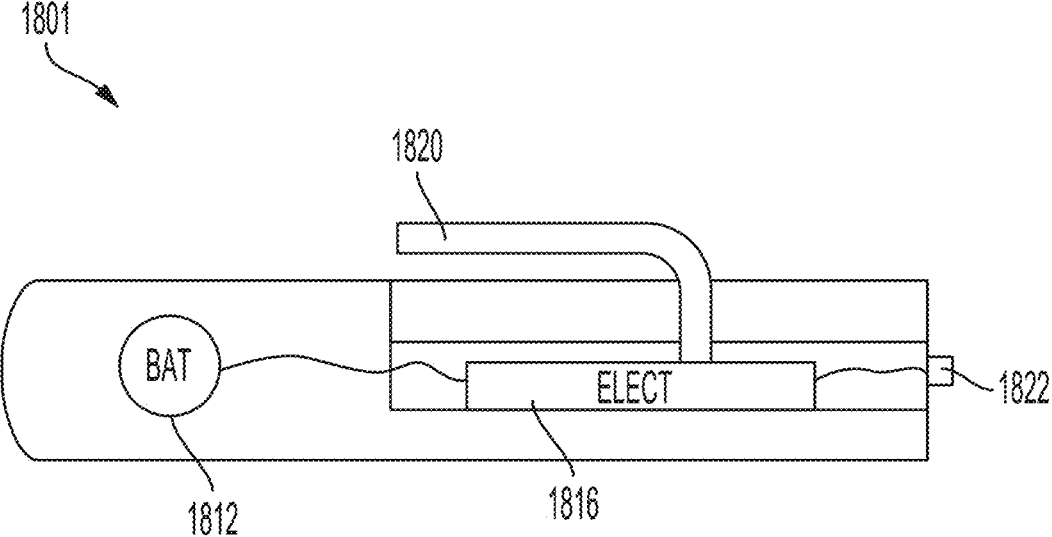
FIG. 35 is a side view of an electronic assembly of the hip implant of FIG. 34 according to another embodiment of the present disclosure.
Figure 36:
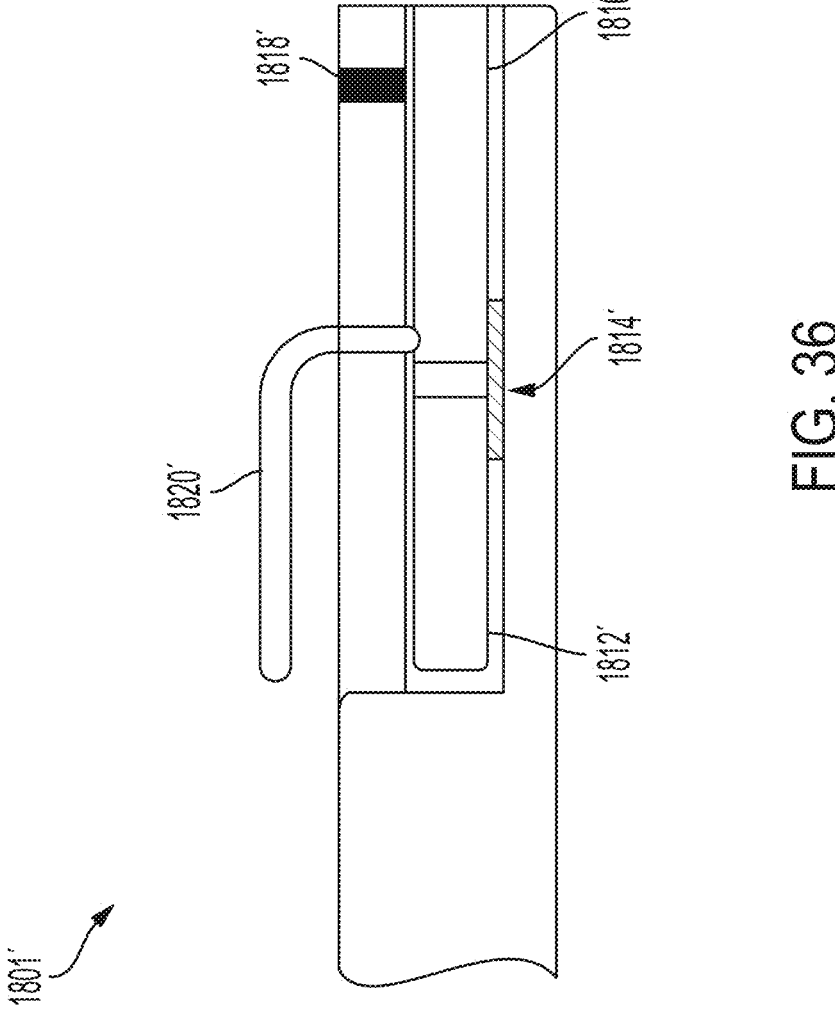
FIG. 36 is a side view of an electronic assembly of the hip implant of FIG. 34 according to another embodiment of the present disclosure.

A first embodiment of a modular electronic assembly 1801 is shown in FIG. 35. Electronic assembly includes a connector 1822 to connect to femoral head 1804, various electronic components 1816, a battery 1812 and an antenna 1820. Another embodiment of a modular electronic assembly 1801' is shown in FIG. 36. Electronic assembly 1801' includes various electronic components 1816', a battery 1812', a load sensor such as a strain gauge 1814' and an antenna 1820'. Electronic assembly 1801' includes a pH sensor 1818' to provide early detection of implant related infection.

Figure 37:
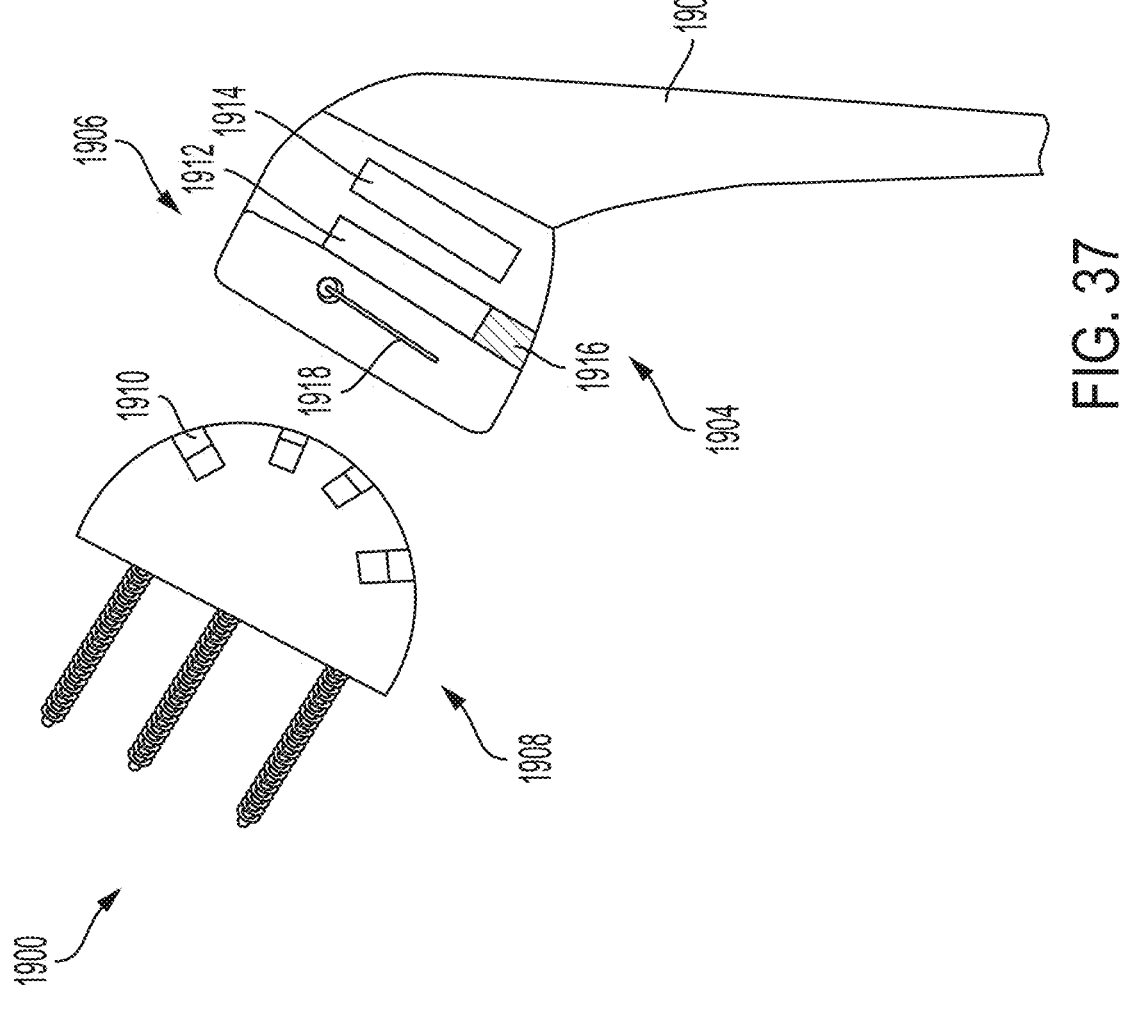
FIG. 37 is a side view of a shoulder implant according to another embodiment of the present disclosure.
Figure 39:
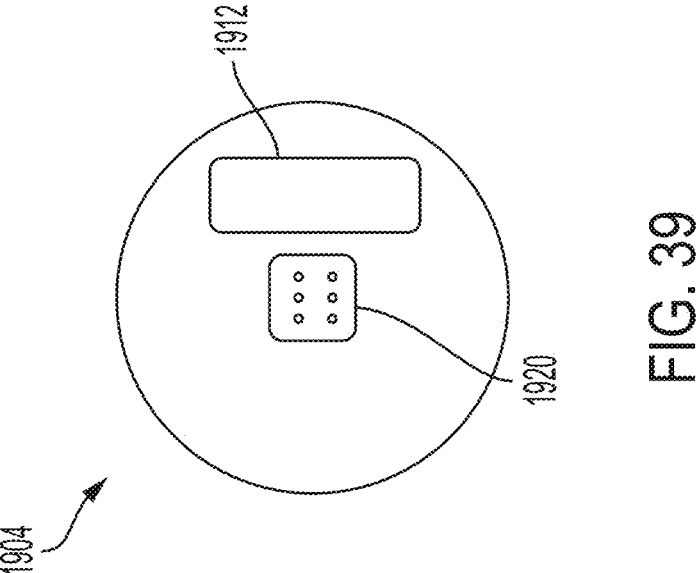
FIG. 39 is a top view of a cup of the shoulder implant of FIG. 37.
Figure 38:
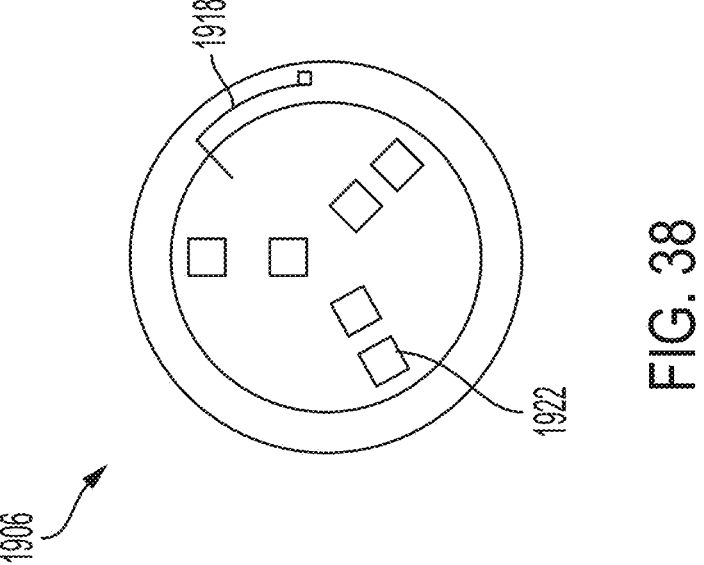
FIG. 38 is top view of an insert of the shoulder implant of FIG. 37.

FIG. 37 is a side view of a reverse shoulder implant 1900 according to an embodiment of the present disclosure. Shoulder implant 1900 includes a stem 1902, a cup 1904, an insert 1906 and a glenoid sphere 1908. Magnetic flux density sensors such as Hall sensor assemblies 1922 are located on insert 1906 as shown in FIG. 38. A connector 1920 on cup 1904 as shown in FIG. 39 allows for attachment of the cup to insert 1906. Magnetic markers 1910 are located on glenoid sphere 1908 as best shown in FIG. 37. Any motion of glenoid sphere 1908 is detected by Hall sensor assemblies 1922 by measuring the change in magnetic flux density. Thus, Hall sensor assemblies 1922 and markers 1910 function as an absolute or incremental encoder to detect shoulder movement of a patient during daily activity.

Shoulder implant 1900 includes a battery 1914 and an electronic assembly 1912 located within cup 1904. A pH sensor 1916 is located on cup 1904 to measure alkalinity and provide early detection notice of implant related infection. An antenna 1918 located on insert 1906 is provided to transmit sensor data to an external source to monitor and transmit shoulder implant 1900 performance during patient rehabilitation and recovery. Various electronic components of electronic assembly 1912, including sensors described with reference to knee joint implants, are located in cup 1904.

Figure 41:
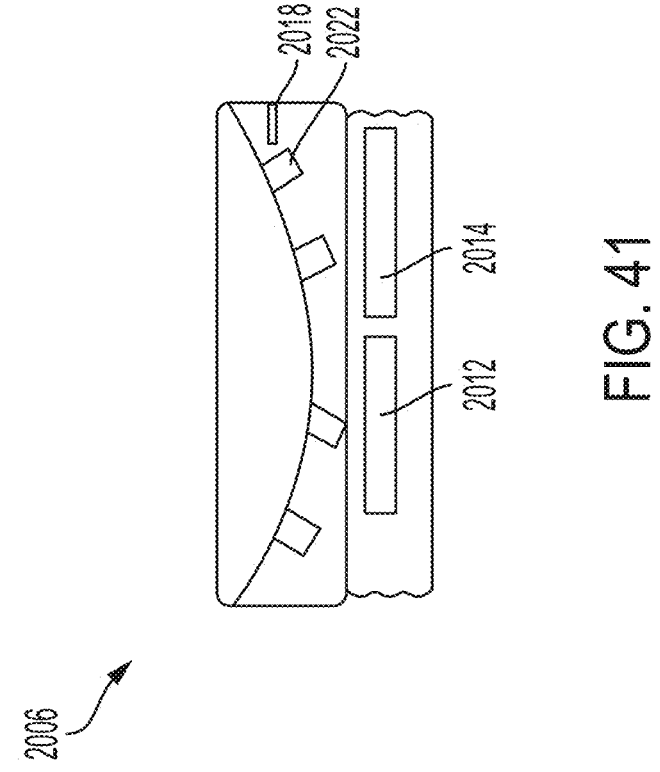
FIG. 41 is a side view of an insert of the shoulder implant of FIG. 40.
Figure 40:
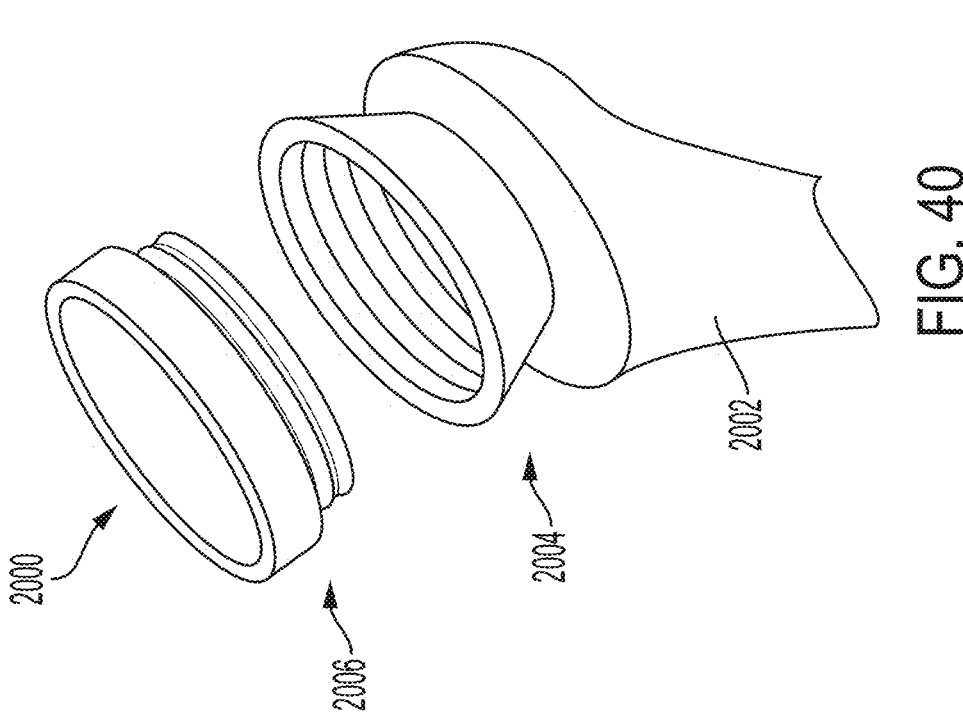
FIG. 40 is side view of a shoulder implant according to another embodiment of the present disclosure.

FIG. 40 is a side view of a reverse shoulder implant 2000 according to another embodiment of the present disclosure. Shoulder implant 2000 is similar to shoulder implant 1900, and therefore like elements are referred to with similar numerals within the 2000-series of numbers. For example, shoulder implant 2000 includes a stem 2002, a cup 2004 and an insert 2006. However, electronic assembly 2012, battery 2014 and pH sensor 2018 are located in insert 2006 as shown in FIG. 41. Thus, only a single component—i.e., the cup, of shoulder implant 2000 can be replaced or upgraded to make changes to sensor collection and transmission of the shoulder implant performance data.

Figure 42:
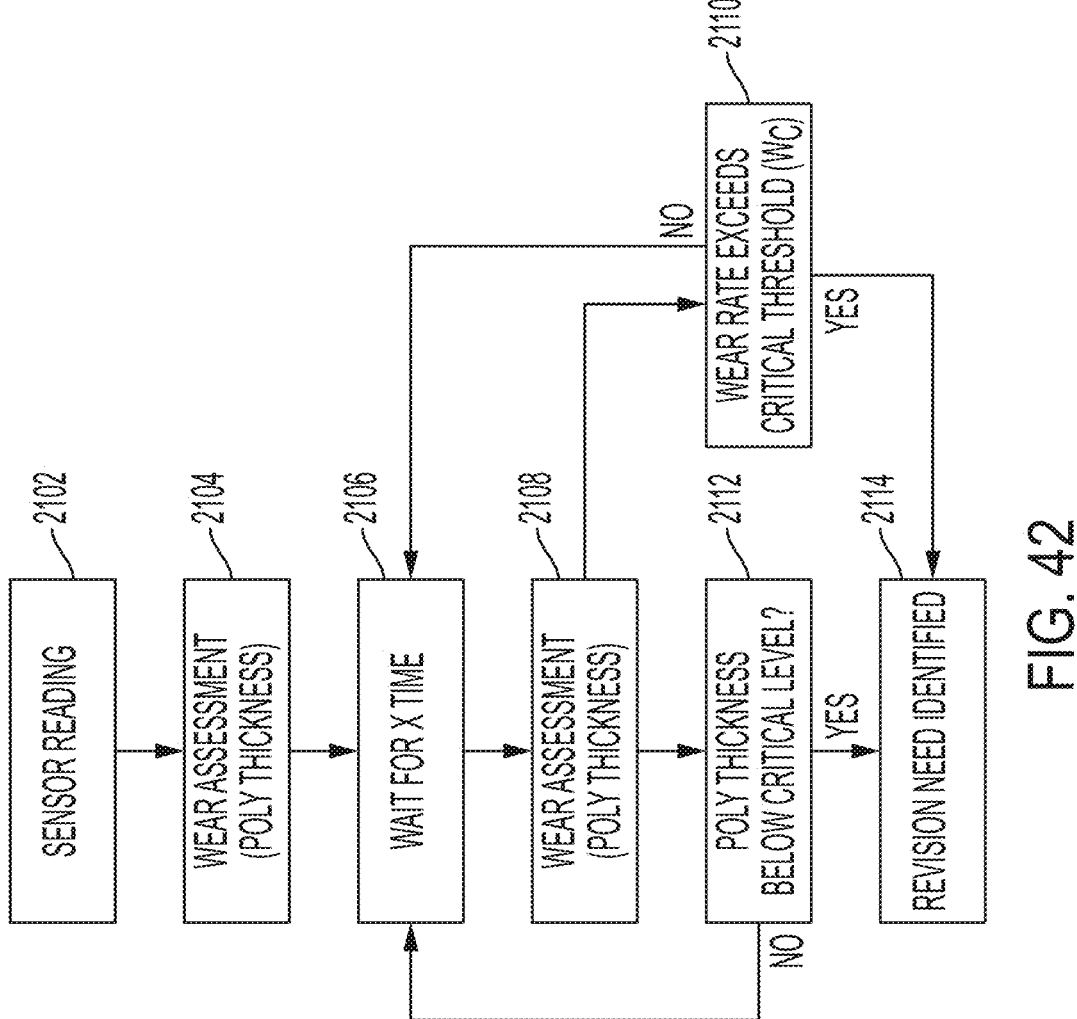
FIG. 42 is a flowchart showing steps to determine implant wear according to another embodiment of the present disclosure.
Figure 42:

FIG. 42 is a flowchart showing steps of a method 2100 to determine implant wear according to an embodiment of the present disclosure. While method 2100 is described with reference to a knee joint implant below, method 2100 can be applied to any implant with sensors described in the present disclosure, including all of the implants disclosed above. In a first step 2102, the initial thickness of the knee joint implant (such as thickness of the tibial insert) is recorded. This can be obtained by measuring the tibial insert prior to implantation, or measured based on the magnetic flux density generated by the magnetic markers as measured by the Hall sensor assemblies. Once the knee joint implant is implanted, periodic measurements of tibial insert thickness are determined in a step 2104 by evaluating the magnetic flux density. As the polyethylene housing of tibial insert degrades over time, the distance between the markers and Hall sensor assemblies are reduced as measured in a step 2106. This results in increased magnetic flux density values, which are used to estimate tibial insert wear in a step 2108.

Figures 43, 44:
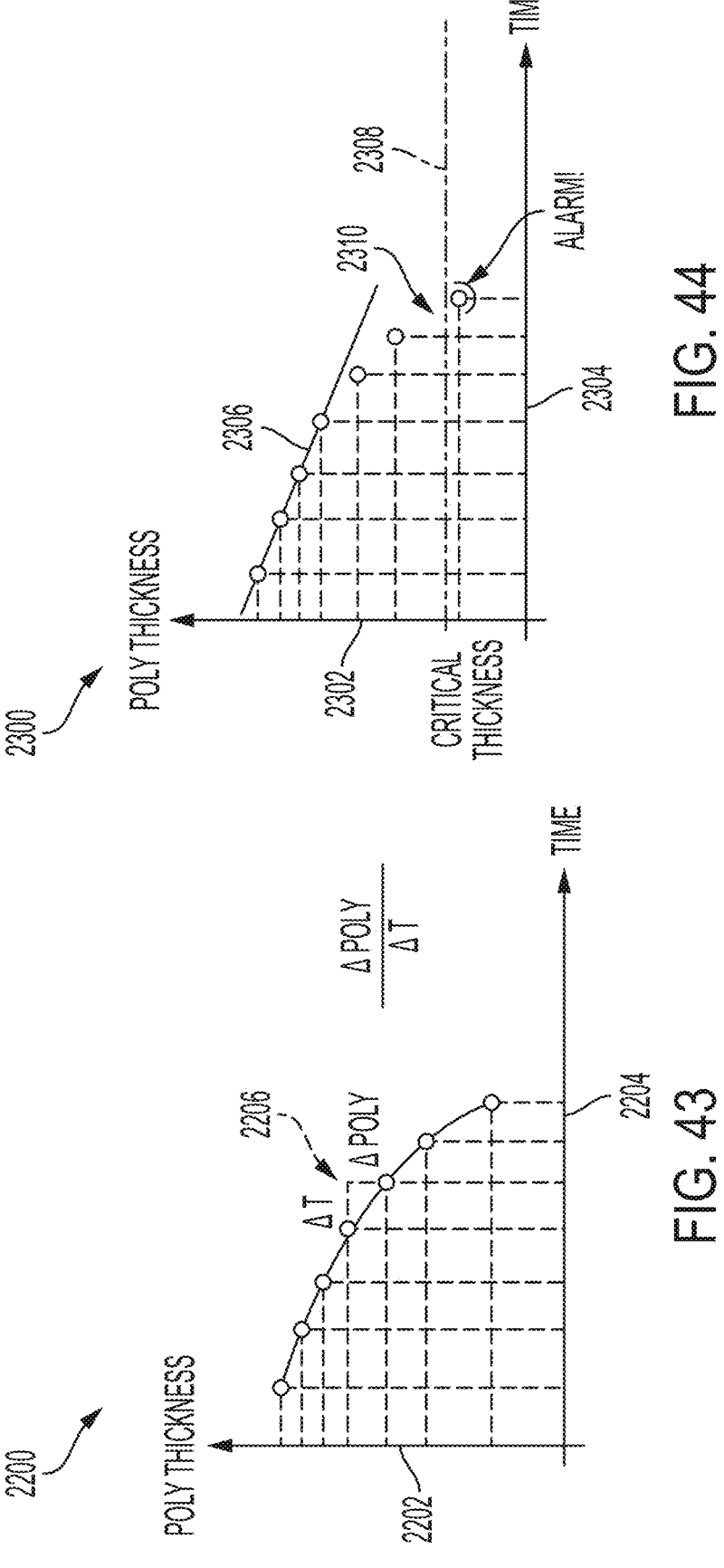
FIG. 43 is a first graph showing implant thickness over time.
FIG. 44 is a second graph showing implant thickness over time.

The decision to replace the tibial insert can be based on a rate of wear threshold 2206 as shown in graph 2200 of FIG. 43 in a step 2110, or a critical thickness value 2308 as shown in graph 2300 of FIG. 44 in a step 2112. Graph 2200 plots tibial insert thickness 2202 over time 2204. A change in slope 2206 denotes the rate of wear of tibial insert. When slope 2206 exceeds the predetermined rate of wear threshold, notification to replace the tibial insert is triggered in a step 2114. Graph 2300 plots tibial insert thickness 2302 over time 2304. When the tibial insert thickness is less than a predetermined critical thickness value 2308, a notification 2310 is triggered to replace the tibial insert in step 2114.

Figure 45:
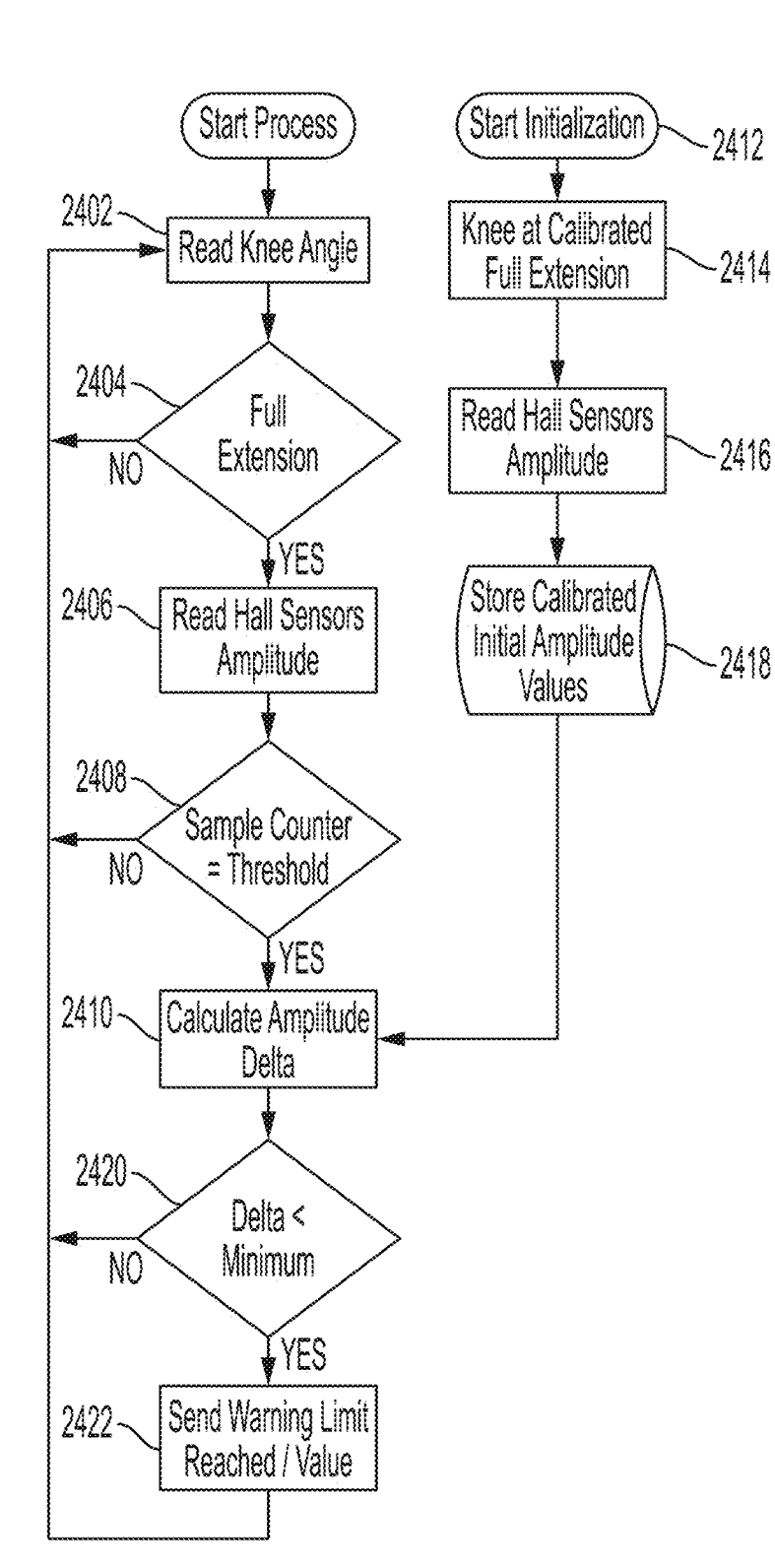
FIG. 45 is a flowchart showing steps to determine implant wear according to another embodiment of the present disclosure.

FIG. 45 is a flowchart showing steps of a method 2400 to determine implant wear according to another embodiment of the present disclosure. While method 2400 is described with reference to a knee joint implant below, method 2400 can be applied to any implant with sensors described in the present disclosure, including all of the implants disclosed above. In a first step 2402, a knee angle of a patient with the knee joint implant is measured. The knee is then placed in full extension in a step 2404. Hall sensor amplitudes are measured in a step 2408. This process is repeated over time to track the Hall sensor amplitude. These values are then compared with initial Hall sensor amplitude values obtained when the knee implant joint template was implanted (obtained by performing steps 2412 to 2418). As the Hall sensor amplitudes are directly related to a distance between the markers and the marker readers—i.e., a tibial insert thickness, a difference between the initial Hall sensor amplitudes and current Hall sensor amplitudes from step 2408 represent wear of the tibial insert in a step 2420. When a predetermined minimum implant thickness is reached in a step 2420, a notification to replace the tibial insert is triggered in a step 2422.

Figure 46:
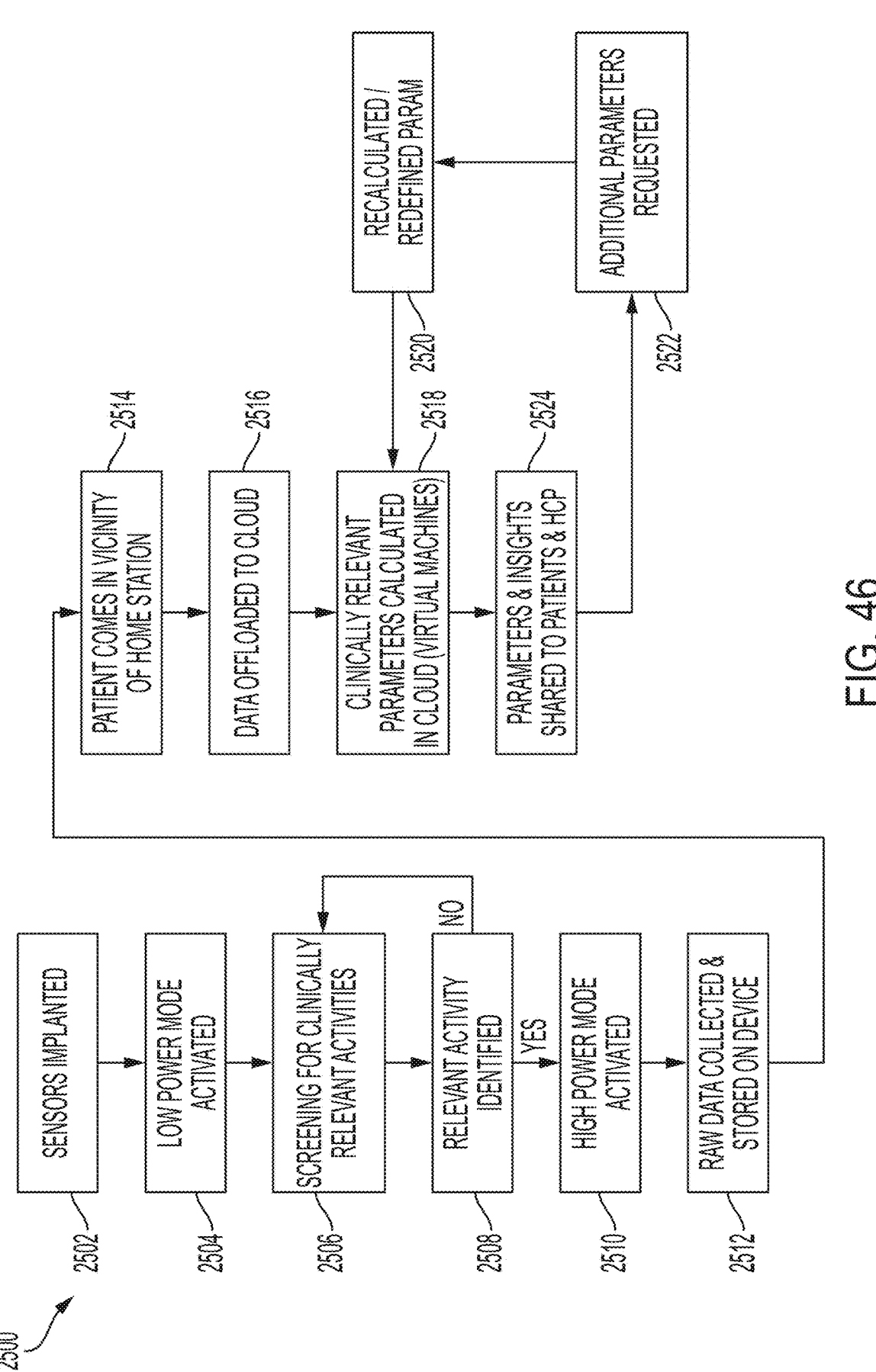
FIG. 46 is a flowchart showing for implant data collection according to another embodiment of the present disclosure.

FIG. 46 is a flowchart showing steps of a method 2500 for implant data collection according to an embodiment of the present disclosure. While method 2500 is described with reference to a knee joint implant below, method 2500 can be applied to any implant with sensors described in the present disclosure, including all of the implants disclosed above. In a first step 2502, a patient is implanted with a knee joint implant. The knee joint implant is in a low-power mode (to conserve battery power) until relevant activity is detected (steps 2504 and 2506). Once the relevant activity is identified by the sensor(s) of the knee joint implant (step 2508), the implant shifts to a high-power mode. Relevant activity to trigger the high-power mode can be patient-specific, and may include knee flexion speed, gait, exposure to sudden impact loads, temperature thresholds, alkalinity levels, etc. Upon identifying the relevant activity and switching over to the high-power mode, various sensors in the knee joint implant record and store sensor measurements on the device (step 2512). This data can be transferred from the patient to a home station when the patient is in the vicinity of the home station or a smart device (step 2514). The data is then transferred from the home station or the smart device to the cloud 5850 to be reviewed and analyzed by the software 5860 or virtual machines and/or by experts (steps 2518, 2520). Relevant information for patient rehabilitation and recovery uncovered from the sensor data is sent back to the patient (steps 2523, 2522) via the client portal 5856. Thus, method 2500 preserves and extends battery life of the knee joint implant by shifting the implant from low-power to high-power mode when required, and shifting the implant back to the low-power mode to conserve energy during other periods.

In some examples, the relevant patient information may be that the knee joint and knee joint implant are in a healthy state, or alternatively that the knee joint is in an infected state. If the knee joint is determined to not be in a healthy state, the clinician can then take steps to review the condition more closely and prepare a plan for treatment if necessary. After review, the clinician can input the state of the joint as determined by the clinician so that the confirmed diagnosis is then associated with the data provided by the joint implant. The diagnosis data combined with corresponding sensor data is then stored in the cloud 5850 and henceforth considered in the software's future determinations of the state of a joint and joint implant. In some examples, the software is adapted to adjust and further refine its parameters and/or thresholds used in determining the state of an implant upon receipt of the diagnosis data.

Figure 47A:
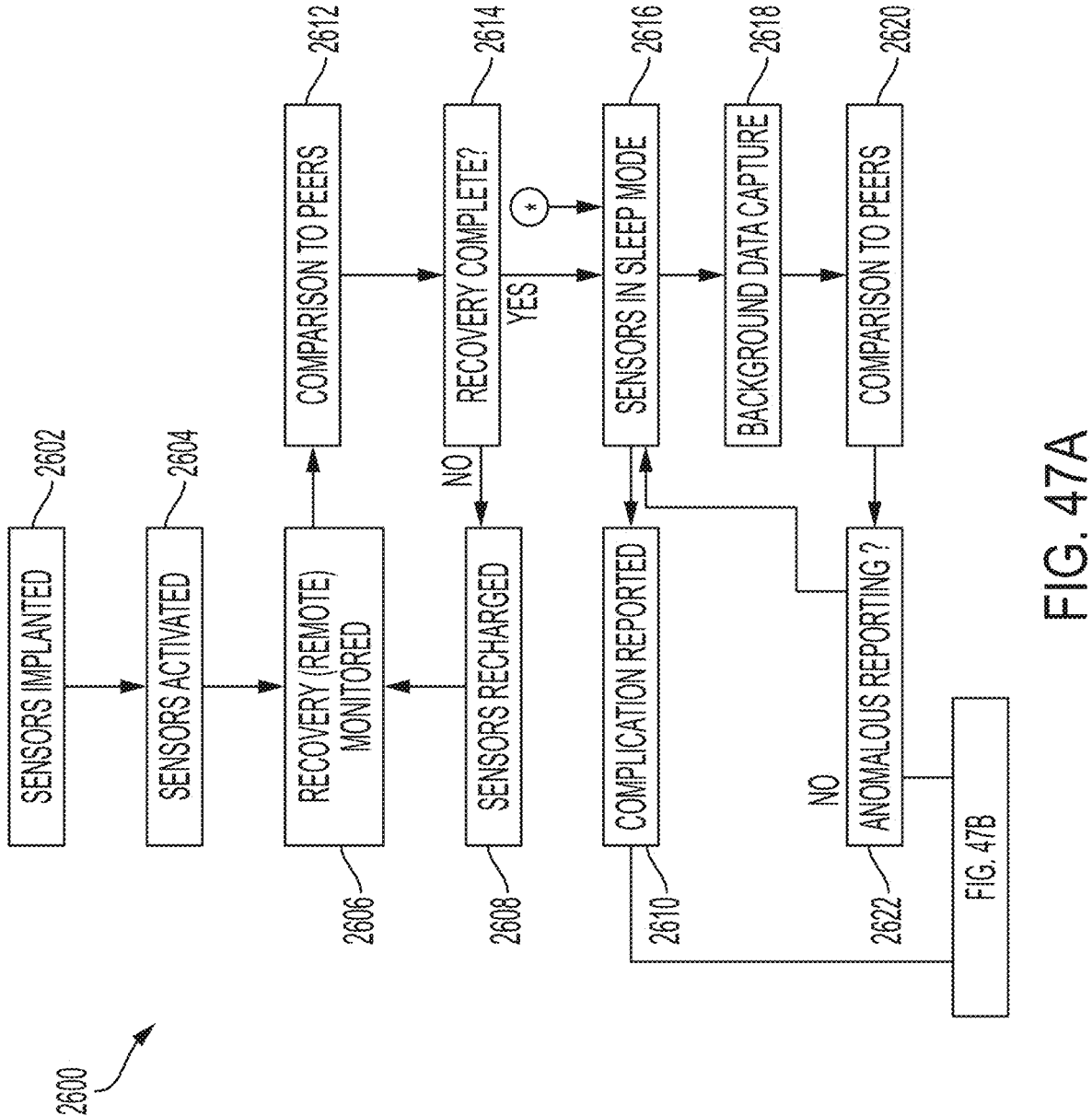
FIGS. 47A and 47B is a flowchart showing steps for patient monitoring according to another embodiment of the present disclosure.
Figure 47B:
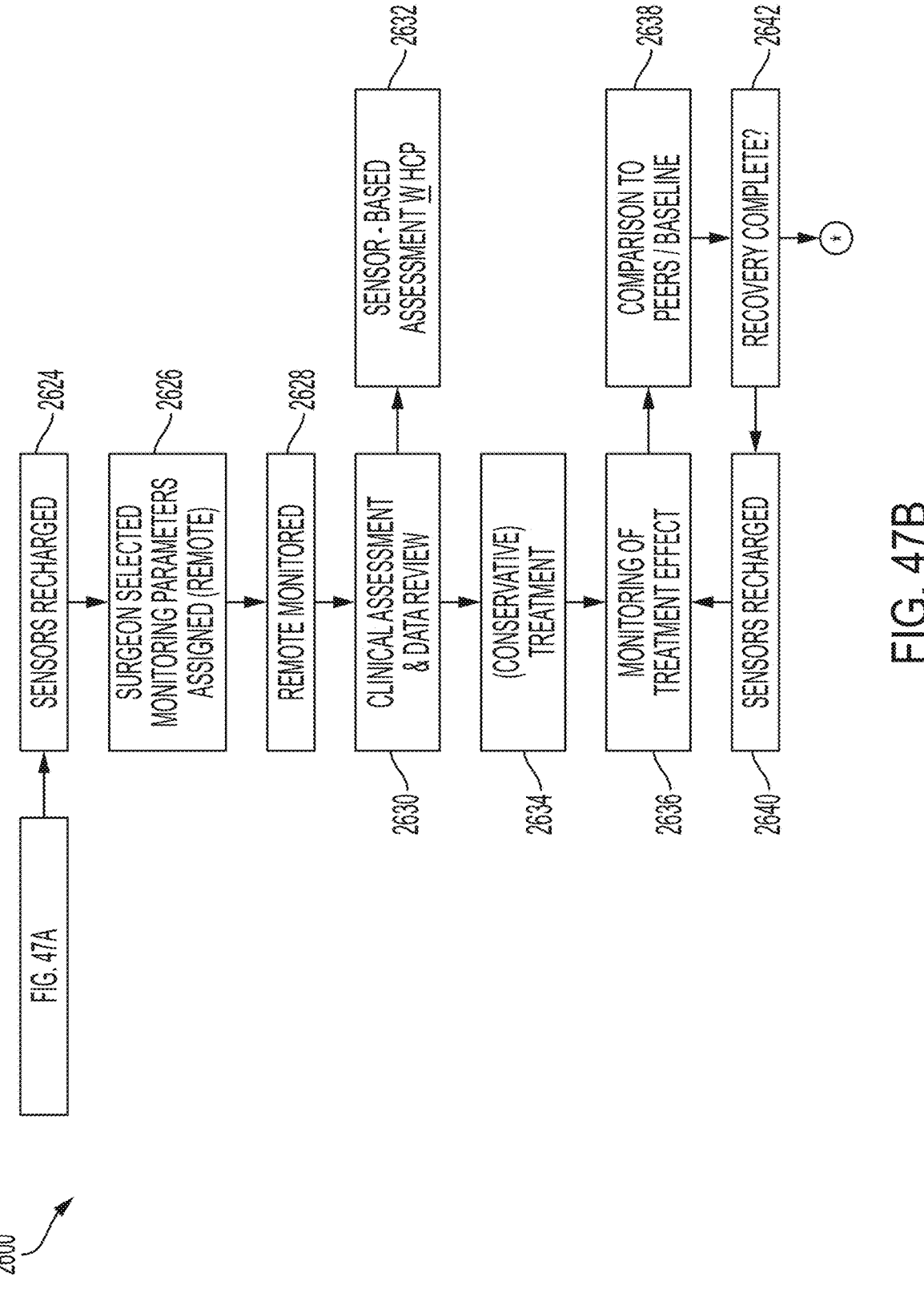

FIGS. 47A and 47B shows steps of a method 2600 for patient monitoring according to an embodiment of the present disclosure. While method 2600 is described with reference to a knee joint implant below, method 2600 can be applied to any implant with sensors described in the present disclosure, including all of the implants disclosed above. After installing the knee joint implant, various sensors within the sensor are activated (steps 2624, 2626) to track and monitor patient rehabilitation and recovery (step 2628). When the tracked data indicates that the desired recovery parameters are achieved, some of the sensors in the knee joint implant are deactivated or turned to a "sleep mode" (step 2616). For example, the recovery target can be a desired range of motion of the knee joint. Once a patient exhibits the desired knee flexion-extension range, some of the sensors on the knee joint implant can be turned off. Alternatively, peer data can be used to identify recovery thresholds (step 2612). If the recovery threshold or milestones are not achieved, the knee joint implant continues to charge and use all sensors (step 2608). Some sensors in the knee joint implant will be periodically used even after achieving the recovery milestones to monitor for early identification of improper implant performance (step 2610, 2618, 2620). For example, after turning off the magnetic readers upon achieving the desired flexion-extension range of motion, the pH or temperature sensors can be used to periodically measure alkalinity and temperature to identify infection or implant failure. Upon identification of an anomalous condition, the knee joint implant can be configured to fully recharge and turn on the previously turned off sensors to provide additional implant performance measurements (step 2624). A surgeon can customize the sensor readings and frequency based on the observed condition (steps 2626 and 2628). Additional rehabilitation steps for patient recovery can be provided to the patient at this point. The impact of the new rehabilitation steps can be monitored and compared with peers to observe patient recovery (steps 2636-2642).

Figure 48:
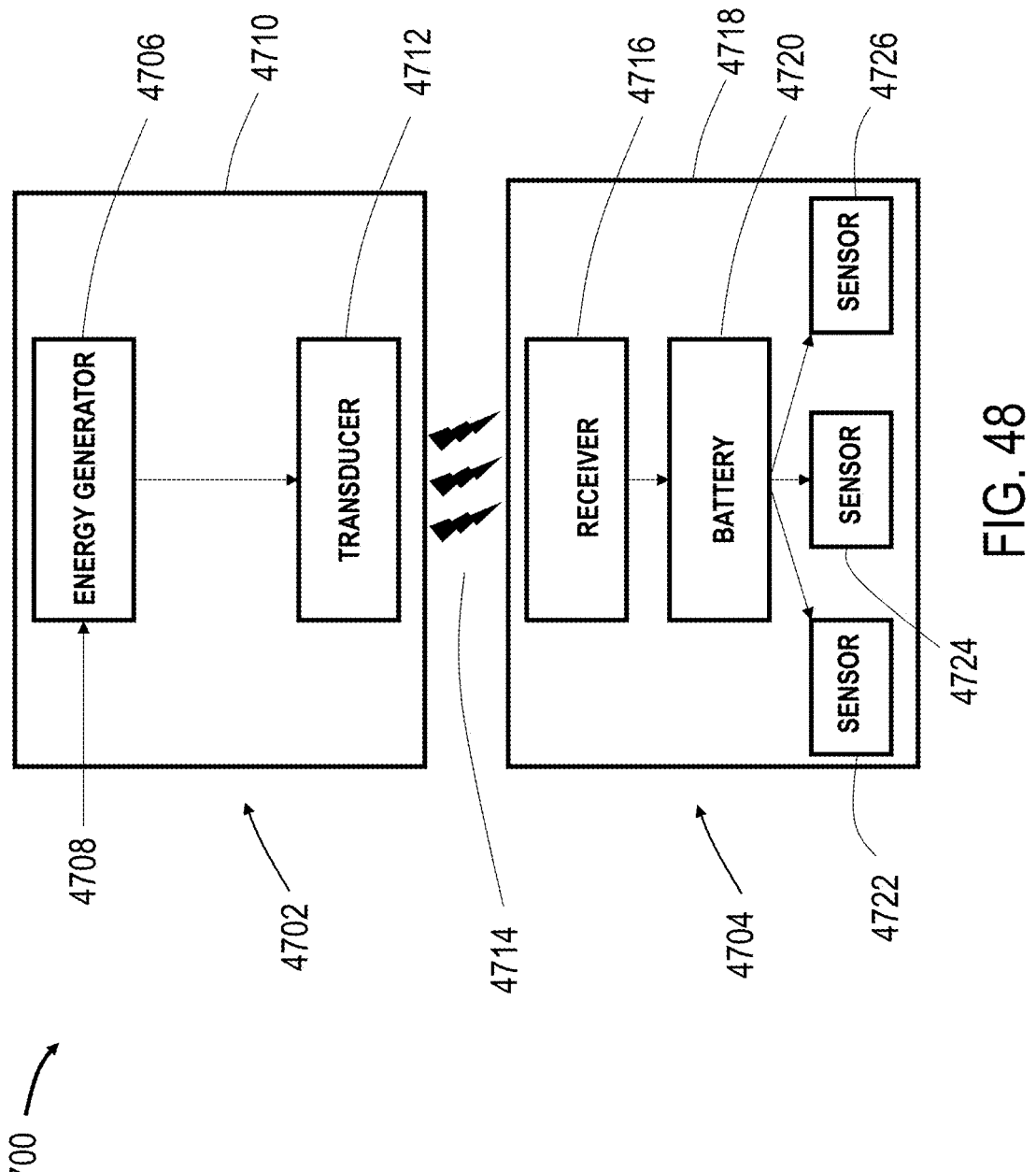
FIG. 48 is a schematic drawing of an implant with an energy generator according to an embodiment of the present disclosure.

FIG. 48 is a schematic drawing of an implant 4700 according to an embodiment of the present disclosure. Implant 4700 can be a joint implant such as a knee implant, shoulder implant, hip implant, etc. While the disclosure herein generally discusses embodiments directed to joint implants, the components and features disclosed herein are not limited to joint implants but can be used in any other implant or trial. Implant 4700 can include a first implant 4702 and a second implant 4704. First implant 4702 can include an energy generator 4706 electrically connected to a transducer 4712 within a body 4710 of the first implant as shown in FIG. 48. Energy generator 4706 can be any type of energy generating device capable of converting mechanical, chemical, heat or other forms of energy 4708 available in a human body to electrical energy. For example, energy generator 4706 can be an electromagnetic energy generator with a plurality of magnets configured to generate electricity via the relative motion of the magnets. The relative motion of the magnets can be caused by various activities of the patient including walking, standing, etc. Energy generator 4706 can be a triboelectric energy generator producing energy by motion/translation of triboelectric material. In other embodiments energy generator can include a Piezoelectric energy generator, thermocouple energy generator, etc.

Electric energy generated by energy generator 4706 is transmitted to transducer 4712. Transducer 4712 can be an electroacoustic transducer configured to convert the electrical energy received from energy generator to acoustic energy and then acoustically transfer 4714 to a receiver 4716 of second implant 4704 as shown in FIG. 48. In one embodiment, implant 4700 can include an ultrasonic transducer 4712 and an ultrasonic receiver 4716 to transfer energy from the first implant to the second implant via ultrasound. Ultrasonic receiver 4716 is configured to receive acoustic energy (ultrasound) from ultrasonic transducer 4712 and convert the acoustic energy to electrical energy. Various other types of electroacoustic transducers such as tactile transducers, Piezoelectric crystals etc., can be used in other embodiments to transfer acoustic energy between first implant 4702 and second implant 4704. The electroacoustic transducers can be selected based on the distance between the first and second implants or contact area between the first and second implants, implant thickness, implant material, etc. Other embodiments can use inductive coupling or other means to transfer electric energy from first implant 4702 to second implant 4704.

Second implant 4704 includes a battery 4720 electrically connected to receiver 4716 and one or more sensors 4722, 4724, 4726 with an implant body 4718 of the second implant. Battery 4720 is a rechargeable battery configured to be charged by the electrical energy transmitted from the receiver 4716. Battery 4720 can be any suitable biocompatible battery such as a solid state battery, lithium ion battery, lithium carbon monofluoride battery, lithium thionyl chloride battery, lithium ion polymer battery, etc. Because battery 4720 can be frequently charged during patient activity, the size and capacity of battery 4720 can be substantially minimized Thus, a smaller battery provides additional space for various sensors and associated electronics located within second implant 4704. Sensors 4722, 4724, 4725 can include a temperature sensor, pressure sensor, pH sensor, etc., depending on the type of implant and the desired measurements.

Acoustic energy transfer between first implant 4702 and second implant 4704 can be utilized with implants made of varied and/or dissimilar materials such as cobalt-chromium (CoCr), Titanium (Ti), cross-linked polyethylene (XLPE), etc., with varying implant thicknesses and separation between the implants or implants that contact each other. In contrast to RF or inductive power transfer mechanisms, acoustic energy transfer can be achieved even when one of the materials is conductive i.e., acts as a Faraday shield. Thus, conductive materials can be used in the implants disclosed herein. Acoustic energy transfer allows the various electronic components of the implants to be safely sealed within each implant while enabling highly efficient power transfer between first implant 4702 and second implant 4704. Wires or other components extending outside the implants necessary for direct coupling of the implants are not required for acoustic energy transfer thereby eliminating potential structural weakness in the implant bodies which may be susceptible to failure. The implants can be hermetically sealed to improve implant biocompatibility and patient safety. Thus, the electroacoustic transducer and receiver allow for wireless coupling and energy transfer. The size and type of electroacoustic transducer and receiver can be selected based on first and second implant material, thickness, separation, etc.

Various implant power management operations can be included in implant 4700 to extend battery life. Implant 4700 can operate in a low-power mode to conserve battery power until relevant activity is detected. Once the relevant activity is identified by one of the sensors 4722, 4724, 4726 of second implant 4704, the implant shifts to a high-power mode. Relevant activity to trigger the high-power mode can be patient and/or implant specific. For example, relevant activity for a knee implant may include knee flexion speed, gait, exposure to sudden impact loads, temperature thresholds, alkalinity levels, etc. Upon identifying the relevant activity and switching over to the high-power mode, various sensors in the knee joint implant record, store and transmit sensor measurements.

Figure 49:
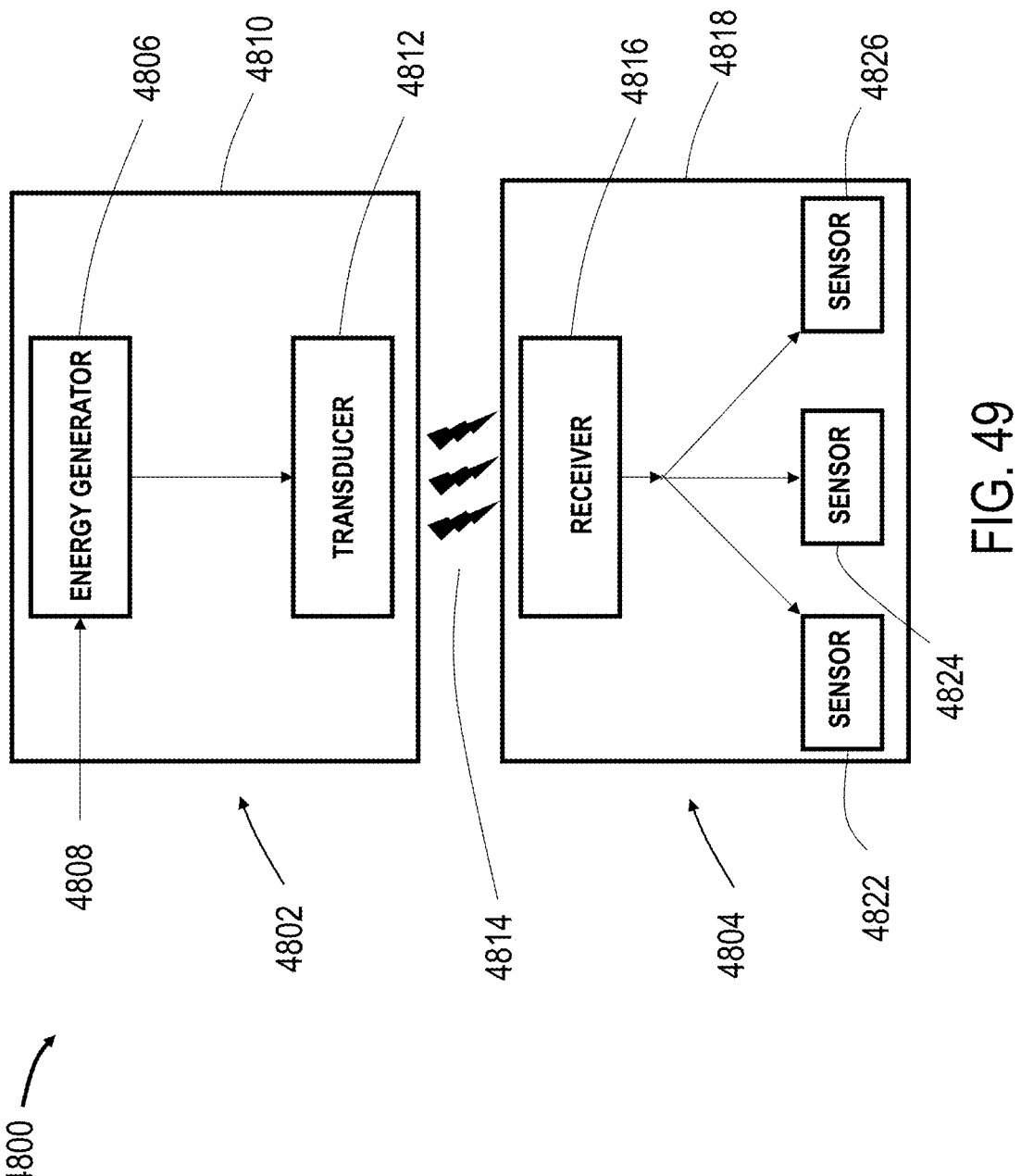
FIG. 49 is a schematic drawing of an implant with an energy generator according to another embodiment of the present disclosure.

Referring now to FIG. 49, there is shown a schematic drawing of an implant 4800 according to another embodiment of the present disclosure. Implant 4800 is similar to implant 4700, and therefore like elements are referred to with similar numerals within the 4800-series of numbers. For example, implant 4800 includes a first implant 4802 with an energy generator 4806 and a transducer 4812, and a second implant 4804 with a receiver 4816 and sensors 4822, 4824, 4826. However, second implant 4804 does not include a battery as electric energy from receiver 4816 is directly supplied to sensors 4822, 4824, 4826 as shown in FIG. 49. Thus, second implant 4804 can accommodate additional sensors within its body. Implant 4800 can be used in applications where the energy requirement of the sensors coincide with energy generation—i.e., energy generation and consumption occur simultaneously and therefore no energy storage by a battery is required. For example, a knee implant with sensors for measuring a patient's gait will require power only when the patient is walking. As energy generator 4806 creates energy while the patient walks (implant motion), the energy is directly supplied to sensors 4822, 4824, 4826 for gait measurement without the need for any storage. The sensors do not require power when the patient is at rest during which no energy is generated by energy generator 4806. In other embodiments, an energy storage device such as a super capacitor or the like can be used to store and supply energy to the sensors. A super capacitor charged to a predetermined threshold can provide energy to the sensor for sensor activity when no energy is being generated by the energy generator.

Figure 50:
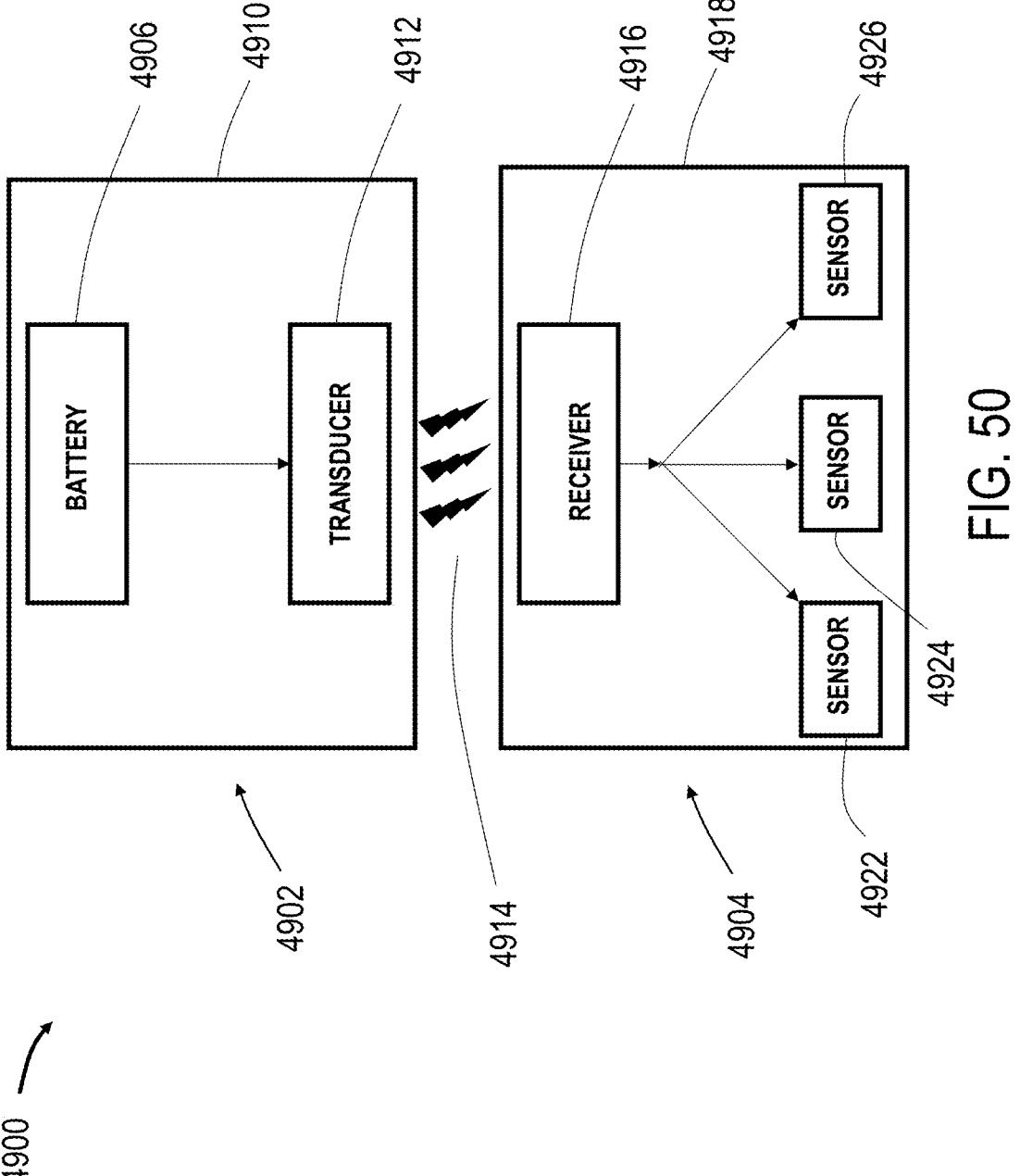
FIG. 50 is a schematic drawing of an implant with a battery according to an embodiment of the present disclosure.

FIG. 50 shows a schematic drawing of an implant 4900 according to another embodiment of the present disclosure. Implant 4900 is similar to implant 4700, and therefore like elements are referred to with similar numerals within the 4900-series of numbers. For example, implant 4900 includes a first implant 4902 with a transducer 4912, and a second implant 4904 with a receiver 4916 and sensors 4922, 4924, 4926. However, first implant 4902 has a battery 4906 instead of energy generator as shown in FIG. 50. Locating battery 4906 in first implant 4902 and acoustically transferring energy from this battery to second implant 4904 allows room for sensors and other electronics in the second implant. Implant 4900 can be used in applications where the second implant is considerably smaller than the first implant.

Figure 51:
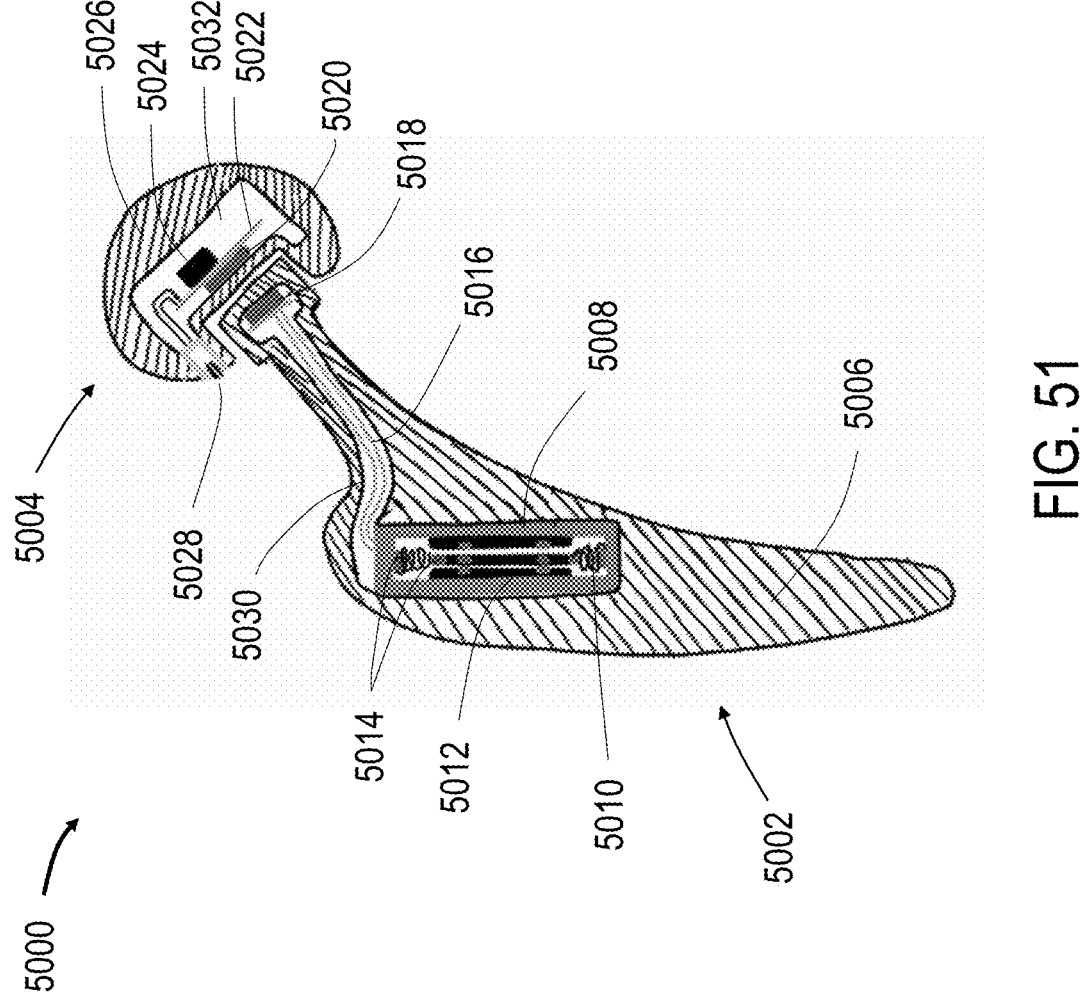
FIG. 51 is a front cross-sectional view of a hip implant according to an embodiment of the present disclosure.

FIG. 51 is a cross-section view of a hip implant 5000 according to an embodiment of the present disclosure. Hip implant 5000 includes a stem 5002 and a ball joint 5004. Stem 5002 includes an energy generator 5008 electrically connected to an ultrasonic transducer 5018 via a wire 5016. Energy generator 5008 and ultrasonic transducer 5018 are sealed within a body 5006 of stem 5002 as shown in FIG. 51. Energy generator 5008 is an electromechanical energy generator configured to convert mechanical energy to electrical energy. Energy generator 5008 includes a plurality of magnets 5014 located on fixed and moveable columns 5012 configured to generate electricity via the relative motion of the magnets. The relative motion of magnets 5014 triggered by various activities of the patient including walking, standing, etc. results in electric energy generation. Biasing members such as spring 5010 in energy generator 5008 protect magnets 5014 during hard impacts experienced by stem 5002 and aid in relative magnet motion to increase energy generation.

Electric energy generated by energy generator 5008 is transmitted to ultrasonic transducer 5018. Ultrasonic transducer 5018 converts the electrical energy received from energy generator 5008 to acoustic energy, and then acoustically transfers this energy to ultrasonic receiver 5020 of ball joint 5004 as shown in FIG. 51. Ultrasonic receiver 5020 is configured to receive acoustic energy (ultrasound) from ultrasonic transducer 5018 and convert this acoustic energy to electrical energy. Ultrasonic transducer 5018 and ultrasonic receiver 5020 can be sized and shaped based on the size and material composition of the stem and ball joint.

Ball joint 5004 includes a battery 5024 electrically connected to ultrasonic receiver 5020 and to a pH sensor 5028 via a printed circuit board (PCB) 5022 as shown in FIG. 51. pH sensor 5028 is located away from an acetabular component (not shown) to directly access synovial fluid to detect pH levels. Thus, the pH sensor does not interact with the acetabular component and is not impacted by acetabular component wear. Battery 5024 is a rechargeable battery configured to be charged by the electrical energy transmitted from ultrasonic receiver 5020. Battery 5024 can be any suitable biocompatible battery such as a solid state battery, lithium ion battery, lithium carbon monofluoride battery, lithium thionyl chloride battery, lithium ion polymer battery, etc. As battery 5024 is frequently charged during patient activity, the size and capacity of battery 5024 can be substantially minimized Thus, a smaller battery provides additional space for various sensors and associated electronics located within ball joint 5004. Ball joint 5004 can include various other sensors such as a temperature sensor, pressure sensor, etc., depending on the desired measurements.

Ultrasonic energy transfer between stem 5002 and ball joint 5004 can be utilized with implants made of dissimilar materials such as cobalt-chromium (CoCr), Titanium (Ti), cross-linked polyethylene (XLPE), etc. Ultrasonic energy transfer allows the various electronic components of stem 5002 and ball joint 5004 to be safely sealed within these implants. Wires or other components extending outside the stem and ball joint to directly couple these implants are not required for ultrasonic energy transfer thereby eliminating potential structural weakness in the implant bodies which may be susceptible to failure. Stem 5002 and ball joint 5004 can be hermetically sealed to improve implant biocompatibility and patient safety.

Figure 52:
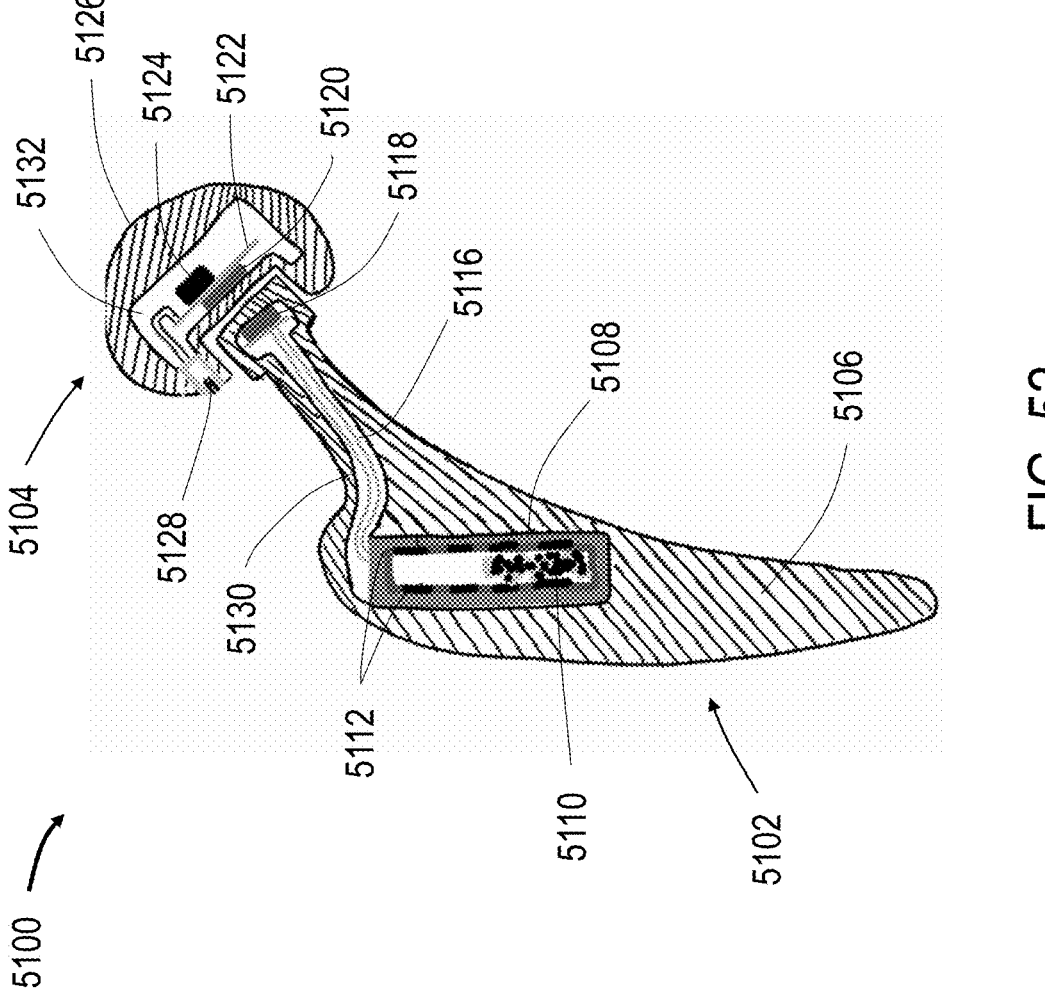
FIG. 52 is a front cross-sectional view of a hip implant according to another embodiment of the present disclosure.

A cross-sectional drawing of a hip implant 5100 according to another embodiment of the present disclosure is shown in FIG. 52. Hip implant 5100 is similar to hip implant 5000, and therefore like elements are referred to with similar numerals within the 5100-series of numbers. For example, hip implant 5100 includes a stem 5102 with an energy generator 5108, and a ball joint 5104 with an ultrasonic receiver 5120 and a battery 5124. However, energy generator 5108 of hip implant 5100 is a triboelectric energy generator. Energy generator 5108 includes triboelectric material 5110 and triboelectric receptors 5112 as shown in FIG. 52. Triboelectric material 5110 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in hip implant 5100.

Figure 53:
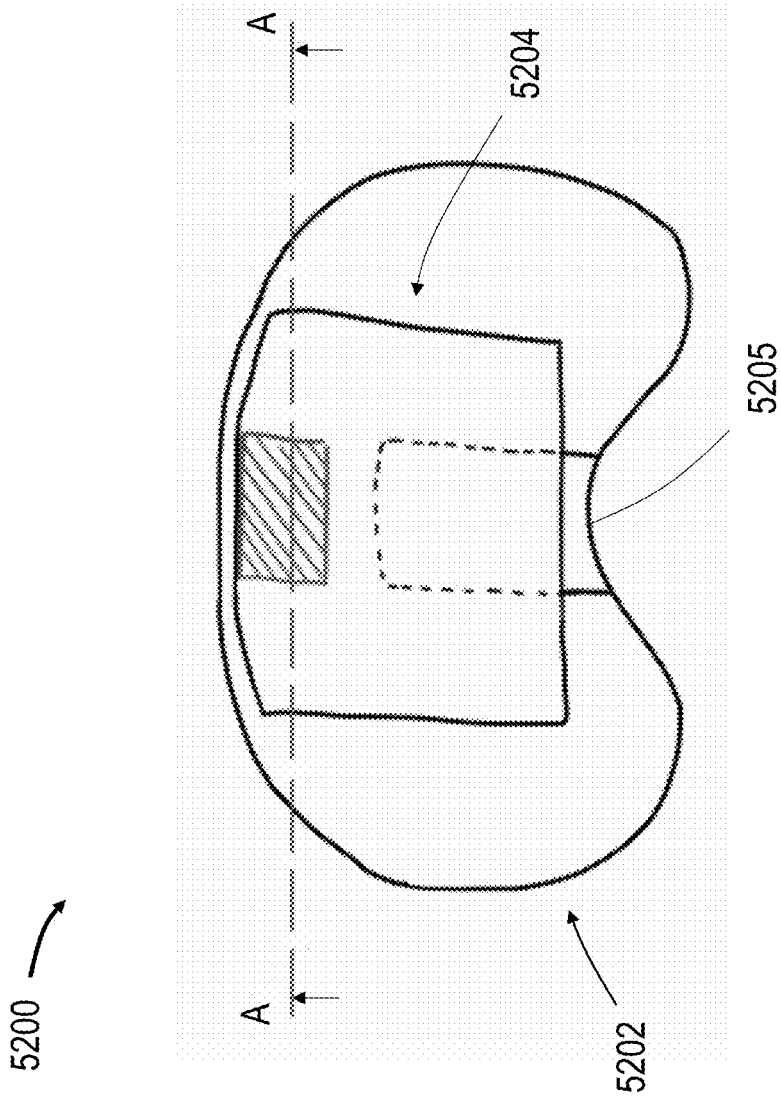
FIG. 53 is top view of a knee implant according to an embodiment of the present disclosure.
Figure 54:
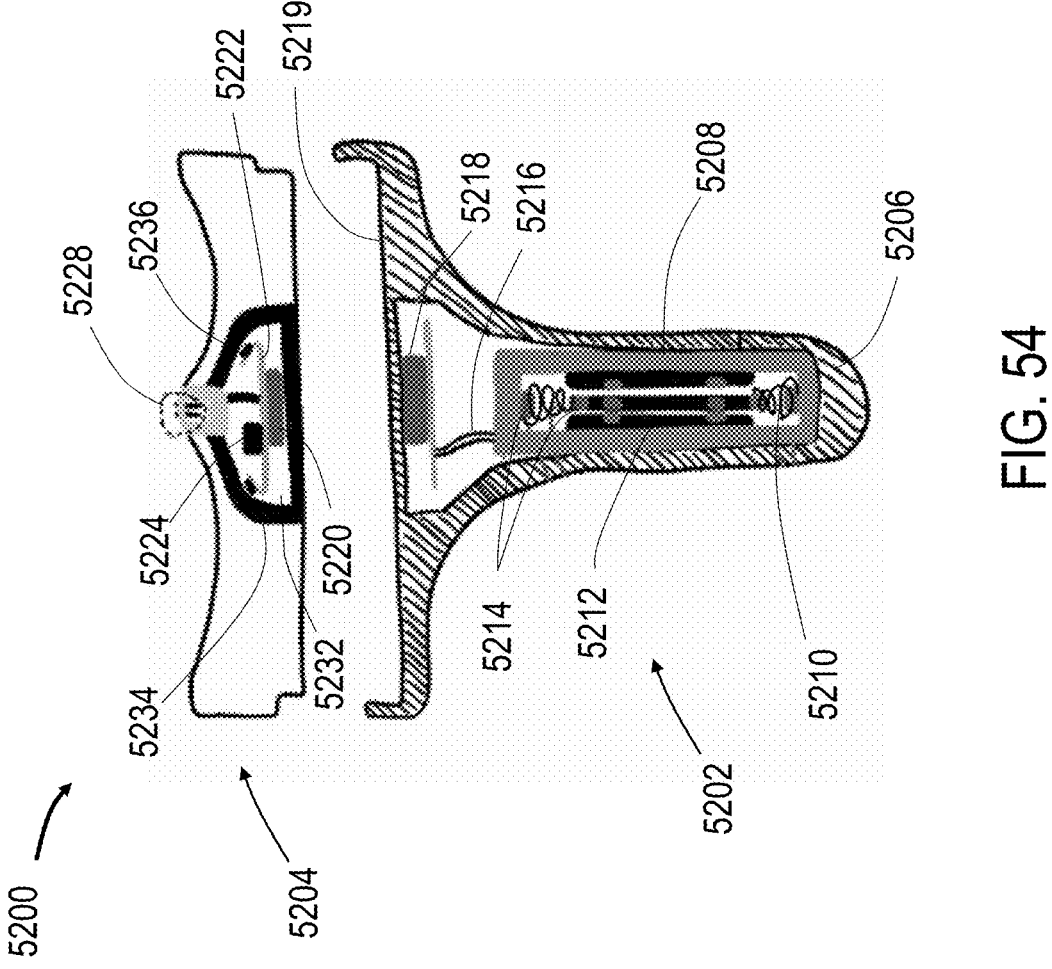
FIG. 54 is a front cross-sectional view of the knee implant of FIG. 53 taken along line A-A.

Referring now to FIGS. 53 and 54, there is shown a knee implant 5200 according to an embodiment of the present disclosure. Knee implant 5200 includes a tibial stem 5202 and a tibial insert 5204. A locking mechanism 5205 secures tibial insert 5204 to tibial stem 5202 as best shown in FIG. 53. Tibial stem 5202 includes an energy generator 5208 electrically connected to an ultrasonic transducer 5218 via a wire 5216. Energy generator 5208 and ultrasonic transducer 5218 are sealed within a body 5206 of tibial stem 5202 as best shown in FIG. 54. Energy generator 5208 is an electromechanical energy generator configured to convert mechanical energy to electrical energy. Energy generator 5208 includes a plurality of magnets 5214 located on fixed and moveable columns 5212 configured to generate electricity via the relative motion of the magnets. The relative motion of magnets 5214 triggered by various activities of the patient including walking, standing, etc. results in electric energy generation. Biasing members such as spring 5210 in energy generator 5208 protect magnets 5214 during hard impacts experienced by tibial stem 5202 and aid in relative magnet motion to increase energy generation.

Electric energy generated by energy generator 5208 is transmitted to ultrasonic transducer 5218. Ultrasonic transducer 5218 converts the electrical energy received from energy generator 5208 to acoustic energy, and then acoustically transfers this energy to ultrasonic receiver 5220 of tibial insert 5204 as shown in FIG. 54. Ultrasonic receiver 5220 is configured to receive acoustic energy (ultrasound) from ultrasonic transducer 5218 and convert this acoustic energy to electrical energy. Ultrasonic transducer 5218 and ultrasonic receiver 5220 can be sized and shaped based on the size and material composition of the tibial stem and tibial insert.

Tibial insert 5204 includes a battery 5224 electrically connected to ultrasonic receiver 5220 and a pH sensor 5228 via a printed circuit board (PCB) 5222 as shown in FIG. 54. pH sensor 5228 is located at an apex between medial and lateral condyle contact surface to directly access synovial fluid and detect pH levels. The various electronic components of tibial insert 5204 are located within a cavity 5232 surrounded by a housing 5234 as shown in FIG. 54. Housing 5234 may be metallic to hermetically seal and protect the electronic components.

Battery 5224 is a rechargeable battery configured to be charged by the electrical energy transmitted from ultrasonic receiver 5220. Battery 5224 can be any suitable biocompatible battery such as a solid state battery, lithium ion battery, lithium carbon monofluoride battery, lithium thionyl chloride battery, lithium ion polymer battery, etc. As battery 5224 is frequently charged during patient activity, the size and capacity of battery 5224 can be substantially minimized. Thus, a smaller battery provides additional space for various sensors and associated electronics located within tibial insert 5204. Tibial insert 5204 can include various other sensors such as a temperature sensor, pressure sensor, etc., depending on the desired measurements.

Ultrasonic energy transfer between tibial stem 5202 and tibial insert 5204 can be utilized with implants made of varied materials such as cobalt-chromium (CoCr), Titanium (Ti), cross-linked polyethylene (XLPE), etc. Ultrasonic energy transfer allows the various electronic components of tibial stem 5202 and tibial insert 5204 to be safely sealed within these implants while allowing efficient energy transfer across these materials including a top surface of tibial stem 5222. Wires or other components extending outside the tibial stem and tibial insert to directly couple these implants are not required for ultrasonic energy transfer thereby eliminating potential structural weakness in the implant bodies which may be susceptible to failure. Tibial stem 5202 and tibial insert 5204 can be hermetically sealed to improve implant biocompatibility and patient safety.

Figure 55:
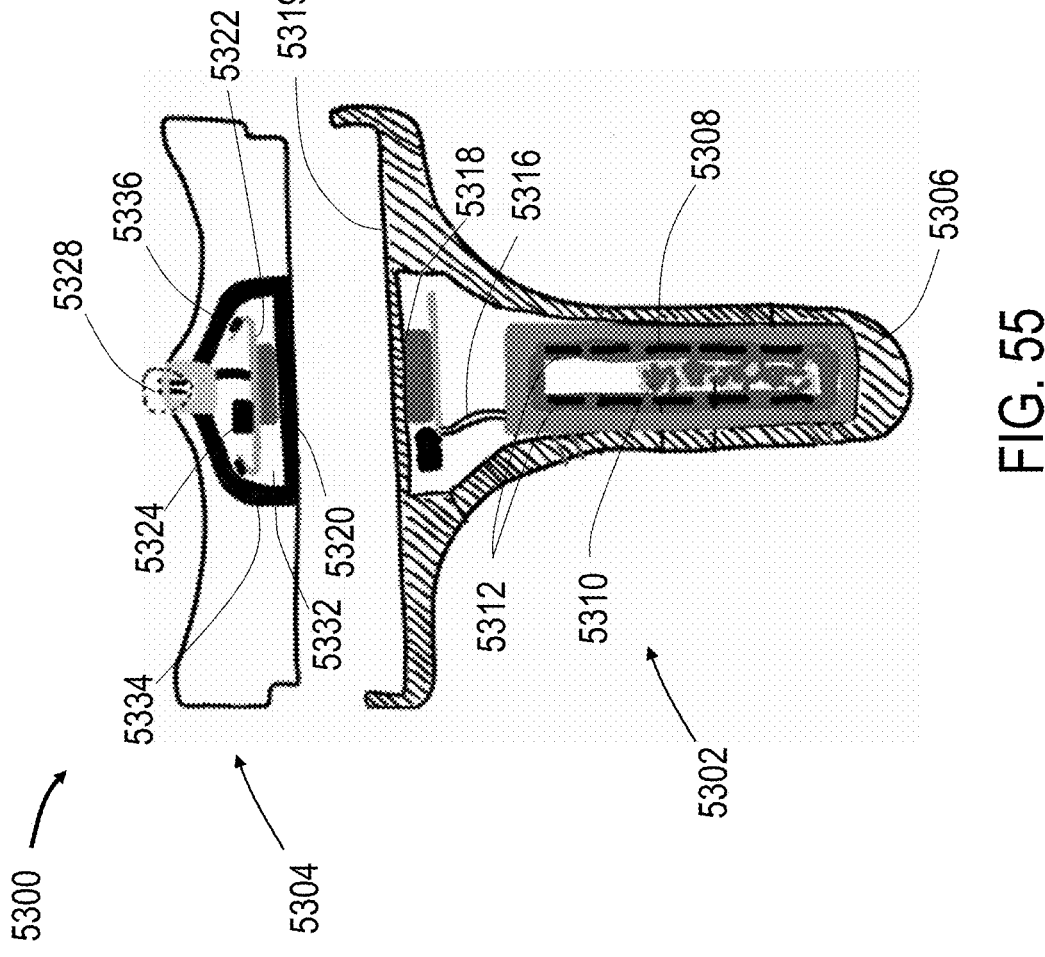
FIG. 55 is a front cross-sectional view of a knee implant according to another embodiment of the present disclosure.

FIG. 55 shows a cross-sectional drawing of a knee implant 5300 according to another embodiment of the present disclosure. Knee implant 5300 is similar to knee implant 5200, and therefore like elements are referred to with similar numerals within the 5300-series of numbers. For example, knee implant 5300 includes a tibial stem 5302 with an energy generator 5308, and a tibial insert 5304 with an ultrasonic receiver 5320 and a battery 5324. However, energy generator 5308 of knee implant 5300 is a triboelectric energy generator. Energy generator 5308 includes triboelectric material 5310 and triboelectric receptors 5312 as shown in FIG. 55. Triboelectric material 5310 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in knee implant 5300.

Figure 56:
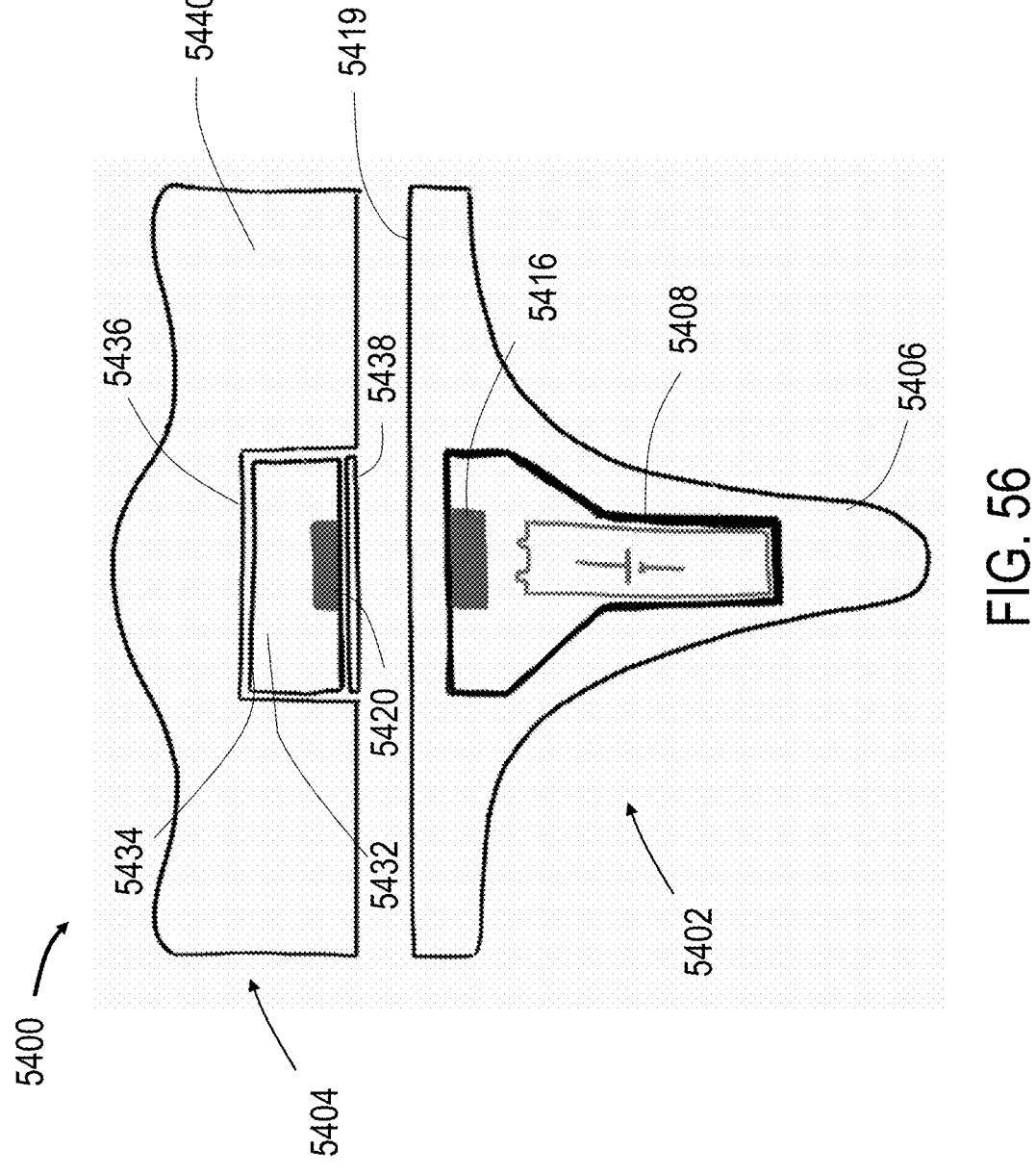
FIG. 56 is a front cross-sectional view of a knee implant according to another embodiment of the present disclosure.

FIG. 56 shows a cross-sectional drawing of a knee implant 5400 according to another embodiment of the present disclosure. Knee implant 5400 is similar to knee implant 5200, and therefore like elements are referred to with similar numerals within the 5400-series of numbers. For example, knee implant 5400 includes a tibial stem 5402 with an ultrasonic transducer 5416, and a tibial insert 5404 with an ultrasonic receiver 5420. However, tibial stem 5402 includes a battery 5408 instead of an energy generator. Locating battery 5408 in tibial stem 5402 and acoustically transferring energy from this battery to tibial insert 5404 allows room for sensors and other electronics in the tibial insert. Tibial stem 5402 being larger than tibial insert 5404 can accommodate a larger batter. Battery 5408 is a rechargeable battery that can be recharged by an external device via induction charging or other means.

Tibial insert 5404 does not include a battery as electric energy from ultrasonic receiver 5420 is directly supplied to sensors located in the tibial insert (not shown). Thus, tibial insert 5404 can accommodate additional sensors within its body. Knee implant 5400 includes a baseplate 5438 made of a XLPE.

Figure 57:
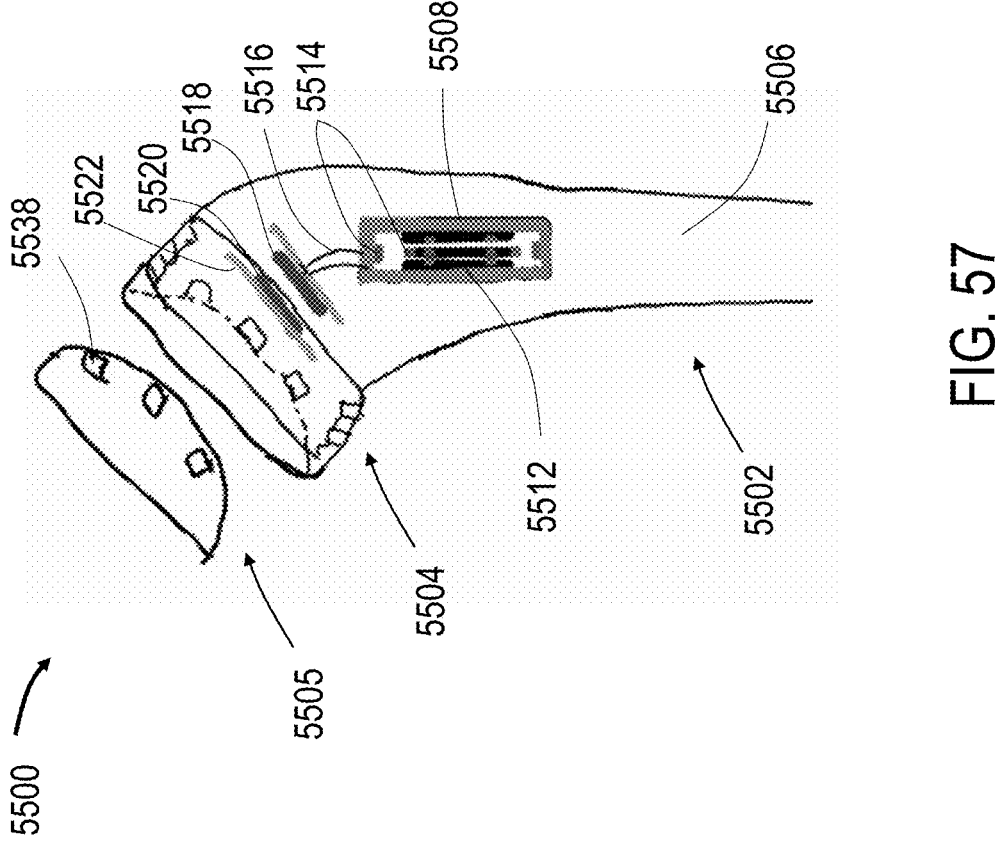
FIG. 57 is a front cross-sectional view of a shoulder implant according to an embodiment of the present disclosure.

FIG. 56 is a cross-section view of a shoulder implant 5500 according to an embodiment of the present disclosure. Shoulder implant 5500 includes a stem 5502 and a glenoid sphere 5504. Stem 5502 includes an energy generator 5508 electrically connected to an ultrasonic transducer 5518 via a wire 5516. Energy generator 5508 and ultrasonic transducer 5518 are sealed within a body 5506 of stem 5502 as shown in FIG. 57. Energy generator 5508 is an electromechanical energy generator configured to convert mechanical energy to electrical energy. Energy generator 5508 includes a plurality of magnets 5514 located on fixed and moveable columns 5512 configured to generate electricity via the relative motion of the magnets. The relative motion of magnets 5514 triggered by various activities of the patient including walking, standing, etc. results in electric energy generation. Biasing members such as a spring 5510 in energy generator 5508 protect magnets 5514 during hard impacts experienced by stem 5502 and aid in relative magnet motion to increase energy generation.

Electric energy generated by energy generator 5508 is transmitted to ultrasonic transducer 5518. Ultrasonic transducer 5518 converts the electrical energy received from energy generator 5508 to acoustic energy, and then acoustically transfers this energy to ultrasonic receiver 5520 of glenoid sphere 5504 as shown in FIG. 57. Ultrasonic receiver 5520 is configured to receive acoustic energy (ultrasound) from ultrasonic transducer 5518 and convert this acoustic energy to electrical energy. Ultrasonic transducer 5518 and ultrasonic receiver 5520 can be sized and shaped based on the size and material composition of the stem and glenoid sphere.

Glenoid sphere 5504 includes a battery (not shown) electrically connected to ultrasonic receiver 5520 and to various sensors (not shown) via a printed circuit board (PCB) 5522. The battery is a rechargeable battery configured to be charged by the electrical energy transmitted from ultrasonic receiver 5520. As the battery is frequently charged during patient activity, the size and capacity of the battery can be substantially minimized Thus, a smaller battery provides additional space for various sensors and associated electronics located within glenoid sphere 5504. Glenoid sphere 5504 can include various other sensors such as a temperature sensor, pressure sensor, etc., depending on the desired measurements.

Ultrasonic energy transfer between stem 5502 and glenoid sphere 5504 can be utilized with implants made of different materials such as cobalt-chromium (CoCr), Titanium (Ti), cross-linked polyethylene (XLPE), etc. Ultrasonic energy transfer allows the various electronic components of stem 5502 and glenoid sphere 5504 to be safely sealed within these implants. Wires or other components extending outside the stem and glenoid sphere to directly couple these implants are not required for ultrasonic energy transfer thereby eliminating potential structural weakness in the implant bodies which may be susceptible to failure. Stem 5502 and glenoid sphere 5504 can be hermetically sealed to improve implant biocompatibility and patient safety.

Figure 58:
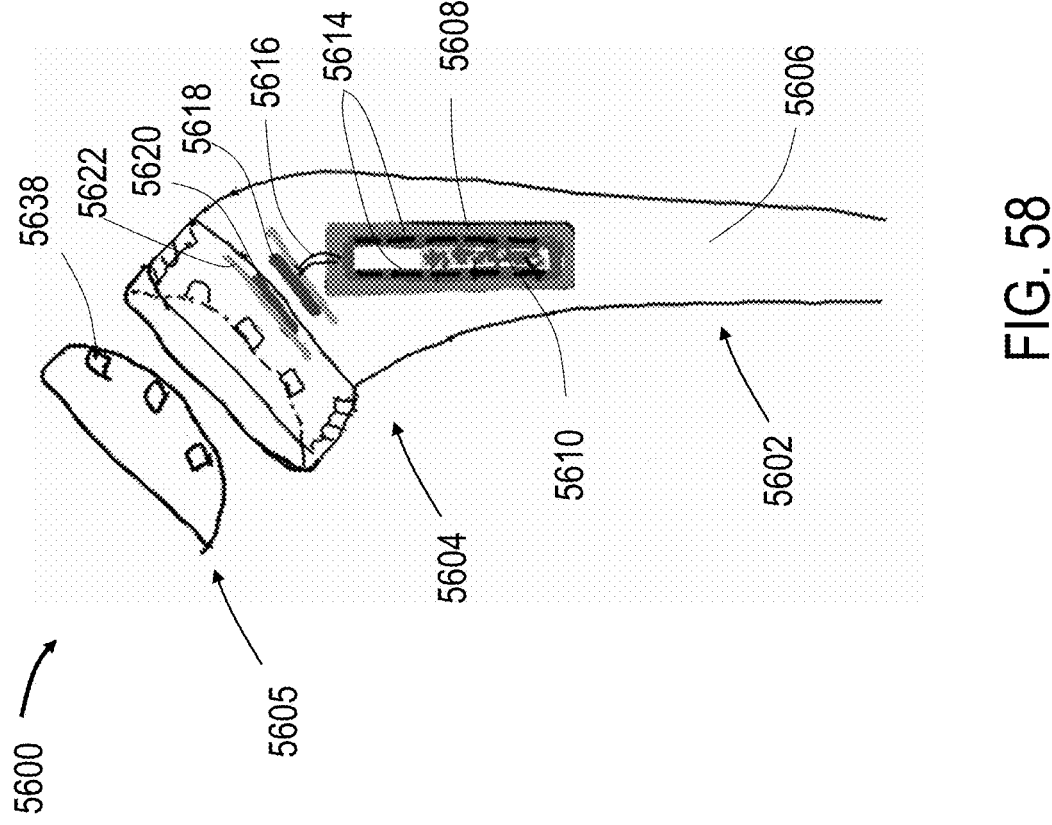
FIG. 58 is a front cross-sectional view of a shoulder implant according to another embodiment of the present disclosure.
Figure 59:
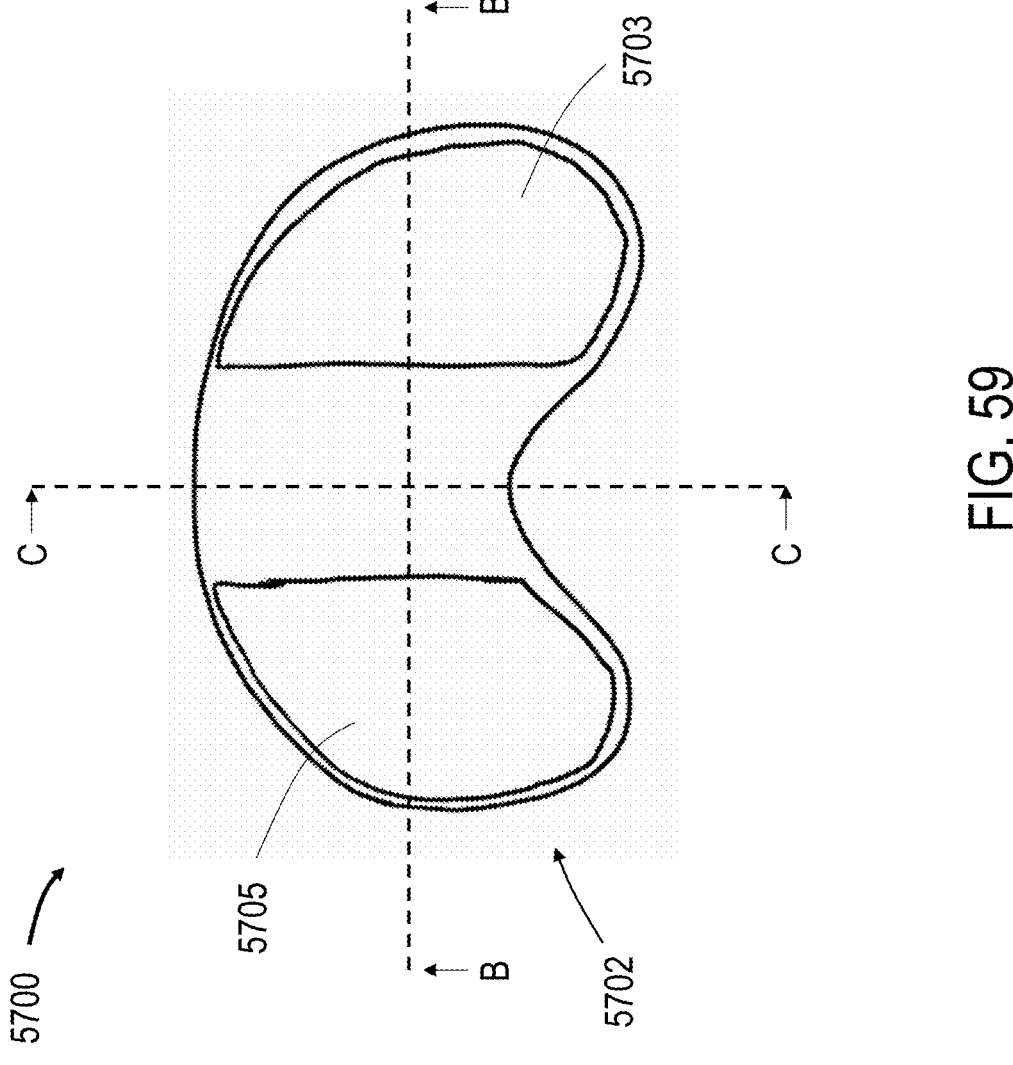
FIG. 59 is a top view of a knee implant according to another embodiment of the present disclosure.
Figures 60A, 60B:
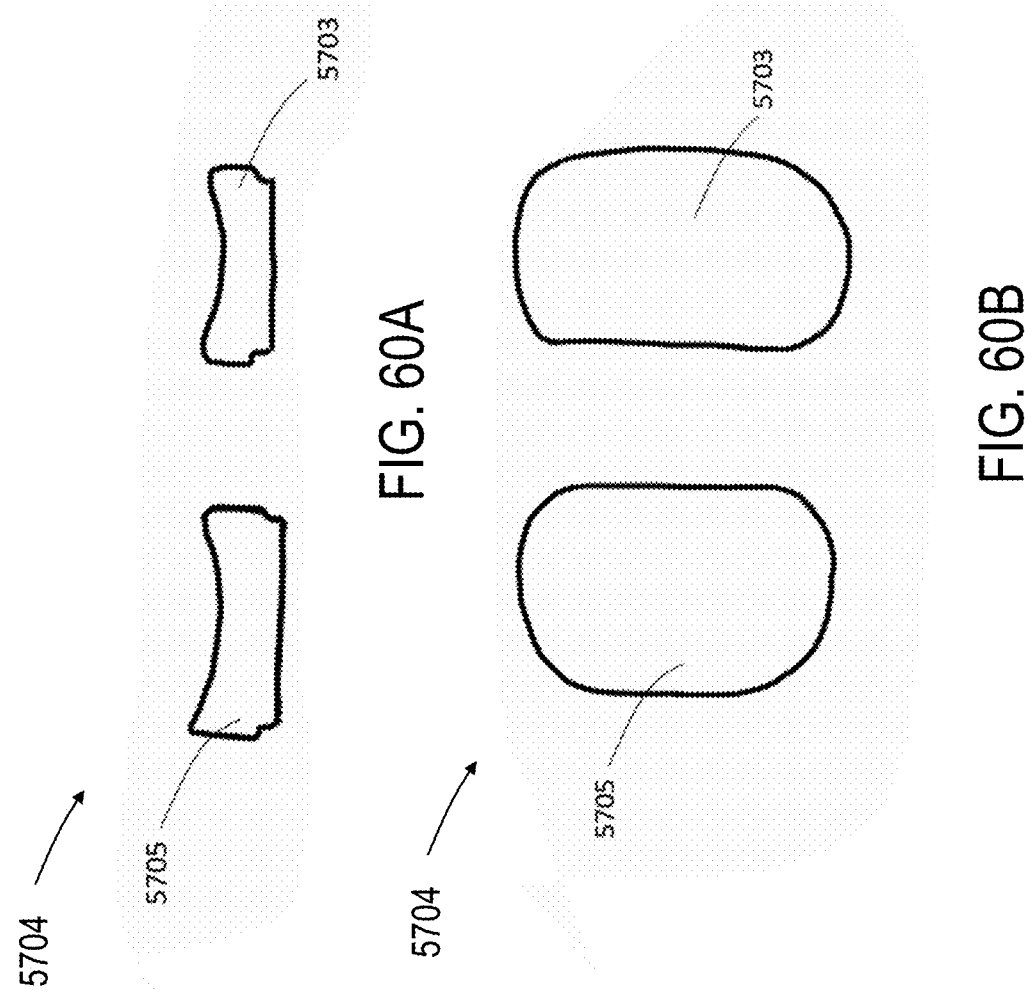
FIG. 60A is a side view of tibial inserts of the knee implant of FIG. 59.
FIG. 60B is a top view of the tibial inserts of the knee implant of FIG. 59.

A cross-sectional drawing of a shoulder implant 5600 according to another embodiment of the present disclosure is shown in FIG. 58. Shoulder implant 5600 is similar to shoulder implant 5500, and therefore like elements are referred to with similar numerals within the 5600-series of numbers. For example, shoulder implant 5600 includes a stem 5602 with an energy generator 5608, and a glenoid sphere 5604 with an ultrasonic receiver 5620 and a battery (not shown). However, energy generator 5608 of shoulder implant 5600 is a triboelectric energy generator. Energy generator 5608 includes triboelectric material 5610 and triboelectric receptors 5612 as shown in FIG. 58. Triboelectric material 5610 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in shoulder implant 5600.

Figure 61:
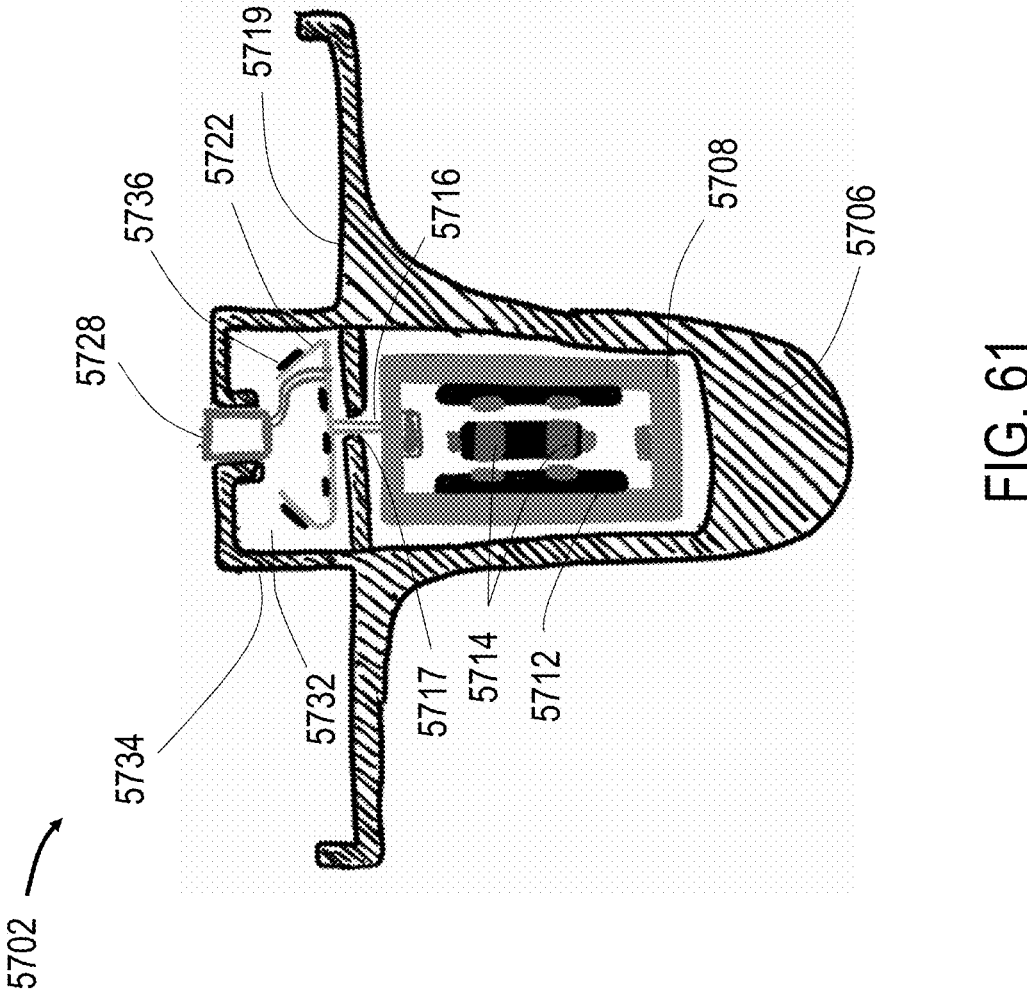
FIG. 61 is a side cross-sectional view of a tibial stem of the knee implant of FIG. 59 taken along line B-B.

FIGS. 59-62 show a knee implant 5700 according to another embodiment of the present disclosure. Knee implant 5700 is similar to knee implant 5200, and therefore like elements are referred to with similar numerals within the 5700-series of numbers. For example, knee implant 5700 includes a tibial stem 5702 with an energy generator 5708, and a tibial insert 5704 as shown in FIG. 61. However, tibial insert 5704 includes a medial tibial insert 5705 and a lateral tibial insert 5703 as best shown in FIGS. 60A and 60B. Individual tibial inserts on the medial and lateral sides allow a surgeon to use tibial inserts with asymmetric insert thicknesses to balance the knee or to vary constrains between both inserts to facilitate mobility. For example, a surgeon can select a medial tibial insert to constraint medial ligaments for a specific patient. Ligament anomalies identified during pre-op or intra-op assessments with a smart trial component for instance allow the surgeon to vary the individual tibial inserts to address the needs of a particular patient.

Figure 62:
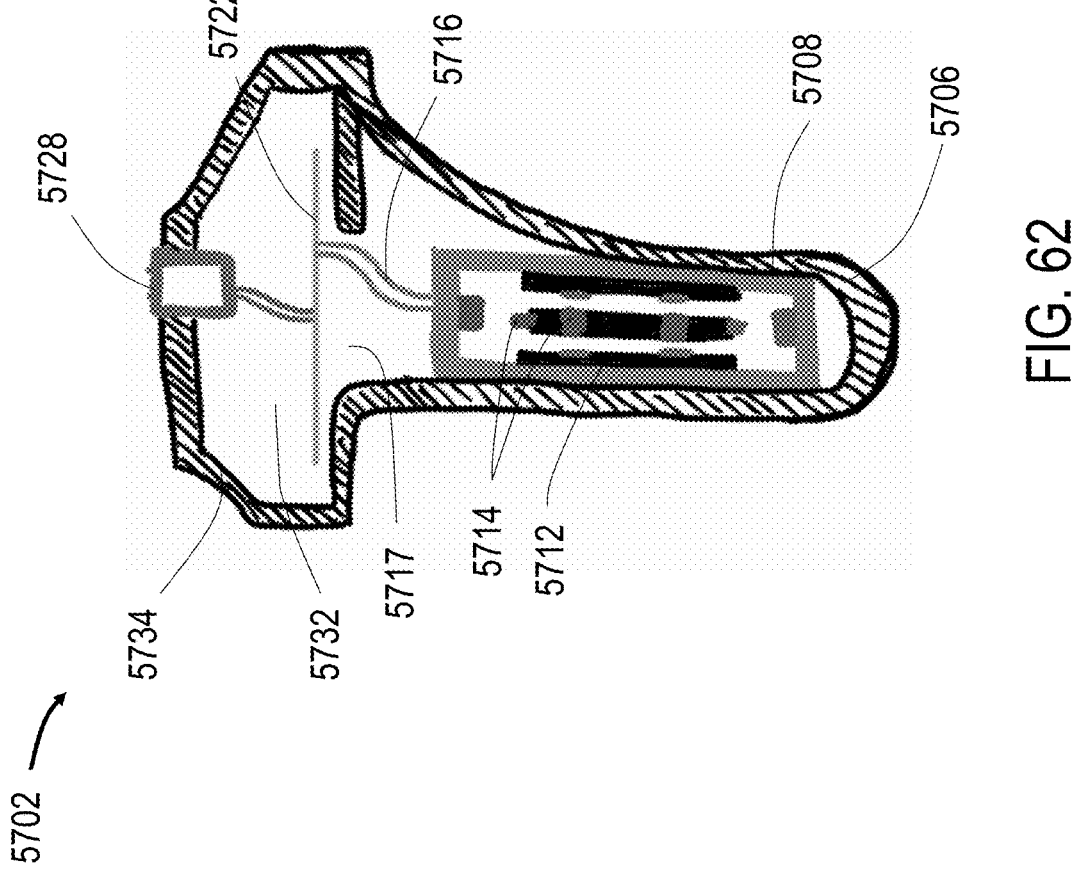
FIG. 62 is a side cross-sectional view of the tibial stem of the knee implant of FIG. 59 taken along line C-C.

Tibial stem 5702 of knee implant 5700 includes an extension with a cavity 5732 to accommodate electronic components such as PCB 5722 and sensors 5736. An opening 5717 in cavity 5732 allows energy generator 5718 to power the various electronic component located in the cavity via a wire 5716 as best shown in FIGS. 61 and 62. Thus, the energy generator and all electronic components of knee implant 5700 can be located within a single implant (tibial stem 5702) in this embodiment. A pH sensor 5728 extends through a proximal surface of tibial stem 5702 to directly contact synovial fluid for precise and accurate measurement of synovial fluid pH levels. Cavity 5732 can be hermetically sealed to protect the electronic components.

Energy generator 5708 is an electromechanical energy generator configured to convert mechanical energy to electrical energy. Energy generator 5708 includes a plurality of magnets 5714 located on fixed and moveable columns 5712 configured to generate electricity via the relative motion of the magnets. The relative motion of magnets 5714 triggered by various activities of the patient including walking, standing, etc. results in electric energy generation. Biasing members (not shown) in energy generator 5708 protect magnets 5714 during hard impacts experienced by tibial stem 5702 and aid in relative magnet motion to increase energy generation. Electric power generated from energy generator 5708 is directly supplied (via wire 5716) to the various electronic components located in cavity 5732. In other embodiments, tibial stem 5702 can include a battery to store energy and supply same to the electronic components of tibial stem.

While a knee joint implant, hip implant, and shoulder implant are disclosed above, all or any of the aspects of the present disclosure can be used with any other implant such as an intramedullary nail, a bone plate, a spinal implant, a bone screw, an external fixation device, an interference screw, etc. For example, an energy generator disposed within a fastening element of a spinal implant such as a screw can be used to generate energy and acoustically transmit this energy to power sensors located within a spinal implant such as a spinal plate.

Although, the present disclosure generally refers to implants, the systems and method disclosed above can be used with trials to provide real time information related to trial performance. While the electronic components disclosed above are generally located in the tibial implant (tibial insert and stem) of the knee joint implant, the electronic components can be located within the femoral implant in other embodiments. Battery and transducer-receiver shape, size and configuration can be customized based on the type of implant and patient-specific needs.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A joint implant comprising:
a first implant configured to be coupled to a first bone of a joint, the first implant including an energy generator coupled to a transducer, the transducer being disposed within the first implant, and
a second implant disposed adjacent the first implant, the second implant including:
at least one sensor;
a battery coupled to the least one sensor, and
a receiver coupled to the battery, the receiver being disposed within the second implant adjacent the transducer,
wherein energy from the energy generator is transmitted from the transducer of the first implant to the receiver of the second implant.

2. The joint implant of claim 1, wherein energy from the energy generator is acoustically transmitted from the transducer of the first implant to the receiver of the second implant.

3. The joint implant of claim 2, wherein the transducer is an ultrasonic transducer.

4. The joint implant of claim 3, wherein the receiver is an ultrasonic receiver.

5. The joint implant of claim 4, wherein energy from the energy generator is ultrasonically transmitted from the ultrasonic transducer of the first implant to the ultrasonic receiver of the second implant.

6. The joint implant of claim 1, wherein the energy generator includes a plurality of magnets.

7. The joint implant of claim 6, wherein the energy generator generates energy by magnetic induction caused by motion between the plurality of magnets.

8. The joint implant of claim 7, wherein the motion between the plurality of magnets is caused by joint implant motion.

9. The joint implant of claim 7, wherein the energy generator includes one or more biasing elements coupled to the magnets.

10. The joint implant of claim 9, wherein the biasing elements are springs or biasing magnets.

11. The joint implant of claim 1, wherein the energy generator includes triboelectric material.

12. The joint implant of claim 11, wherein the triboelectric material includes a first triboelectric layer with a first electron affinity and a second triboelectric layer with a second electron affinity, the first electron affinity being different from the second electron affinity.

13. The joint implant of claim 12, wherein the first triboelectric layer is separated by a distance from the second triboelectric layer.

14. The joint implant of claim 13, wherein a motion of the joint implant causes the distance to vary to generate energy.

15. The joint implant of claim 12, wherein the first triboelectric layer slides along the second triboelectric layer during joint implant motion to generate energy.

16. An implant system comprising:
a first implant configured to be coupled to a first bone of a joint, the first implant including an energy generator coupled to a transducer, the transducer being disposed within the first implant, and
a second implant disposed adjacent the first implant, the second implant including:
at least one sensor, and
a receiver coupled to the at least one sensor, the receiver being disposed within the second implant adjacent the transducer,
wherein energy from the energy generator is acoustically transmitted from the transducer of the first implant to the receiver of the second implant.

17. The implant system of claim 16, wherein the transducer is an ultrasonic transducer, and the receiver is an ultrasonic receiver.

18. The implant system of claim 17, wherein energy from the energy generator is ultrasonically transmitted from the ultrasonic transducer of the first implant to the ultrasonic receiver of the second implant.

19. A method for powering a joint implant, the method comprising the steps of:
providing a first implant configured to be placed on a first bone;
coupling an energy generator of the first implant to a transducer, the transducer being disposed within the first implant;
providing a second implant configured to be placed in contact with the first implant;
coupling at least one sensor disposed within the second implant to a battery, the battery being disposed within the second implant;
coupling a receiver to the battery, the receiver being disposed within the second implant adjacent the transducer, and
transmitting energy from the energy generator to the transducer of the first implant to the receiver of the second implant.

20. The method of claim 19, wherein the step of transmitting energy includes acoustically transmitting energy from the transducer of the first implant to the receiver of the second implant.

* * * * *